US010550394B2

(12) United States Patent
Rossi et al.

(10) Patent No.: US 10,550,394 B2
(45) Date of Patent: Feb. 4, 2020

(54) ANTI-CANCER RNA APTAMERS

(71) Applicants: CITY OF HOPE, Duarte, CA (US); APTERNA LTD, London (GB)

(72) Inventors: John J. Rossi, Monrovia, CA (US); Sorah Yoon, Pasadena, CA (US); Nagy Habib, London (GB)

(73) Assignees: CITY OF HOPE, Duarte, CA (US); APTERNA LTD, London (GB)

( * ) Notice: Subject to any disclaimer, the term of this patent is extended or adjusted under 35 U.S.C. 154(b) by 6 days.

(21) Appl. No.: 15/563,099

(22) PCT Filed: Mar. 31, 2016

(86) PCT No.: PCT/US2016/025351
§ 371 (c)(1),
(2) Date: Sep. 29, 2017

(87) PCT Pub. No.: WO2016/161165
PCT Pub. Date: Oct. 6, 2016

(65) Prior Publication Data
US 2018/0087053 A1 Mar. 29, 2018

Related U.S. Application Data

(60) Provisional application No. 62/141,156, filed on Mar. 31, 2015.

(51) Int. Cl.
*C12N 15/11* (2006.01)
*C12N 15/115* (2010.01)
*C12N 15/113* (2010.01)

(52) U.S. Cl.
CPC ........ *C12N 15/115* (2013.01); *C12N 15/1135* (2013.01); *C12N 2310/14* (2013.01); *C12N 2310/16* (2013.01); *C12N 2310/3519* (2013.01); *C12N 2320/32* (2013.01)

(58) Field of Classification Search
None
See application file for complete search history.

(56) References Cited

U.S. PATENT DOCUMENTS

| 2007/0130645 A1 | 6/2007 | Wu et al. |
| 2010/0221183 A1 | 9/2010 | Squires |
| 2013/0101506 A1 | 4/2013 | Smith |

FOREIGN PATENT DOCUMENTS

WO WO-2013/154735 A1 10/2013

OTHER PUBLICATIONS

Elpek, G.O. et al. (Apr. 2003). "Expression of heat-shock proteins hsp27, hsp70 and hsp90 in malignant epithelial tumour of the ovaries," *APMIS* 111(4):523-530.
GenBank Accession No. DW675250.1, (Jan. 19, 2006). CNB386-G08.y1d-s SHGC-CNB2 Gasterosteus aculeatus Cdna clone CNB386-G08 5-, mRNA sequence, located at <http://www.ncbi.nlm.nih.gov/nucest/DW675250> last visited May 29, 2018, 2 pages.
Hantschel, M. et al. (Nov. 2000). "Hsp70 plasma membrane expression on primary tumor biopsy material and bone marrow of leukemic patients," *Cell Stress & Chaperones* 5(5):438-442.
Huan, H. et al. (Apr. 6, 2016). "C/EBPα Short-Activating RNA Suppresses Metastasis of Hepatocellular Carcinoma through Inhibiting EGFR/β-Catenin Signaling Mediated EMT," *PLoS One* 11(4):e0153117.
International Search Report dated Aug. 12, 2016, for PCT Application No. PCT/US2016/025351, filed Mar. 31, 2016, 5 pages.
Leu, J.I. et al. (Oct. 9, 2009). "A small molecule inhibitor of inducible heat shock protein 70," *Mol Cell* 36(1):15-27.
Nylandsted, J. et al. (Jul. 5, 2000). "Selective depletion of heat shock protein 70 (Hsp70) activates a tumor-specific death program that is independent of caspases and bypasses Bcl-2," *PNAS USA* 97(14):7871-7876.
Reebye, V. et al. (Jan. 2014, e-published Dec. 9, 2013). "Novel RNA oligonucleotide improves liver function and inhibits liver carcinogenesis in vivo," *Hepatology* 59(1):216-227.
Rérole, A.L. et al. (Jan. 15, 2011. e-published Jan. 11, 2011). "Peptides and aptamers targeting HSP70: a novel approach for anticancer chemotherapy," *Cancer Res* 7192)484-495.
Stathis, A. et al. (Mar. 2010, e-published Jan. 26, 2010). "Advanced pancreatic carcinoma: current treatment and future challenges," *Nat Rev Clin Oncol* 7(3):163-172.
Written Opinion dated Aug. 12, 2016, for PCT Application No. PCT/US2016/025351, filed Mar. 31, 2016, 7 pages.

*Primary Examiner* — Ekaterina Poliakova-Georgantas
(74) *Attorney, Agent, or Firm* — Mintz, Levin, Cohn, Ferris, Glovsky and Popeo, P.C.

(57) ABSTRACT

Provided herein, inter alia, are compounds capable of binding HSP70 (e.g. mHSP70) on a cell and internalizing into said cell. The compositions provided herein may be useful for delivering therapeutic and diagnostic agents to a cell. Further provided are pharmaceutical compositions and methods of treatment using nucleic acid compounds provided herein.

27 Claims, 26 Drawing Sheets

Specification includes a Sequence Listing.

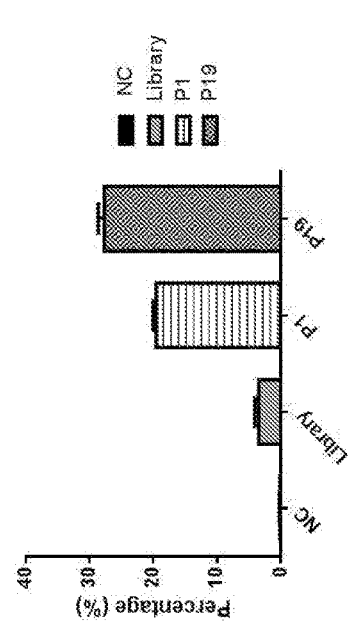
FIG. 1A
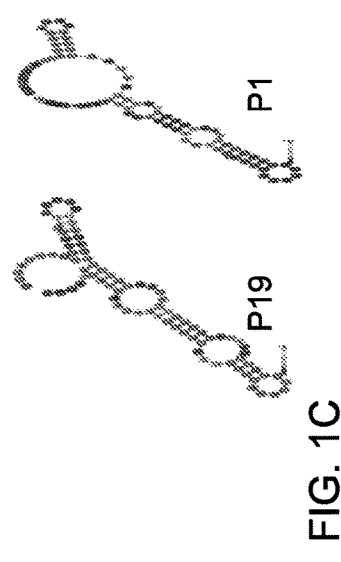
FIG. 1B
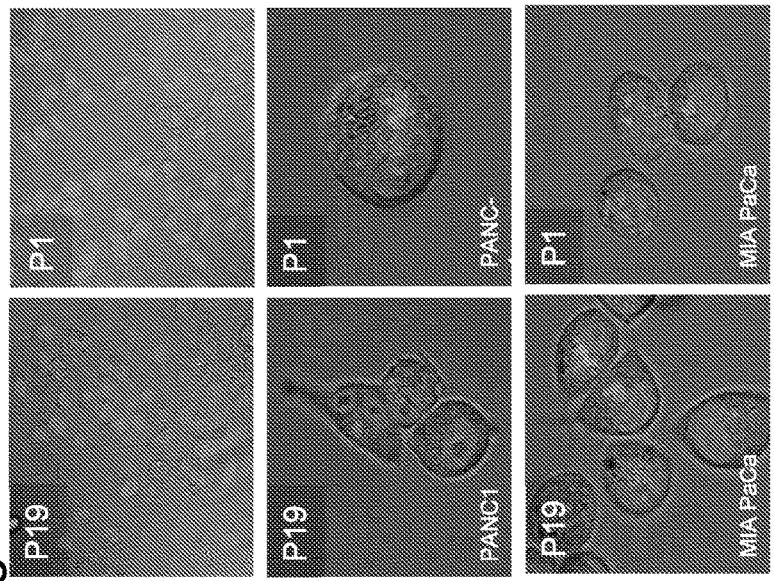
FIG. 1C
FIG. 1D

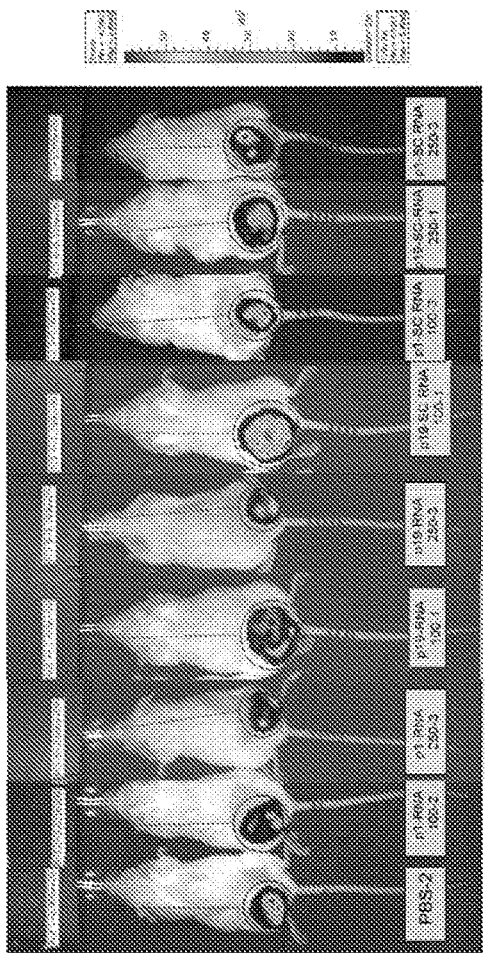
FIG. 5C
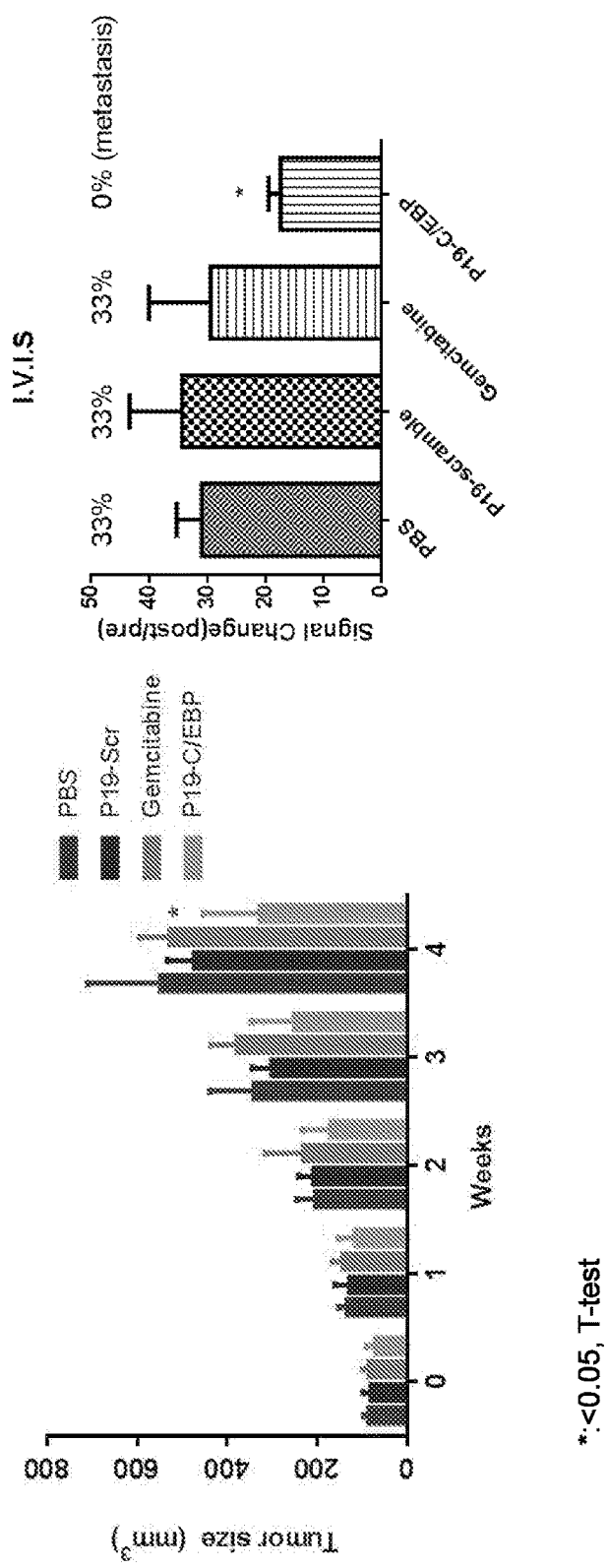
FIG. 5E
FIG. 5D

1. C/EBP
2. C/EBP- P1
3. C/EBP- P 19
4. Scr
5. Scr-P1
6. Scr-P19
7. P1
8. P19

PANC-1       Huh 7

ANTI-CANCER RNA APTAMERS

CROSS-REFERENCE TO RELATED APPLICATIONS

This applications is the national stage filing under U.S.C. 371 of international application number PCT/US2016/025351, filed Mar. 31, 2016, which claims the benefit of U.S. Provisional Application No. 62/141,156, filed Mar. 31, 2015, which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48440-568001WO_ST25.TXT, created Mar. 30, 2016, 5,419 bytes, machine format IBM-PC, MS-Windows operating system, is hereby incorporated by reference.

BACKGROUND OF THE INVENTION

Pancreatic ductal adenocarcinoma (PDAC) is the fourth most common cause of cancer death in the United States, accounting for 30,000 deaths yearly in the US[1]. Despite great efforts to improve treatment for patients with pancreatic cancer, limited progress has been made[2, 3]. Although much research has been conducted to develop improved systemic therapies for pancreatic cancer, gemcitabine as a single agent given postoperatively remains the current standard of care. Combinations with other chemotherapeutic drugs or biological agents given as a palliative setting for unresectable pancreatic cancer or adjuvant setting following resection have resulted in limited improvement[4-6]. The 5 year survival of patients with pancreatic cancer, despite numerous phase 3 trials, remains less than 5% after resection[7-10]. The majority of patients will present with either local or systemic recurrence within 2 years following resection and postoperative adjuvant chemotherapy[7-9]. Currently, the most effective single agent gemcitabine achieves an improved 1-year survival rate from 16 to 19%. The addition of Tarceva® (erlotinib) in a randomized study added a median of 11 days to overall survival[11, 12]. This limitation of conventional treatment is due to the profound resistance of PDAC cells towards anti-cancer drugs emerging from the efficient protection against chemotherapeutic drugs[13, 14]. Therefore, it is imperative to develop new therapeutic strategies for this devastating disease.

To overcome the current treatment obstacles, KRAS (V-Ki-ras2 Kirsten rat sarcoma viral oncogene homolog) has been appreciated as a therapeutic target in pancreatic cancer (PC). However, direct targeting KRAS or mutant forms of KRAS which role is well established in pancreatic carcinogenesis has failed in the clinic, assumed to be a undruggable target[15]. It also indicates that there is another mechanism underlying uniformly regardless of KRAS mutations; BxPC3 harbors wild-type KRAS, whereas other PDAC cell lines harbor mutated KRAS.

Short RNAs targeting to promoter regions of certain genes upregulates the expression at the transcriptional level without altering the genome in human cells, which is termed RNA activation (RNAa/saRNA)[16, 17]. Contrary to the antagonism of a specific target genes offered by siRNA, the activation of molecular targets is also crucial to control cancer gene expression effectively by the gain of function. The first saRNA targeting non-coding regulatory regions in gene promoters are E-cadherin, p21 and VEGF promoter[16]. In liver cancer, Reebye et. al. described that saRNA targeting CCAAT/enhancer-binding protein-α (C/EBPα), a transcriptional factor and a leucine zipper protein known to upregulate known to upregulate p21 which is an inhibitor of cell proliferation[18], decreases cell proliferation in HepG2 cells. In an in vivo cirrhotic model, intravenous injection of C/EBPα-saRNA decreased tumor burden[18]. The loss of the KDM6B gene encoding a histone demethylase, another tumor suppressor gene, inhibits transcriptional activation and enhances aggressiveness through downregulation of C/EBPα[19]. C/EBPα is silenced epigenetically by histone deacetylation and DNA methylation[20] in pancreatic cancer.

Aptamers identified using the Systematic Evolution of Ligands by EXponential enrichment (SELEX) as an in vitro selection strategy can adopt complex structures to bind targets with high affinities and specificities[21, 22]. Aptamers can be selected to recognize a wide variety of targets from small molecules to proteins and nucleic acids in cultured cells and whole organisms[23-28]. Due to the features of folding back into their natural conformation after denaturation, aptamers may keep their structures stably in the reducing condition[29]. RNA aptamers offer significant advantages compared to antibodies[29]. There is a need in the art for up-to-date therapeutic strategies and accurate delivery of therapeutics are imperative. Provided herein are compositions and methods addressing these and other needs in the art.

BRIEF SUMMARY OF THE INVENTION

Provided herein, inter alia, are novel nucleic acid compositions capable of binding to cell surface mitochondrial HSP70 (also referred to herein as mHSP70) on a cell and internalizing into the cell. The nucleic acid compositions provided herein are, for example, useful for the delivery of therapeutic and imaging agents into cells expressing cell surface mitochondrial HSP70. Further provided herein are methods of delivering a compound (e.g., nucleic acid compounds as provided herein, therapeutic compounds, diagnostic compounds) to a cell by allowing the compound to bind to cell surface mHSP70 on the cell and internalizing into the cell.

In one aspect, a compound including an RNA sequence having at least 80% sequence identity to SEQ ID NO:1 is provided, wherein the compound does not include an RNA sequence of SEQ ID NO:2, SEQ ID NO:3, SEQ ID NO:4, SEQ ID NO:5, SEQ ID NO:6 or SEQ ID NO:7.

In one aspect, a nucleic acid compound including an RNA sequence having at least 80% sequence identity to SEQ ID NO:1 is provided, wherein the nucleic acid compound does not include an RNA sequence of SEQ ID NO:2, SEQ ID NO:3, SEQ ID NO:4, SEQ ID NO:5, SEQ ID NO:6 or SEQ ID NO:7.

In another aspect, a pharmaceutical formulation including the nucleic acid compound as provided herein including embodiments thereof and a pharmaceutically acceptable excipient is provided.

In another aspect, the pharmaceutical formulation includes the nucleic acid compound as provided herein including embodiments thereof and a therapeutic agent.

In one aspect, a method of delivering a compound into a cell is provided. The method includes contacting a cell surface HSP70 (e.g. mHSP70) with a compound including an HSP70 (e.g. mHSP70) ligand moiety. The compound is allowed to pass into the cell thereby delivering the compound into the cell. The compound does not include a nucleic acid sequence of SEQ ID NO:2, SEQ ID NO:3, SEQ ID NO:4, SEQ ID NO:5, SEQ ID NO:6 or SEQ ID NO:7.

In another aspect, a method of treating cancer is provided. The method includes administering to a subject in need thereof an effective amount of the nucleic acid compound as provided herein (including embodiments thereof).

In another aspect, a method of treating cancer is provided. The method includes administering to a subject in need thereof an effective amount of an anticancer agent and a nucleic acid compound as provided herein including embodiments thereof.

BRIEF DESCRIPTION OF THE DRAWINGS

FIG. 1A-1G: Showing the secondary structure and pancreatic cancer specific internalization (FIG. 1A). Cartoon of the secondary structures of P19 (SEQ ID NO:2) and P1 (SEQ ID NO:4) are shown; aptamers were selected from randomized N40 RNA libraries and were predicted using the Mfold program. (FIG. 1B) Cy3-labeled RNAs were tested for binding to PANC-1 and NC as control cells by flow cytometry. Data represent the average of three replicated. Initial RNA library pool is shown as Library, P1 and P19. Cy3 labeled P19 and P1 incubation in. (FIG. 1C) Cy3-labeled RNAs (100 nM) was tested for internalization by confocal in negative cells, PANC-1 and MIA PaCa-2: Cy3-labeled RNA. (FIG. 1D) Cy3-labeled RNAs (100 nM) was tested for the internalization in primary pancreatic epithelial cells; Cy3-labeled RNA. (FIG. 1E) The representative images by histopathological screen in pancreatic cancer and normal pancreas. The samples were stained with Cy3 labeled aptamer P1 and P19 respectively and examined at 100× magnification. White arrow indicate that P19 binding to cancer region. Cy3-labeled RNA. (FIG. 1F) A total of 72 patients of pancreatic adenocarcinoma had undergone. The Correlation coefficient between P1 and P19 is 0.891. (FIG. 1G) The measurement of dissociation constant ($K_D$) was performed by flow cytometry using various concentrations (15.6-500 nM) of Cy3 labeled aptamers. Median fluorescence intensity (MFI) was measured and calculated using one site binding non-linear curve regression with a Graph Pad Prism.

(FIG. 2B) Flow cytometry analysis of P19 and P1 in T and B cells. Cy3-labeled RNAs were tested for binding to T and B cell isolated from human blood.

(FIG. 3A) PANC-1 cells were incubated with fluorescently labeled P19 RNA (200 nM) and increasing amounts (1 μM) of unlabeled each clone aptamers as competitors against the labeled RNA. The fluorescence intensity was quantified in the presence of increasing amounts of competitors using confocal microscopy and analyzed statistically. One-way ANOVA: P<0.05. (FIG. 3B) SDS-PAGE gel was used to run samples after retrieving target proteins.; (M) markers. Gel shift assays. Native PAGE gel was used to run. FIG. 3C (P19) and FIG. 3D (P1): The shifted band was observed in both P19 and P1. FIG. 3E and FIG. 3F SPR analysis. P19 (FIG. 3E) and P1 (FIG. 3F) labeled with biotin at the end of 3' were immobilized on SA chip. A BIAcore T100 was used to measure binding by surface plasmon resonance (SPR) technique.

(FIG. 4A) The internalization of conjugates in cells. Delivering moieties of saRNA-C/EBPa was labeled with Cy3 and incubated in cells. (FIG. 4B) Endosomal escapes. Cy3-labeled conjugates were incubated in Rab7 expressed cells. (FIG. 4C) Co-localization C/EBPa with RNA Pol II. Cy3 labeled with C/EBPα, RNA Pol II. Arrow indicated the co-localization of C/EBPa with RNA Pol II in nuclear. (FIG. 4D) Relative gene activation measurement by qPCR. The cells were grown with seeding at 1×10$^4$ cells in medium for 24 hrs. Total RNA was extracted and RNA extracts were reverse transcribed. The cDNA was then amplified for quantitative analysis of C/EBPα and GAPDH. (FIG. 4E) Detection of mRNA in live cells. The Arbitrary intensity unit of unit was measured by confocal and normalized. (FIG. 4F) The anti-proliferation assays were assessed in the P19 conjugates using WST-1.

FIG. 5A-5F. In vivo experiments. (FIG. 5A) The conjugates of P19 and P1 was injected via tail vein injection in Panc-1 engrafted mice. The conjugates were injected day 1, 3 and 5 for 3 or 4 weeks. Student t-test (unpaired, two-tailed) was used for statistical analysis. * t-test: P value<0.05. ** t-test: P value<0.01. (FIG. 5B) The photon was counter by I.V.I.S and signal changes were calculated in traceable xenoengrafted mice. (FIG. 5C) The representative images of the spectrum of IVIS 200 of each group. (FIG. 5D) Comparison of anti-tumor effect of C/EBPα-saRNA with gemcitabine in Panc-1 engrafted mice by tail vein injection. Tumor size was measured. * t-test: P value<0.05. (FIG. 5E) The tumor growth inhibition of gemcitabine-resistant ASPC-1 engrafted mice by tail vein injection. Signal changes were calculated. Metastasis to ascites was measured. * t-test: P value<0.05. (FIG. 5F) Comparison of cytotoxicity with gemcitabine. Hemoglobin, WBC, neutrophil and platelet were counted.

(FIG. 11A) Cartoon of the secondary structure of truncated P19 (SEQ ID NO:1) by M Fold. (FIG. 11B) The binding affinity of truncated P19. The measurement of dissociation constant ($K_D$) was performed by flow cytometry using various concentrations (15.6-500 nM) of Cy3 labeled aptamers. Median fluorescence intensity (MFI) was measured and calculated using one site binding non-linear curve regression with a Graph Pad Prism. (FIG. 11C) The internalization of truncated P19 in PANC-1 and AsPC-1. Cy3-labeled RNAs (100 nM) was tested for internalization by confocal. Cy3-labeled RNA and Hoechst 33342 staining are shown. (FIG. 11D) The internalization of truncated P19 in other type of cancer. Cy3-labeled RNAs (200 nM) was tested for internalization by confocal. Cy3-labeled RNA and Hoechst 33342 staining are shown.

(FIG. 13A) Cartoon of the secondary structures of P19 (SEQ ID NO:2) and P1 (SEQ ID NO:4) are shown, aptamers were selected from randomized N40 RNA libraries and were predicted using the Mfold software. (FIG. 13B) Cy3-labeled P19 and P1 aptamers were assessed for binding efficiency by flow cytometry in PANC-1 and control Huh7 cells. The data show the measurements of positively stained cells and representative of triplicates. (FIG. 13C) The pancreatic cell lines PANC-1, AsPC-1, MIA PaCa and Capan-1 were treated with 100 nM of the Cy3-labeled P19 and P1 aptamer and analysed by confocal microscopy. All of the pancreatic lines showed punctate regions of Cy3 labeling. Non pancreatic lines including Huh7, HepG2, MCF7 and PC3 cells were also treated with 100 nM of Cy3-labeled P19 and P1 aptamers. No Cy3 signal was observed. Blue: Hoechst 33342. Scale bar: 10 μm (FIG. 13D) Normal primary pancreatic cells were treated with 100 nM Cy3-labeled aptamers and imaged by confocal microscopy. Blue: Hoechst 33342. Scale bar: 10 μm (FIG. 13E) Flow cytometry analysis of normal T and B cells treated with Cy3-labeled P19 and P1 aptamers. (FIG. 13F and FIG. 13G) The dissociation constant ($K_D$) was measured by flow cytometry using increasing concentrations of Cy3-labeled aptamers (from 15.6 to 500 nM). Mean fluorescence intensity (MFI) was measured and calculated using a one-site binding model for non-linear regression.

(FIG. 14A) Cy3-labeled P19- or P1-conjugated C/EBPα-saRNAs were incubated with PANC-1 cells. Red: Cy3-labeled RNA, Blue: Hoechst 33342. (FIG. 14B) Relative transcript expression (qPCR) for C/EBPα mRNA and (FIG. 14C) p21 mRNA was quantified by real-time PCR. CEBPA expression increased 5 fold (p=0.029) and p21 increase 57.6 fold (p=0.033) by P19-CEBPα-saRNA conjugated aptamer or 1.29 fold (p=0.015) and 1.4 fold (p=0.026) respectively by P1-CEBPα-saRNA conjugated aptamer. (T-test with Welch's correction at 95% confidence interval). (FIG. 14D) A WST-1 cell proliferation assay was performed in PANC-1 cells. At 96 hours, only 22.9% of total cells were proliferating following treatment with P19-CEBPα-saRNA and 28% of total cells proliferation following P1-C/EBPα-saRNA. Both P19-Scramble-saRNA and P1-Scramble-saRNA demonstrated cytostatic effects on the cells. (FIG. 14E) Western blot analysis was carried out in PANC-1 cells treated with P19- or P1-conjugated C/EBPα-saRNA or scrambled saRNA aptamers. Membranes were probed with anti-C/EBPα and anti-actin (control). Band intensity from three representative blots were analyses (lower panel). P19 and P1-C/EBPα-saRNA treatment induced a 3-fold increase in CEBPA signal relative to untreated cells. P19 and P1-scramble conjugate treatment both induced a 2-fold increase in CEBPA signal (FIG. 15A) P19- and P1-conjugated C/EBPα-saRNA aptamers were injected in PANC-1 engrafted mice via tail vein injection at 100 and 250 pmol. Tumor size was calculated by the formula 0.52×length×width×width. Data are presented as the mean±SD (n=4 each group) (FIG. 15B).

(FIG. 18B) KRAS mRNA was quantified by real-time PCR. KRAS expression decreased 40% at 72 hours at 200 nM by tP19-KRAS-335 siRNA. Both tP19-KRAS-234 and tP19-KRAS-335 silenced KRAS mRNA transcripts. ΔΔCt method was used to calculate gene expression. HPRT was used to normalization. (FIG. 18C) PDL1 mRNA was quantified by real-time PCR. Before to make the conjugate with tP19, siPDL1 was designed and tested the silencing effect in PANC-1. ΔΔCt method was used to calculate gene expression. HPRT was used to normalization.

DETAILED DESCRIPTION OF THE INVENTION

Definitions

Figure 1F:
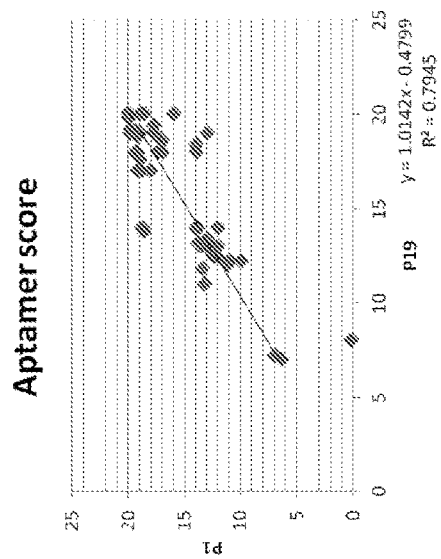

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$N(R)('R"—NSO$_2$R'), —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", NR"C(O)$_2$R', NRC(NR'R")=NR'", S(O)R', —S(O)$_2$R', —S(O)$_2$N(R')(R", —NRSO$_2$R'), —CN, —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{14}$-substituted or unsubstituted alkyl, a plurality of $R^{14}$ substituents may be attached to the alkyl moiety wherein each $R^{14}$ substituent is optionally different. Where an R-substituted moiety is substituted with a plurality R substituents, each of the R-substituents may be differentiated herein using a prime symbol (') such as R', R", etc. For example, where a moiety is $R^{14}$-substituted or unsubstituted alkyl, and the moiety is substituted with a plurality of $R^{14}$ substituents, the plurality of $R^{14}$ substituents may be differentiated as $R^{14'}$, $R^{14''}$, $R^{14'''}$, etc. In some embodiments, the plurality of R substituents is 3. In some embodiments, the plurality of R substituents is 2.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where variables s and d are independently integers of from 0 to 3, and X' is —O—, —NR=—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, heteroaryl, substituted with at least one substituent selected from:
(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

As used herein, the term "conjugate" refers to the association between atoms or molecules. The association can be direct or indirect. For example, a conjugate between a nucleic acid (e.g., ribonucleic acid) and a compound moiety as provided herein can be direct, e.g., by covalent bond, or indirect, e.g., by non-covalent bond. Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. Thus, the nucleic acid acids can be attached to a compound moiety through its backbone. Optionally, the ribonucleic acid includes one or more reactive moieties, e.g., an amino acid reactive moiety, that facilitates the interaction of the ribonucleic acid with the compound moiety.

Useful reactive moieties or functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Chemical synthesis of compositions by joining small modular units using conjugate ("click") chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stöckmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the proteins described herein. By way of example, the nucleic acids can include a vinyl sulfone or other reactive moiety. Optionally, the nucleic acids can include a reactive moiety having the formula S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research,* Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

The term "aptamer" as provided herein refers to oligonucleotides (e.g. short oligonucleotides or deoxyribonucleotides), that bind (e.g. with high affinity and specificity) to proteins, peptides, and small molecules. Aptamers may be RNA. Aptamers may have secondary or tertiary structure and, thus, may be able to fold into diverse and intricate molecular structures. Aptamers can be selected in vitro from very large libraries of randomized sequences by the process of systemic evolution of ligands by exponential enrichment (SELEX as described in Ellington A D, Szostak J W (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLoS ONE 5(12):e15004). Applying the SELEX and the SOMAmer technology includes for instance adding functional groups that mimic amino acid side chains to expand the aptamer's chemical diversity. As a result high affinity aptamers for a protein may be enriched and identified. Aptamers may exhibit many desirable properties for targeted drug delivery, such as ease of selection and synthesis, high binding affinity and specificity, low immunogenicity, and versatile synthetic accessibility. Anti-cancer agents (e.g. chemotherapy drugs, toxins, and siRNAs) may be successfully delivered to cancer cells in vitro using apatmers.

An "antisense nucleic acid" as referred to herein is a nucleic acid (e.g. DNA or RNA molecule) that is complementary to at least a portion of a specific target nucleic acid (e.g. an mRNA translatable into a protein) and is capable of reducing transcription of the target nucleic acid (e.g. mRNA from DNA) or reducing the translation of the target nucleic acid (e.g. mRNA) or altering transcript splicing (e.g. single stranded morpholino oligo). See, e.g., Weintraub, *Scientific American,* 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid (e.g. target mRNA). In embodiments, the antisense nucleic acid hybridizes to the target nucleic acid sequence (e.g. mRNA) under stringent hybridization conditions. In embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbonemodified nucleotides.

In the cell, the antisense nucleic acids hybridize to the corresponding mRNA, forming a double-stranded molecule. The antisense nucleic acids interfere with the translation of the mRNA, since the cell will not translate an mRNA that is double-stranded. The use of antisense methods to inhibit the in vitro translation of genes is well known in the art (Marcus-Sakura, *Anal. Biochem.,* 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

A "siRNA," "small interfering RNA," "small RNA," or "RNAi" as provided herein, refers to a nucleic acid that forms a double stranded RNA, which double stranded RNA has the ability to reduce or inhibit expression of a gene or target gene when present in the same cell as the gene or target gene. The complementary portions of the nucleic acid that hybridize to form the double stranded molecule typically have substantial or complete identity. In one embodiment, a siRNA or RNAi is a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

A "saRNA," or "small activating RNA" as provided herein refers to a nucleic acid that forms a double stranded RNA, which double stranded RNA has the ability to increase or activate expression of a gene or target gene when present in the same cell as the gene or target gene. The complementary portions of the nucleic acid that hybridize to form the double stranded molecule typically have substantial or complete identity. In one embodiment, a saRNA is a nucleic acid that has substantial or complete identity to a target gene and forms a double stranded saRNA. Typically, the nucleic acid is at least about 15-50 nucleotides in length (e.g., each complementary sequence of the double stranded saRNA is 15-50 nucleotides in length, and the double stranded saRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

For specific proteins described herein (e.g., mHSP70), the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "HSP70" refers to the family of approximately 70 kilo Dalton heat shock proteins as well-known in the art. In embodiment, the HSP70 is mHSP70. The term "mHSP70" as provided herein includes any of the mitochondrial HSP70 (mHSP70) protein naturally occurring forms, homologs or variants that maintain the activity of mHSP70 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the mHSP70 protein is the protein as identified by the NCBI sequence reference GI:24234688. In embodiments, the mHSP70 protein is the protein as identified by the NCBI sequence reference GI:24234688, homolog or functional fragment thereof mHSP70 may also be referred to herein as mortalin, CSA, GRP-75, GRP75, HEL-S-124m, HSPA9B, MOT, MOT2, MTHSP75 or PBP74.

The term "C/EBPa" or "C/EBPalpha" as provided herein includes any of the CCAAT (cytosine-cytosine-adenosine-adensoine-thymidine)/enhancer-binding protein alpha (C/EBPa) naturally occurring forms, homologs or variants that maintain the transcription factor activity of C/EBPalpha (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the C/EBPalpha protein is the protein as identified by the NCBI sequence reference GI:551894998. In embodiments, the C/EBPalpha protein is the protein as identified by the NCBI sequence reference GI:551894998, homolog or functional fragment thereof. In embodiments, the C/EBPalpha protein is encoded by a nucleic acid sequence corresponding to Gene ID: GI:551894997.

The term "KRAS" or "KRAS protein" as provided herein includes any of the GTPase KRas protein, also known as V-Ki-ras2 Kirsten rat sarcoma viral oncogene homolog, naturally occurring forms, homologs or variants that maintain the transcription factor activity of KRAS (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the KRAS protein is the protein as identified by the UniProt sequence reference P01116.

The term "PDL-1" as provided herein includes any of the recombinant or naturally-occurring forms of the protein programmed cell death ligand 1 (PD-L1) or variants or homologs thereof that maintain PDL-1 protein activity (e.g. within at least 50%, 80%, 90%, 95%, 96%, 97%, 98%, 99% or 100% activity compared to PDL-1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PDL-1 polypeptide. In embodiments, PDL-1 is the protein as identified by the NCBI sequence reference GI:390979639, homolog or functional fragment thereof.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), or adrenocortical suppressant (e.g., mitotane, aminoglutethimide), epipodophyllotoxins (e.g., etoposide).

Further examples of anti-cancer agents include, but are not limited to, antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein kinase C inhibitors, protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the nucleic acid compound described herein can be co-administered with or covalently attached to conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, anti-PD-1 and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y or $^{131}$I, etc.).

In a further embodiment, the nucleic acid compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

Antibodies are large, complex molecules (molecular weight of ~450,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

A "therapeutic antibody" as provided herein refers to any antibody or functional fragment thereof that is used to treat cancer, autoimmune diseases, transplant rejection, cardiovascular disease or other diseases or conditions such as those described herein. Non-limiting examples of therapeutic antibodies include murine antibodies, murinized or humanized chimera antibodies or human antibodies including, but not limited to, Erbitux (cetuximab), ReoPro (abciximab), Simulect (basiliximab), Remicade (infliximab); Orthoclone OKT3 (muromonab-CD3); Rituxan (rituximab), Bexxar (tositumomab) Humira (adalimumab), Campath (alemtuzumab), Simulect (basiliximab), Avastin (bevacizumab), Cimzia (certolizumab pegol), Zenapax (daclizumab), Soliris (eculizumab), Raptiva (efalizumab), Mylotarg (gemtuzumab), Zevalin (ibritumomab tiuxetan), Tysabri (natalizumab), Xolair (omalizumab), Synagis (palivizumab), Vectibix (panitumumab), Lucentis (ranibizumab), and Herceptin (trastuzumab).

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery"in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule (e.g., nucleic acid, small molecule), capable of binding to a polypeptide expressed on the surface of (e.g., receptor) or inside a cell.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Disease" or "condition" refer to a state of being or health status of a patient or subject capable of being treated with a compound, pharmaceutical composition, or method provided herein. In embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma), an infectious disease (e.g., HIV infection), an inflammatory disease (e.g., rheumatoid arthritis) or a metabolic disease (e.g., diabetes). In embodiments, the disease is a disease related to (e.g. caused by) an aberrant activity of HSP70 (e.g. mHSP70), HSP70 (e.g. mHSP70) phosphorylation, or HSP70 (e.g. mHSP70) pathway activity, or pathway activated by HSP70. In some embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma).

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) or viral disease (e.g., HIV infection associated disease)) is caused by (in whole or in part), or a symptom of the disease is caused by (in whole or in part) the substance or substance activity or function.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a nucleic acid compound as described herein and a cell (e.g., cancer cell).

Nucleic Acid Compounds

The compounds (e.g., nucleic acid compounds) provided herein, including embodiments thereof, are, inter alia, capable of binding mitochondrial HSP70 (mHSP70) on a cell and internalizing into the cell. mHSP70 is expressed within and present on the surface of a broad variety of different cancer cells (e.g., pancreatic cancer, liver cancer, prostate cancer). Therefore, the compounds (e.g., nucleic acid compounds) provided herein, including embodiments thereof, may be used to deliver therapeutic or diagnostic molecules into a mHSP70-expressing cancer cell. The therapeutic or diagnostic molecule may form part of the compound (e.g., nucleic acid compound) provided herein including embodiments thereof. Where the therapeutic or diagnostic molecule forms part (e.g., through covalent attachment) of the compound (e.g., nucleic acid compound) provided herein, including embodiments thereof, the therapeutic or diagnostic molecule is referred to as a "compound moiety" (e.g., therapeutic moiety, imaging moiety). Alternatively, the therapeutic or diagnostic molecule may not form part of the compound (e.g., nucleic acid compound) provided herein, including embodiments thereof, but may be independently internalized by a mHSP70-expressing cell upon binding of a compound (e.g., nucleic acid compound) provided herein to mHSP70 on said cell. Where the therapeutic or diagnostic molecule does not form part of the compound (e.g., nucleic acid compound) provided herein, the molecule is referred to as a "second compound." The compounds (e.g., nucleic acid compounds) provided herein including embodiments thereof provide highly specific and efficient means for targeted cancer drug delivery and molecular imaging.

In one aspect, a compound including an RNA sequence having at least 80% sequence identity to SEQ ID NO:1 is provided, wherein the compound does not include an RNA sequence of SEQ ID NO:2, SEQ ID NO:3, SEQ ID NO:4, SEQ ID NO:5, SEQ ID NO:6 or SEQ ID NO:7. In embodiments, the compound is a nucleic acid compound, a peptide, a small molecule or an antibody or functional fragment thereof.

In one aspect, a nucleic acid compound including an RNA sequence having at least 80% sequence identity to SEQ ID NO:1 is provided, wherein the nucleic acid compound does not include an RNA sequence of SEQ ID NO:2, SEQ ID NO:3, SEQ ID NO:4, SEQ ID NO:5, SEQ ID NO:6 or SEQ ID NO:7. Where the RNA sequence has at least 80% (80% or more) sequence identity to SEQ ID NO:1, the RNA sequence may have 80%, 85%, 90%, 91%, 92%, 93%, 94%, 95%, 96%, 97%, 98%, 99% or 100% sequence identity to SEQ ID NO:1. In embodiments, the RNA sequence has at least 80% (80% or more) sequence identity to a nucleic acid that hybridizes to a SEQ ID NO:1.

In embodiments, the RNA sequence has at least 80% sequence identity to SEQ ID NO:1. In embodiments, the RNA sequence has at least 85% sequence identity to SEQ ID NO:1 In embodiments, the RNA sequence has at least 90% sequence identity to SEQ ID NO:1. In embodiments, the RNA sequence has at least 95% sequence identity to SEQ ID NO:1. In embodiments, the RNA sequence has at least 98% sequence identity to SEQ ID NO:1. In embodiments, the RNA sequence has at least 80%, 85%, 90%, 95%, 96%, 97%, 98%, 99% or 100% sequence identity across the whole sequence of to SEQ ID NO:1. In embodiments, the RNA sequence has at least 80%, 85%, 90%, 95%, 96%, 97%, 98%, 99% or 100% sequence identity across 10, 15, 20, 25, 26, 27, or 28 continuous nucleotides of SEQ ID NO:1.

In embodiments, the RNA sequence is less than 88 (87 or less) nucleotides in length. Where the RNA sequence is less than 88 (87 or less) nucleotides in length the RNA sequence is 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In embodiments, the RNA sequence is less than 80 nucleotides in length. In embodiments, the RNA sequence is less than 70 nucleotides in length. In embodiments, the RNA sequence is less than 60 nucleotides in length. In embodiments, the RNA sequence is less than 50 nucleotides in length. In embodiments, the RNA sequence is less than 40 nucleotides in length. In embodiments, the RNA sequence is less than 30 nucleotides in length.

In embodiments, the RNA sequence is between 20 and 87 nucleotides in length. In embodiments, the RNA sequence is between 25 and 87 nucleotides in length. In embodiments, the RNA sequence is between 30 and 87 nucleotides in length. In embodiments, the RNA sequence is between 35 and 87 nucleotides in length. In embodiments, the RNA sequence is between 40 and 87 nucleotides in length. In embodiments, the RNA sequence is between 45 and 87 nucleotides in length. In embodiments, the RNA sequence is between 50 and 87 nucleotides in length. In embodiments, the RNA sequence is between 55 and 87 nucleotides in length. In embodiments, the RNA sequence is between 60 and 87 nucleotides in length. In embodiments, the RNA sequence is between 65 and 87 nucleotides in length. In embodiments, the RNA sequence is between 70 and 87 nucleotides in length. In embodiments, the RNA sequence is between 75 and 87 nucleotides in length. In embodiments, the RNA sequence is between 80 and 87 nucleotides in length. In embodiments, the RNA sequence is between 85 and 87 nucleotides in length.

In embodiments, the RNA sequence is between 20 and 85 nucleotides in length. In embodiments, the RNA sequence is between 25 and 85 nucleotides in length. In embodiments, the RNA sequence is between 30 and 85 nucleotides in length. In embodiments, the RNA sequence is between 35 and 85 nucleotides in length. In embodiments, the RNA sequence is between 40 and 85 nucleotides in length. In embodiments, the RNA sequence is between 45 and 85 nucleotides in length. In embodiments, the RNA sequence is between 50 and 85 nucleotides in length. In embodiments, the RNA sequence is between 55 and 85 nucleotides in length. In embodiments, the RNA sequence is between 60 and 85 nucleotides in length. In embodiments, the RNA sequence is between 65 and 85 nucleotides in length. In embodiments, the RNA sequence is between 70 and 85 nucleotides in length. In embodiments, the RNA sequence is between 75 and 85 nucleotides in length. In embodiments, the RNA sequence is between 80 and 85 nucleotides in length.

In embodiments, the RNA sequence is between 20 and 80 nucleotides in length. In embodiments, the RNA sequence is between 25 and 80 nucleotides in length. In embodiments, the RNA sequence is between 30 and 80 nucleotides in length. In embodiments, the RNA sequence is between 35 and 80 nucleotides in length. In embodiments, the RNA sequence is between 40 and 80 nucleotides in length. In embodiments, the RNA sequence is between 45 and 80 nucleotides in length. In embodiments, the RNA sequence is between 50 and 80 nucleotides in length. In embodiments, the RNA sequence is between 55 and 80 nucleotides in length. In embodiments, the RNA sequence is between 60 and 80 nucleotides in length. In embodiments, the RNA sequence is between 65 and 80 nucleotides in length. In embodiments, the RNA sequence is between 70 and 80 nucleotides in length. In embodiments, the RNA sequence is between 75 and 80 nucleotides in length.

In embodiments, the RNA sequence is between 20 and 75 nucleotides in length. In embodiments, the RNA sequence is between 25 and 75 nucleotides in length. In embodiments, the RNA sequence is between 30 and 75 nucleotides in length. In embodiments, the RNA sequence is between 35 and 75 nucleotides in length. In embodiments, the RNA sequence is between 40 and 75 nucleotides in length. In embodiments, the RNA sequence is between 45 and 75 nucleotides in length. In embodiments, the RNA sequence is between 50 and 75 nucleotides in length. In embodiments, the RNA sequence is between 55 and 75 nucleotides in length. In embodiments, the RNA sequence is between 60 and 75 nucleotides in length. In embodiments, the RNA sequence is between 65 and 75 nucleotides in length. In embodiments, the RNA sequence is between 70 and 75 nucleotides in length.

In embodiments, the RNA sequence is between 20 and 70 nucleotides in length. In embodiments, the RNA sequence is between 25 and 70 nucleotides in length. In embodiments, the RNA sequence is between 30 and 70 nucleotides in length. In embodiments, the RNA sequence is between 35 and 70 nucleotides in length. In embodiments, the RNA sequence is between 40 and 70 nucleotides in length. In embodiments, the RNA sequence is between 45 and 70 nucleotides in length. In embodiments, the RNA sequence is between 50 and 70 nucleotides in length. In embodiments, the RNA sequence is between 55 and 70 nucleotides in length. In embodiments, the RNA sequence is between 60 and 70 nucleotides in length. In embodiments, the RNA sequence is between 65 and 70 nucleotides in length.

In embodiments, the RNA sequence is between 20 and 65 nucleotides in length. In embodiments, the RNA sequence is between 25 and 65 nucleotides in length. In embodiments, the RNA sequence is between 30 and 65 nucleotides in length. In embodiments, the RNA sequence is between 35 and 65 nucleotides in length. In embodiments, the RNA sequence is between 40 and 65 nucleotides in length. In embodiments, the RNA sequence is between 45 and 65 nucleotides in length. In embodiments, the RNA sequence is between 50 and 65 nucleotides in length. In embodiments, the RNA sequence is between 55 and 65 nucleotides in length. In embodiments, the RNA sequence is between 60 and 65 nucleotides in length.

In embodiments, the RNA sequence is between 20 and 60 nucleotides in length. In embodiments, the RNA sequence is between 25 and 60 nucleotides in length. In embodiments, the RNA sequence is between 30 and 60 nucleotides in length. In embodiments, the RNA sequence is between 35 and 60 nucleotides in length. In embodiments, the RNA sequence is between 40 and 60 nucleotides in length. In embodiments, the RNA sequence is between 45 and 60 nucleotides in length. In embodiments, the RNA sequence is between 50 and 60 nucleotides in length. In embodiments, the RNA sequence is between 55 and 60 nucleotides in length.

In embodiments, the RNA sequence is between 20 and 55 nucleotides in length. In embodiments, the RNA sequence is between 25 and 55 nucleotides in length. In embodiments, the RNA sequence is between 30 and 55 nucleotides in length. In embodiments, the RNA sequence is between 35 and 55 nucleotides in length. In embodiments, the RNA sequence is between 40 and 55 nucleotides in length. In embodiments, the RNA sequence is between 45 and 55 nucleotides in length. In embodiments, the RNA sequence is between 50 and 55 nucleotides in length. In embodiments, the RNA sequence is between 20 and 50 nucleotides in length. In embodiments, the RNA sequence is between 25 and 50 nucleotides in length. In embodiments, the RNA sequence is between 30 and 50 nucleotides in length. In embodiments, the RNA sequence is between 35 and 50 nucleotides in length. In embodiments, the RNA sequence is between 40 and 50 nucleotides in length. In embodiments, the RNA sequence is between 45 and 50 nucleotides in length.

In embodiments, the RNA sequence is between 20 and 45 nucleotides in length. In embodiments, the RNA sequence is between 25 and 45 nucleotides in length. In embodiments, the RNA sequence is between 30 and 45 nucleotides in length. In embodiments, the RNA sequence is between 35 and 45 nucleotides in length. In embodiments, the RNA sequence is between 40 and 45 nucleotides in length. In embodiments, the RNA sequence is between 20 and 40 nucleotides in length. In embodiments, the RNA sequence is between 25 and 40 nucleotides in length. In embodiments, the RNA sequence is between 30 and 40 nucleotides in length. In embodiments, the RNA sequence is between 35 and 40 nucleotides in length. In embodiments, the RNA sequence is between 20 and 35 nucleotides in length. In embodiments, the RNA sequence is between 25 and 35 nucleotides in length. In embodiments, the RNA sequence is between 30 and 35 nucleotides in length. In embodiments, the RNA sequence is between 20 and 30 nucleotides in length. In embodiments, the RNA sequence is between 25 and 30 nucleotides in length. In embodiments, the RNA sequence is between 20 and 25 nucleotides in length.

In embodiments, the RNA sequence includes the sequence of SEQ ID NO:1. In embodiments, the RNA sequence is SEQ ID NO:1. In embodiments, the RNA sequence is an aptamer. In embodiments, the RNA sequence is 28 nucleotides in length.

In embodiments, the RNA sequence has at least 80% sequence identity to SEQ ID NO:1 and is less than 88 nucleotides in length. In embodiments, the RNA sequence has at least 80% sequence identity to SEQ ID NO:1 and is less than 80 nucleotides in length. In embodiments, the RNA sequence has at least 80% sequence identity to SEQ ID NO:1 and is less than 70 nucleotides in length. In embodiments, the RNA sequence has at least 80% sequence identity to SEQ ID NO:1 and is less than 60 nucleotides in length. In embodiments, the RNA sequence has at least 80% sequence identity to SEQ ID NO:1 and is less than 50 nucleotides in length. In embodiments, the RNA sequence has at least 80% sequence identity to SEQ ID NO:1 and is less than 40 nucleotides in length. In embodiments, the RNA sequence has at least 80% sequence identity to SEQ ID NO:1 and is less than 30 nucleotides in length. In embodiments, the RNA sequence has at least 80% sequence identity to SEQ ID NO:1 and is 28 nucleotides in length.

In embodiments, the RNA sequence has at least 85% sequence identity to SEQ ID NO:1 and is less than 88 nucleotides in length. In embodiments, the RNA sequence has at least 85% sequence identity to SEQ ID NO:1 and is less than 80 nucleotides in length. In embodiments, the RNA sequence has at least 85% sequence identity to SEQ ID NO:1 and is less than 70 nucleotides in length. In embodiments, the RNA sequence has at least 85% sequence identity to SEQ ID NO:1 and is less than 60 nucleotides in length. In embodiments, the RNA sequence has at least 85% sequence identity to SEQ ID NO:1 and is less than 50 nucleotides in length. In embodiments, the RNA sequence has at least 85% sequence identity to SEQ ID NO:1 and is less than 40 nucleotides in length. In embodiments, the RNA sequence has at least 85% sequence identity to SEQ ID NO:1 and is less than 30 nucleotides in length. In embodiments, the RNA sequence has at least 85% sequence identity to SEQ ID NO:1 and is 28 nucleotides in length.

In embodiments, the RNA sequence has at least 90% sequence identity to SEQ ID NO:1 and is less than 88 nucleotides in length. In embodiments, the RNA sequence has at least 90% sequence identity to SEQ ID NO:1 and is less than 80 nucleotides in length. In embodiments, the RNA sequence has at least 90% sequence identity to SEQ ID NO:1 and is less than 70 nucleotides in length. In embodiments, the RNA sequence has at least 90% sequence identity to SEQ ID NO:1 and is less than 60 nucleotides in length. In embodiments, the RNA sequence has at least 90% sequence identity to SEQ ID NO:1 and is less than 50 nucleotides in length. In embodiments, the RNA sequence has at least 90% sequence identity to SEQ ID NO:1 and is less than 40 nucleotides in length. In embodiments, the RNA sequence has at least 90% sequence identity to SEQ ID NO:1 and is less than 30 nucleotides in length. In embodiments, the RNA sequence has at least 90% sequence identity to SEQ ID NO:1 and is 28 nucleotides in length.

In embodiments, the RNA sequence has at least 95% sequence identity to SEQ ID NO:1 and is less than 88 nucleotides in length. In embodiments, the RNA sequence has at least 95% sequence identity to SEQ ID NO:1 and is less than 80 nucleotides in length. In embodiments, the RNA sequence has at least 95% sequence identity to SEQ ID NO:1 and is less than 70 nucleotides in length. In embodiments, the RNA sequence has at least 95% sequence identity to SEQ ID NO:1 and is less than 60 nucleotides in length. In embodiments, the RNA sequence has at least 95% sequence identity to SEQ ID NO:1 and is less than 50 nucleotides in length. In embodiments, the RNA sequence has at least 95% sequence identity to SEQ ID NO:1 and is less than 40 nucleotides in length. In embodiments, the RNA sequence has at least 95% sequence identity to SEQ ID NO:1 and is less than 30 nucleotides in length. In embodiments, the RNA sequence has at least 95% sequence identity to SEQ ID NO:1 and is 28 nucleotides in length.

In embodiments, the RNA sequence has at least 98% sequence identity to SEQ ID NO:1 and is less than 88 nucleotides in length. In embodiments, the RNA sequence has at least 98% sequence identity to SEQ ID NO:1 and is less than 80 nucleotides in length. In embodiments, the RNA sequence has at least 98% sequence identity to SEQ ID NO:1 and is less than 70 nucleotides in length. In embodiments, the RNA sequence has at least 98% sequence identity to SEQ ID NO:1 and is less than 60 nucleotides in length. In embodiments, the RNA sequence has at least 98% sequence identity to SEQ ID NO:1 and is less than 50 nucleotides in length. In embodiments, the RNA sequence has at least 98% sequence identity to SEQ ID NO:1 and is less than 40 nucleotides in length. In embodiments, the RNA sequence has at least 98% sequence identity to SEQ ID NO:1 and is less than 30 nucleotides in length. In embodiments, the RNA sequence has at least 98% sequence identity to SEQ ID NO:1 and is 28 nucleotides in length.

In embodiments, the RNA sequence is less than 88 (87 or less) nucleotides in length. Where the RNA sequence is less than 88 (87 or less) nucleotides in length the RNA sequence is 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In embodiments, the RNA sequence is less than 80 nucleotides in length. In embodiments, the RNA sequence is less than 70 nucleotides in length. In embodiments, the RNA sequence is less than 60 nucleotides in length. In embodiments, the RNA sequence is less than 50 nucleotides in length. In embodiments, the RNA sequence is less than 40 nucleotides in length. In embodiments, the RNA sequence is less than 30 nucleotides in length.

In embodiments, the nucleic acid compound does not include an RNA sequence having about 98% sequence identity to SEQ ID NO:2, SEQ ID NO:3, SEQ ID NO:4, SEQ ID NO:5, SEQ ID NO:6 or SEQ ID NO:7. In embodiments, the nucleic acid compound does not include an RNA sequence having about 98% sequence identity to SEQ ID NO:2. In embodiments, the nucleic acid compound does not include an RNA sequence having about 98% sequence identity to SEQ ID NO:3. In embodiments, the nucleic acid compound does not include an RNA sequence having about 98% sequence identity to SEQ ID NO:4. In embodiments, the nucleic acid compound does not include an RNA sequence having about 98% sequence identity to SEQ ID NO:5. In embodiments, the nucleic acid compound does not include an RNA sequence having about 98% sequence identity to SEQ ID NO:6. In embodiments, the nucleic acid compound does not include an RNA sequence having about 98% sequence identity to SEQ ID NO:7.

In embodiments, the nucleic acid compound does not include an RNA sequence having about 95% sequence identity to SEQ ID NO:2, SEQ ID NO:3, SEQ ID NO:4, SEQ ID NO:5, SEQ ID NO:6 or SEQ ID NO:7. In embodiments, the nucleic acid compound does not include an RNA sequence having about 95% sequence identity to SEQ ID NO:2. In embodiments, the nucleic acid compound does not include an RNA sequence having about 95% sequence identity to SEQ ID NO:3. In embodiments, the nucleic acid compound does not include an RNA sequence having about 95% sequence identity to SEQ ID NO:4. In embodiments, the nucleic acid compound does not include an RNA sequence having about 95% sequence identity to SEQ ID NO:5. In embodiments, the nucleic acid compound does not include an RNA sequence having about 95% sequence identity to SEQ ID NO:6. In embodiments, the nucleic acid compound does not include an RNA sequence having about 95% sequence identity to SEQ ID NO:7.

In embodiments, the nucleic acid compound does not include an RNA sequence having about 90% sequence identity to SEQ ID NO:2, SEQ ID NO:3, SEQ ID NO:4, SEQ ID NO:5, SEQ ID NO:6 or SEQ ID NO:7. In embodiments, the nucleic acid compound does not include an RNA sequence having about 90% sequence identity to SEQ ID NO:2. In embodiments, the nucleic acid compound does not include an RNA sequence having about 90% sequence identity to SEQ ID NO:3. In embodiments, the nucleic acid compound does not include an RNA sequence having about 90% sequence identity to SEQ ID NO:4. In embodiments, the nucleic acid compound does not include an RNA sequence having about 90% sequence identity to SEQ ID NO:5. In embodiments, the nucleic acid compound does not include an RNA sequence having about 90% sequence identity to SEQ ID NO:6. In embodiments, the nucleic acid compound does not include an RNA sequence having about 90% sequence identity to SEQ ID NO:7.

In embodiments, the nucleic acid compound does not include an RNA sequence having about 85% sequence identity to SEQ ID NO:2, SEQ ID NO:3, SEQ ID NO:4, SEQ ID NO:5, SEQ ID NO:6 or SEQ ID NO:7. In embodiments, the nucleic acid compound does not include an RNA sequence having about 85% sequence identity to SEQ ID NO:2. In embodiments, the nucleic acid compound does not include an RNA sequence having about 85% sequence identity to SEQ ID NO:3. In embodiments, the nucleic acid compound does not include an RNA sequence having about 85% sequence identity to SEQ ID NO:4. In embodiments, the nucleic acid compound does not include an RNA sequence having about 85% sequence identity to SEQ ID NO:5. In embodiments, the nucleic acid compound does not include an RNA sequence having about 85% sequence identity to SEQ ID NO:6. In embodiments, the nucleic acid compound does not include an RNA sequence having about 85% sequence identity to SEQ ID NO:7.

In embodiments, the nucleic acid compound does not include an RNA sequence having about 80% sequence identity to SEQ ID NO:2, SEQ ID NO:3, SEQ ID NO:4, SEQ ID NO:5, SEQ ID NO:6 or SEQ ID NO:7. In embodiments, the nucleic acid compound does not include an RNA sequence having about 80% sequence identity to SEQ ID NO:2. In embodiments, the nucleic acid compound does not include an RNA sequence having about 80% sequence identity to SEQ ID NO:3. In embodiments, the nucleic acid compound does not include an RNA sequence having about 80% sequence identity to SEQ ID NO:4. In embodiments, the nucleic acid compound does not include an RNA sequence having about 80% sequence identity to SEQ ID NO:5. In embodiments, the nucleic acid compound does not include an RNA sequence having about 80% sequence identity to SEQ ID NO:6. In embodiments, the nucleic acid compound does not include an RNA sequence having about 80% sequence identity to SEQ ID NO:7.

In embodiments, the nucleic acid compound does not include an RNA sequence having about 80%, 85%, 90%, 95%, 98% or 100% sequence identity across the whole sequence of SEQ ID NO:2, SEQ ID NO:3, SEQ ID NO:4, SEQ ID NO:5, SEQ ID NO:6 or SEQ ID NO:7. In embodiments, the nucleic acid compound does not include an RNA sequence having about 80%, 85%, 90%, 95%, 98% or 100% sequence identity across 10, 15, 20, 25, 26, 27, or 28 continuous nucleotides of SEQ ID NO:2, SEQ ID NO:3, SEQ ID NO:4, SEQ ID NO:5, SEQ ID NO:6 or SEQ ID NO:7.

Upon binding mHSP70 on the surface of a cell, the nucleic acid compound provided herein (including embodiments thereof) may be internalized by the cell. The term "internalized," "internalizing," or "internalization" as provided herein refers to a composition (e.g., a compound, a nucleic acid compound, a therapeutic agent, an imaging agent) being drawn into the cytoplasm of the cell (e.g. after being engulfed by a cell membrane). In embodiments, the cell is a malignant cell. In embodiments, the cell is a breast cancer cell. In embodiments, the cell is a prostate cancer cell. In embodiments, the cell is a liver cancer cell. In embodiments, the cell is a pancreatic cancer cell. In embodiments, the cell is a lung cancer cell. In embodiments, the cell is a leukemia cell. In embodiments, the cell is a non-malignant cell.

The nucleic acid compound provided herein (including embodiments thereof) may include a compound moiety. Where the nucleic acid compound includes a compound moiety, the compound moiety may be covalently (e.g. directly or through a covalently bonded intermediary) attached to the RNA sequence (see, e.g., useful reactive moieties or functional groups used for conjugate chemistries set forth above). Thus, in embodiments, the nucleic acid compound further includes a compound moiety covalently attached to the RNA sequence. In embodiments, the compound moiety and the RNA sequence form a conjugate.

In embodiments, the nucleic acid compound has the formula:

R-L-C           (I).

In formula (I), R is the nucleic acid compound, L is a chemical linker and C is the compound moiety. Thus, in embodiments, the nucleic acid compound and the compound moiety are linked through a chemical linker (-L-). In embodiments, the chemical linker is a covalent linker or a non-covalent linker. In embodiments, the chemical linker is a covalent linker. In embodiments, the chemical linker is a bond —O—, —S—, —C(O)—, —C(O)O—, —C(O)NH—, —S(O)₂NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. The chemical linker may be unsubstituted $C_1$-$C_{20}$ (e.g., $C_1$-$C_6$) alkylene, unsubstituted 2 to 20 membered (e.g., 2 to 6 membered) heteroalkylene, unsubstituted $C_3$-$C_8$ (e.g., $C_5$-$C_7$) cykloalkylene, unsubstituted 3 to 8 membered (e.g., 3 to 6 membered) heterocycloalkylene, unsubstituted $C_5$-$C_{10}$ (e.g., $C_5$-$C_6$) arylene, or unsubstituted 5 to 10 membered (e.g., 5 to 6 membered) heteroarylene. In embodiments, the chemical linker is a covalent linker, a non-covalent linker, a peptide linker (a linker including a peptide moiety), a nucleic acid linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties are chemically different. In embodiments, the chemical linker includes a first substituted or unsubstituted alkylene connected through a nucleic acid linker with a second substituted or unsubstituted alkylene. In embodiments, the chemical linker includes a first substituted or unsubstituted heteroalkylene connected through a nucleic acid linker with a second substituted or unsubstituted heteroalkylene.

The chemical linker provided herein may include the remnants of a chemically reactive functional group reacted with a second chemically reactive functional group, thereby forming a covalent linker. Thus, a chemical linker (e.g., $L^1$, $L^2$, $L^3$, $L^{1A}$, $L^{1B}$, $L^{3A}$, $L^{3B}$) as referred to herein may include the resulting linker formed by reacting two reactive groups (moieties), for example, a covalent reactive group as described herein (e.g., alkyne, thiol, azide, maleimide). In embodiments, the chemical linker is a 1,3 triazole linker (i.e., a linker including a 1,3-triazolene linker moiety wherein the linker may further optionally include alkylene (substituted or unsubstituted), heteroalkylene (substituted or unsubstituted), cycloalkylene (substituted or unsubstituted), heterocycloalkylene (substituted or unsubstituted), arylene (substituted or unsubstituted), heteroarylene (substituted or unsubstituted), amide (—C(O)NH—), ester (—C(O)O—), sulfonamide (—SO$_2$NH—) and the like, including combinations thereof). Non-limiting examples of linkers useful for the compositions and methods provided herein are linkers that include alkylene groups (substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene including substituted or unsubstituted alkylene groups and substituted or unsubstituted heteroalkylene amide (—C(O)NH—), ester (—C(O)O—), sulfonamide (—SO$_2$NH—), amine groups (—NH—), epoxyene groups, sulfone groups (—S(O)— or —SO$_2$—), ether group (—O—) or ethylene glycol or derivatives or combinations thereof.

In embodiments, the chemical linker includes a nucleic acid linker. A nucleic acid linker as provided herein is a nucleic acid molecule connecting two chemical moieties (e.g., the RNA sequence and the compound moiety) through covalent binding. In embodiments, the nucleic acid linker includes a first nucleic acid hybridized to a second nucleic acid, wherein the first nucleic acid is covalently bound to the RNA sequence and said second nucleic acid is covalently bound to the compound moiety. Thus, in embodiments, the nucleic acid linker includes a double-stranded nucleic acid. In embodiments, the nucleic acid linker is a double-stranded nucleic acid. In embodiments, the nucleic acid linker includes at least 5 nucleotides. In embodiments, the nucleic acid linker includes at least 10 nucleotides. In embodiments, the nucleic acid linker includes at least 20 nucleotides. In embodiments, the nucleic acid linker includes at least 30 nucleotides. In embodiments, the nucleic acid linker includes at least 40 nucleotides. In embodiments, the nucleic acid linker includes at least 50 nucleotides. In embodiments, the nucleic acid linker includes at least 60 nucleotides. In embodiments, the nucleic acid linker includes at least 70 nucleotides. In embodiments, the nucleic acid linker includes at least 80 nucleotides. In embodiments, the nucleic acid linker includes at least 90 nucleotides. In embodiments, the nucleic acid linker includes at least 100 nucleotides.

In embodiments, the nucleic acid linker includes SEQ ID NO:9 (AGUUUUUUACAUUUUG), SEQ ID NO:10 (CAAAAUGUAAAAAACU), SEQ ID NO:11 (GGAUG-GAUGGAUGGUA) or SEQ ID NO:12 (UACCAUC-CAUCCAUCC). In embodiments, the nucleic acid linker includes SEQ ID NO:9. In embodiments, the nucleic acid linker includes SEQ ID NO:10. In embodiments, the nucleic acid linker includes SEQ ID NO:11. In embodiments, the nucleic acid linker includes SEQ ID NO:12. In embodiments, the nucleic acid linker includes SEQ ID NO:9 and SEQ ID NO:10. In embodiments, the nucleic acid linker includes SEQ ID NO:11 and SEQ ID NO:12.

In embodiments, the chemical linker has the formula:

$$-L^1-L^2-L^3-  \quad (II).$$

In formula (I), $L^1$, $L^2$ and $L^3$ are chemical linkers. In formula (II), $L^1$ links $L^2$ to the RNA sequence and $L^3$ links $L^2$ to the compound moiety. In embodiments, $L^2$ is a nucleic acid linker. In embodiments, $L^2$ includes a first nucleic acid hybridized to a second nucleic acid, wherein the first nucleic acid is covalently bound to $L^1$ and said second nucleic acid is covalently bound to $L^3$.

In embodiments, $L^1$ and $L^3$ are independently a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. In embodiments, $L^1$ and $L^3$ are independently substituted or unsubstituted alkylene, substituted or unsubstituted heteroalkylene. In embodiments, $L^1$ and $L^3$ are independently substituted or unsubstituted alkylene. In embodiments, $L^1$ and $L^3$ are independently substituted or unsubstituted heteroalkylene. In embodiments, $L^1$ and $L^3$ are independently substituted or unsubstituted $C_1$-$C_{10}$ alkylene. In embodiments, $L^1$ and $L^3$ are independently unsubstituted $C_1$-$C_{10}$ alkylene. In embodiments, $L^1$ and $L^3$ are independently unsubstituted $C_1$-$C_5$ alkylene. In embodiments, $L^1$ and $L^3$ are independently unsubstituted $C_3$ alkylene.

In embodiments, $L^1$ has the formula -$L^{1A}$-$L^1$-$L^{1B}$ (IIA). In formula (IIA), $L^{1A}$ and $L^{1B}$ are independently a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^3$ has the formula -$L^{3A}$-$L^3$-$L^{3B}$ (IIB). In formula (IIB), $L^{3A}$ and $L^{3B}$ are independently independently a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, the compound moiety is non-covalently (e.g. through ionic bond(s), van der Waal's bond(s)/interactions, hydrogen bond(s), polar bond(s), or combinations or mixtures thereof) attached to the RNA sequence.

In embodiments, the compound moiety is a therapeutic moiety or an imaging moiety. In embodiments, the therapeutic moiety is covalently attached to the RNA sequence. In embodiments, the imaging moiety is covalently attached to the RNA sequence. In embodiments, the imaging moiety is attached to the RNA sequence through a linker provided herein (e.g., L). The term "therapeutic moiety" as provided herein is used in accordance with its plain ordinary meaning and refers to a monovalent compound having a therapeutic benefit (prevention, eradication, amelioration of the underlying disorder being treated) when given to a subject in need thereof. Therapeutic moieties as provided herein may include, without limitation, peptides, proteins, nucleic acids, nucleic acid analogs, small molecules, antibodies, enzymes, prodrugs, cytotoxic agents (e.g. toxins) including, but not limited to ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, and glucocorticoid. In embodiments, the therapeutic moiety is an anti-cancer agent or chemotherapeutic agent as described herein. In embodiments, the therapeutic moiety is a nucleic acid moiety, a peptide moiety or a small molecule drug moiety. In embodiments, the therapeutic moiety is a nucleic acid moiety. In embodiments, the therapeutic moiety is a peptide moiety. In embodiments, the therapeutic moiety is a small molecule drug moiety. In embodiments, the therapeutic moiety is a nuclease. In embodiments, the therapeutic moiety is an immunostimulator. In embodiments, the therapeutic moiety is a toxin. In embodiments, the therapeutic moiety is a nuclease. In embodiments, the therapeutic moiety is a zinc finger nuclease. In embodiments, the therapeutic moiety is a transcription activator-like effector nuclease. In embodiments, the therapeutic moiety is Cas9. In embodiments, the therapeutic moiety is gemcitabine or a reactive fragment thereof. "Gemcitabine" as provided herein refers to the chemical compound 4-amino-1-(2-deoxy-2,2-difluoro-β-D-erythro-pentofuranosyl)pyrimidin-2(1H)-on. In a customary sense gemcitabine refers to CAS Registry No. 95058-81-4.

In embodiments, the therapeutic moiety is an activating nucleic acid moiety (a monovalent compound including an activating nucleic acid) or an antisense nucleic acid moiety (a monovalent compound including an antisense nucleic acid). An activating nucleic acid refers to a nucleic acid capable of detectably increasing the expression or activity of a given gene or protein. The activating nucleic acid can increase expression or activity 10%, 20%, 30%, 40%, 50%, 60%, 70%, 80%, 90% or more in comparison to a control in the absence of the activating nucleic acid. In certain instances, expression or activity is 1.5-fold, 2-fold, 3-fold, 4-fold, 5-fold, 10-fold or higher than the expression or activity in the absence of the activating nucleic acid.

In embodiments, the therapeutic moiety is an miRNA moiety (a monovalent compound including a miRNA), an mRNA moiety (a monovalent compound including an mRNA), an siRNA moiety (a monovalent compound including an siRNA) or an saRNA moiety (a monovalent compound including an saRNA). In embodiments, the therapeutic moiety is a miRNA moiety. The term "miRNA" is used in accordance with its plain ordinary meaning and refers to a small non-coding RNA molecule capable of post-transcriptionally regulating gene expression. In one embodiment, a miRNA is a nucleic acid that has substantial or complete identity to a target gene. In embodiments, the miRNA inhibits gene expression by interacting with a complementary cellular mRNA thereby interfering with the expression of the complementary mRNA. Typically, the miRNA is at least about 15-50 nucleotides in length (e.g., each complementary sequence of the miRNA is 15-50 nucleotides in length, and the miRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

In embodiments, the therapeutic moiety is a siRNA moiety or saRNA moiety as described herein. In embodiments, the therapeutic moiety is an anticancer agent moiety. In embodiments, the therapeutic moiety is an mRNA moiety. In embodiments, the therapeutic moiety is a siRNA moiety. In embodiments, the therapeutic moiety is a saRNA moiety. In embodiments, the therapeutic moiety is a cDNA moiety. In embodiments, the therapeutic moiety is a C/EBPalpha saRNA moiety. A "C/EBPalpha saRNA" as provided herein is a saRNA capable of activating the expression of a C/EBPalpha protein. In embodiments, the therapeutic moiety is a HSP70 siRNA moiety. A "HSP70 siRNA" as provided herein is a siRNA capable of inhibiting the expression of a HSP70 (e.g. mHSP70) protein. In embodiments, the therapeutic moiety is a KRAS siRNA moiety. A "KRAS siRNA" as provided herein is a siRNA capable of inhibiting the expression of a KRAS protein. In embodiments, the therapeutic moiety is a PDL1 siRNA moiety. A "PDL1 siRNA" as provided herein is a siRNA capable of inhibiting the expression of a PDL1 protein.

In embodiments, the therapeutic moiety includes SEQ ID NO:13 (UGAAUUAGCUGUAUCGUCAAGG), SEQ ID NO:14 (UUGACGAUACAGCUAAUUCAUA), SEQ ID NO:15 (ACUGUACUCCUCUUGACCUGCU), SEQ ID NO:16 (CAGGUCAAGAGGAGUACAGUUA), SEQ ID NO:17 (GAAGCAAAGUGAUACACAUUU) or SEQ ID NO:18 (AUGUGUAUCACUUUGCUUCUU). In embodiments, the therapeutic moiety includes SEQ ID NO:13. In embodiments, the therapeutic moiety includes SEQ ID NO:14. In embodiments, the therapeutic moiety includes SEQ ID NO:15. In embodiments, the therapeutic moiety includes SEQ ID NO:16. In embodiments, the therapeutic moiety includes SEQ ID NO:17. In embodiments, the therapeutic moiety includes SEQ ID NO:18.

The compound moiety provided herein may be an imaging moiety. An "imaging moiety" as provided herein is a monovalent compound detectable by spectroscopic, photochemical, biochemical, immunochemical, chemical, or other physical means. In embodiments, the imaging moiety is covalently attached to the RNA sequence. Exemplary imaging moieties are without limitation $^{32}P$, radionuclides, positron-emitting isotopes, fluorescent dyes, fluorophores, antibodies, bioluminescent molecules, chemoluminescent molecules, photoactive molecules, metals, electron-dense reagents, enzymes (e.g., as commonly used in an ELISA), magnetic contrast agents, quantum dots, nanoparticles, biotin, digoxigenin, haptens and proteins or other entities which can be made detectable, e.g., by incorporating a radiolabel into a peptide or antibody specifically reactive with a target peptide. Any method known in the art for conjugating an antibody to the moiety may be employed, e.g., using methods described in Hermanson, *Bioconjugate Techniques*

1996, Academic Press, Inc., San Diego. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. In embodiments, the imaging moiety is a bioluminescent molecule. In embodiments, the imaging moiety is a photoactive molecule. In embodiments, the imaging moiety is a metal. In embodiments, the imaging moiety is a nanoparticle.

The compound (e.g., nucleic acid compound) provided herein may include a HSP70 ligand moiety. A "HSP70 ligand moiety" as used herein refers to a monovalent compound (e.g. substituent) capable of binding (interacting) to HSP70 (e.g. mHSP70). The binding may be specific relative to non-HSP70 or relative to other cell surface proteins. In embodiments, the HSP70 ligand moiety is a nucleic acid moiety, a peptide moiety or a small molecule moiety (e.g. a small molecule drug moiety). In embodiments, the HSP70 ligand moiety forms part of the RNA sequence. In embodiments, the HSP70 ligand moiety includes the sequence of SEQ ID NO:8. In embodiments, the HSP70 ligand moiety has the sequence of SEQ ID NO:8. In embodiments, the compound provided herein is bound to a cellular receptor. In embodiments, the cellular receptor is cell surface HSP70. "Cell surface HSP70" as provided herein refers to an HSP70 protein expressed (e.g. present) on the surface of a cell (i.e. on the cell membrane accessible to the extracellular space). In embodiments, the cell surface HSP70 is mHSP70. In embodiments, the cell surface HSP70 is mortalin. In embodiments, the cellular receptor is expressed (e.g. present) on a cancer cell (i.e. on the cancer cell membrane accessible to the extracellular space). In embodiments, the cancer cell is a pancreatic cancer cell. In embodiments, the cancer cell is a glioblastoma cell. In embodiments, the cancer cell is a liver cancer cell. In embodiments, the cancer cell is a prostate cancer cell. In embodiments, the cancer cell is a breast cancer cell. In embodiments, the cancer cell is a leukemia cell.

Pharmaceutical Formulations

Pharmaceutical compositions of the compounds (e.g., nucleic acid compounds) provided herein may include compositions having a therapeutic moiety contained in a therapeutically effective amount, i.e., in an amount effective to achieve its intended purpose. The pharmaceutical compositions of the compounds (e.g., nucleic acid compounds) provided herein may include compositions having imaging moieties contained in an effective amount, i.e., in an amount effective to achieve its intended purpose. The actual amount effective for a particular application will depend, inter alia, on the condition being treated, tested, detected, or diagnosed. When administered in methods to treat a disease, such compositions will contain an amount of active ingredient effective to achieve the desired result, e.g., modulating the activity of a target molecule, and/or reducing, eliminating, or slowing the progression of disease symptoms. Determination of a therapeutically effective amount of a therapeutic moiety provided herein is well within the capabilities of those skilled in the art, especially in light of the detailed disclosure herein. When administered in methods to diagnose or detect a disease, such compositions will contain an amount of an imaging moiety described herein effective to achieve the desired result, e.g., detecting the absence or presence of a target molecule, cell, or tumor in a subject. Determination of a detectable amount of an imaging moiety provided herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

For any composition (e.g., the nucleic acid compounds provided, combinations of an anticancer agent and the nucleic acid compound provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

In another aspect, a pharmaceutical formulation including the nucleic acid compound as provided herein including embodiments thereof and a pharmaceutically acceptable excipient is provided. In embodiments, the ribonucleic acid includes a compound moiety covalently attached to the RNA sequence. As described above, the compound moiety may be a therapeutic moiety or an imaging moiety covalently attached to the RNA sequence.

In another aspect, the pharmaceutical formulation includes the nucleic acid compound as provided herein including embodiments thereof and a therapeutic agent. In embodiments, the nucleic acid compound and the therapeutic agent are not covalently attached. A therapeutic agent as provided herein refers to a composition (e.g. compound, drug, antagonist, inhibitor, modulator) having a therapeutic effect. In embodiments, the therapeutic agent is an anticancer agent. In embodiments, the pharmaceutical formulation includes a pharmaceutically acceptable excipient.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Methods of Delivery

Provided herein are methods of delivering compounds (e.g., nucleic acid compounds as provided herein) to a cell through binding the compound to cell surface HSP70 (e.g. mHSP70) and internalizing the compound into the cell. Thus, in one aspect, a method of delivering a compound into a cell is provided. The method includes contacting a cell surface HSP70 (e.g. mHSP70) with a compound including an HSP70 ligand moiety. The compound is allowed to pass into the cell thereby delivering the compound into the cell. The passage into the cell may be facilitated (mediated) by the cell surface HSP70. The compound does not include a nucleic acid sequence of SEQ ID NO:2, SEQ ID NO:3, SEQ ID NO:4, SEQ ID NO:5, SEQ ID NO:6 or SEQ ID NO:7. In embodiments, the cell surface HSP70 is present on a cell surface. In embodiments, the HSP70 forms part of a cellular vesicle upon passage into the cell. In embodiments, the cell surface HSP70 is mHSP70 present on a cell surface. In embodiments, the cell surface HSP70 is a cell surface mHSP70.

In embodiments, the compound does not include a nucleic acid sequence having about 98% sequence identity to SEQ ID NO:2, SEQ ID NO:3, SEQ ID NO:4, SEQ ID NO:5, SEQ ID NO:6 or SEQ ID NO:7. In embodiments, the compound does not include a nucleic acid sequence having about 98% sequence identity to SEQ ID NO:2. In embodiments, the compound does not include a nucleic acid sequence having about 98% sequence identity to SEQ ID NO:3. In embodiments, the compound does not include a nucleic acid sequence having about 98% sequence identity to SEQ ID NO:4. In embodiments, the compound does not include a nucleic acid sequence having about 98% sequence identity to SEQ ID NO:5. In embodiments, the compound does not include a nucleic acid sequence having about 98% sequence identity to SEQ ID NO:6. In embodiments, the compound does not include a nucleic acid sequence having about 98% sequence identity to SEQ ID NO:7.

In embodiments, the compound does not include a nucleic acid sequence having about 95% sequence identity to SEQ ID NO:2, SEQ ID NO:3, SEQ ID NO:4, SEQ ID NO:5, SEQ ID NO:6 or SEQ ID NO:7. In embodiments, the compound does not include a nucleic acid sequence having about 95% sequence identity to SEQ ID NO:2. In embodiments, the compound does not include a nucleic acid sequence having about 95% sequence identity to SEQ ID NO:3. In embodiments, the compound does not include a nucleic acid sequence having about 95% sequence identity to SEQ ID NO:4. In embodiments, the compound does not include a nucleic acid sequence having about 95% sequence identity to SEQ ID NO:5. In embodiments, the compound does not include a nucleic acid sequence having about 95% sequence identity to SEQ ID NO:6. In embodiments, the compound does not include a nucleic acid sequence having about 95% sequence identity to SEQ ID NO:7.

In embodiments, the compound does not include a nucleic acid sequence having about 90% sequence identity to SEQ ID NO:2, SEQ ID NO:3, SEQ ID NO:4, SEQ ID NO:5, SEQ ID NO:6 or SEQ ID NO:7. In embodiments, the compound does not include a nucleic acid sequence having about 90% sequence identity to SEQ ID NO:2. In embodiments, the compound does not include a nucleic acid sequence having about 90% sequence identity to SEQ ID NO:3. In embodiments, the compound does not include a nucleic acid sequence having about 90% sequence identity to SEQ ID NO:4. In embodiments, the compound does not include a nucleic acid sequence having about 90% sequence identity to SEQ ID NO:5. In embodiments, the compound does not include a nucleic acid sequence having about 90% sequence identity to SEQ ID NO:6. In embodiments, the compound does not include a nucleic acid sequence having about 90% sequence identity to SEQ ID NO:7.

In embodiments, the compound does not include a nucleic acid sequence having about 85% sequence identity to SEQ ID NO:2, SEQ ID NO:3, SEQ ID NO:4, SEQ ID NO:5, SEQ ID NO:6 or SEQ ID NO:7. In embodiments, the compound does not include a nucleic acid sequence having about 85% sequence identity to SEQ ID NO:2. In embodiments, the compound does not include a nucleic acid sequence having about 85% sequence identity to SEQ ID NO:3. In embodiments, the compound does not include a nucleic acid sequence having about 85% sequence identity to SEQ ID NO:4. In embodiments, the compound does not include a nucleic acid sequence having about 85% sequence identity to SEQ ID NO:5. In embodiments, the compound does not include a nucleic acid sequence having about 85% sequence identity to SEQ ID NO:6. In embodiments, the compound does not include a nucleic acid sequence having about 85% sequence identity to SEQ ID NO:7.

In embodiments, the compound does not include a nucleic acid sequence having about 80% sequence identity to SEQ ID NO:2, SEQ ID NO:3, SEQ ID NO:4, SEQ ID NO:5, SEQ ID NO:6 or SEQ ID NO:7. In embodiments, the compound does not include a nucleic acid sequence having about 80% sequence identity to SEQ ID NO:2. In embodiments, the compound does not include a nucleic acid sequence having about 80% sequence identity to SEQ ID NO:3. In embodiments, the compound does not include a nucleic acid sequence having about 80% sequence identity to SEQ ID NO:4. In embodiments, the compound does not include a nucleic acid sequence having about 80% sequence identity to SEQ ID NO:5. In embodiments, the compound does not include a nucleic acid sequence having about 80% sequence identity to SEQ ID NO:6. In embodiments, the compound does not include a nucleic acid sequence having about 80% sequence identity to SEQ ID NO:7.

In embodiments, the compound does not include a nucleic acid sequence having about 80%, 85%, 90%, 95%, 98% or 100% sequence identity across the whole sequence of SEQ ID NO:2, SEQ ID NO:3, SEQ ID NO:4, SEQ ID NO:5, SEQ ID NO:6 or SEQ ID NO:7. In embodiments, the compound does not include a nucleic acid sequence having about 80%, 85%, 90%, 95%, 98% or 100% sequence identity across 10, 15, 20, 25, 26, 27, or 28 continuous nucleotides of SEQ ID NO:2, SEQ ID NO:3, SEQ ID NO:4, SEQ ID NO:5, SEQ ID NO:6 or SEQ ID NO:7.

In embodiments, the compound does not include a ribonucleic acid. In embodiments, the compound does not include a nucleic acid. In embodiments, the compound does not include an aptamer.

In embodiments, the compound includes a therapeutic agent or an imaging agent. In embodiments, the compound is a therapeutic agent or an imaging agent. In embodiments, the therapeutic agent is an antibody, a peptide, a nucleic acid or a small molecule (e.g. a drug). In embodiments, the imaging agent is a bioluminescent molecule, a photoactive molecule, a metal or a nanoparticle. In embodiments, the compound is an antibody, a peptide, a nucleic acid or a small molecule. In embodiments, the compound is an antibody. In embodiments, the compound is a nucleic acid compound as provided herein including embodiments thereof In embodiments, the method includes detecting the nucleic acid compound in the cell thereby detecting the cell.

As described above the nucleic acid compounds provided herein including embodiments thereof may be used to deliver compound moieties or compounds (e.g., therapeutic agents or an imaging agents) into a cell. Where a compound moiety (e.g., therapeutic moiety or imaging moiety) is delivered into a cell, the compound moiety may be covalently attached to the nucleic acid compound (RNA sequence) provided herein including embodiments thereof. Upon binding of the nucleic acid compound (RNA sequence) to mHSP70 on a cell, the compound moiety is internalized by the cell while being covalently attached to the nucleic acid compound (RNA sequence). Thus, in one aspect, a method of delivering a compound moiety into a cell is provided. The method includes, (i) contacting a cell with the nucleic acid compound as provided herein including embodiments thereof and (ii) allowing the nucleic acid compound to bind to a mHSP70 on the cell and pass into the cell thereby delivering the compound moiety into the cell.

Alternatively, where a compound is delivered into a cell, the compound (e.g., a therapeutic agent or an imaging agent) may not be covalently attached to the nucleic acid compound (RNA sequence). Upon binding of the nucleic acid compound provided herein including embodiments thereof to mHSP70 on a cell, the nucleic acid compound and the compound provided are internalized by the cell without being covalently attached to each other. Thus, in another aspect, a method of delivering a compound into a cell is provided. The method includes (i) contacting a cell with a compound and the nucleic acid compound as provided herein including embodiments thereof and (ii) allowing the nucleic acid compound to bind to a mHSP70 on the cell and the compound to pass into the cell thereby delivering the compound into the cell. In embodiments, the compound is a therapeutic agent or imaging agent. In embodiments, the compound is non-covalently attached to the nucleic acid compound.

Methods of Treatment

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma). For example certain methods herein treat cancer by decreasing or reducing or preventing the occurrence, growth, metastasis, or progression of cancer; or treat cancer by decreasing a symptom of cancer. Symptoms of cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) would be known or may be determined by a person of ordinary skill in the art.

Where combination treatments are contemplated, it is not intended that the agents (i.e. nucleic acid compounds) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In another aspect, a method of treating cancer is provided. The method includes administering to a subject in need thereof an effective amount of the nucleic acid compound as provided herein (including embodiments thereof). In embodiments, the nucleic acid compound further includes an anticancer therapeutic moiety. In another aspect, a method of treating cancer is provided. The method includes administering to a subject in need thereof an effective amount of an anticancer agent and a nucleic acid compound as provided herein including embodiments thereof.

Methods of Detecting a Cell

The nucleic acid compositions provided herein may also be used for the delivery of compounds and compound moieties to a cell expressing HSP70 (e.g. mHSP70). As described above, the compounds and compound moieties delivered may be imaging agents useful for cell detections. Thus, in one aspect, a method of detecting a cell is provided. The method includes (i) contacting a cell with the nucleic acid compound as provided herein including embodiments thereof, wherein the nucleic acid compound further includes an imaging moiety. (ii) The nucleic acid compound is allowed to bind to HSP70 (e.g. mHSP70) on the cell and pass into the cell. (iii) The imaging moiety is detected thereby detecting the cell.

In another aspect, a method of detecting a cell is provided. The method includes (i) contacting a cell with an imaging agent and the nucleic acid compound as provided herein including embodiments thereof. (ii) The nucleic acid compound is allowed to bind to mHSP70 on the cell and the imaging agent is allowed to pass into the cell. (iii) The imaging agent is detected thereby detecting the cell.

In embodiments, the cell is a malignant cell. In embodiments, the cell is a breast cancer cell. In embodiments, the cell is a prostate cancer cell. In embodiments, the cell is a liver cancer cell. In embodiments, the cell is a pancreatic cancer cell. In embodiments, the cell is a non-malignant cell. In embodiments, the cell forms part of an organism. In embodiments, the organism is a mammal. In embodiments, the cell forms part of a cell culture.

EXAMPLES

Example 1

In the present study, we employed a 2'-fluoropyrimidine-RNA (2'F-RNA) combinatorial library and isolated 2'F RNA aptamers through a whole cell-based SELEX for the targeted delivery. As a non-KRAS-based approach that targets a silenced gene, we activated epigenetically silenced transcription factors C/EBPα as a novel druggable target in pancreatic cancer. The anti-tumor effects of targeted delivery of C/EBPα-saRNA by cancer specific RNA aptamer into PDAC was investigated in vitro and in vivo xenograft model along with identification of aptamer binding cell membrane proteins.

In Vitro Selection of RNA Aptamers to the Intact Target Cells

The human pancreatic adenocarcinoma cells (Panc-1) were used as target cells for the aptamer selection and negative cells were used for the counter-selection steps to remove irrelevant binding. A library of 2'F RNAs was used to increase nuclease-resistance and enhance aptamer folding. To isolate 2'F RNA aptamers binding to intact cells, a library of approximately $4^{40}$ different 2'F RNA molecules, containing a 40-nt-long random sequence flanked by defined sequences, was screened by SELEX. After 14 cycles of selection, the highly enriched aptamer pools were cloned.

For comparison of individual sequences and structures, two different groups of aptamers were selected (Table 1). P19 and P1 showed multi-stem loops and the structural similarity containing a common motif, GAAUGCCC. Minimum energy structural analyses of the selected aptamers were carried out using Mfold[30]. As depicted, the calculated secondary structures of the RNA aptamers contained several stem-loop regions (FIG. 1a).

Pancreatic Cancer Specific Internalization of RNA Aptamers

Figure 7:
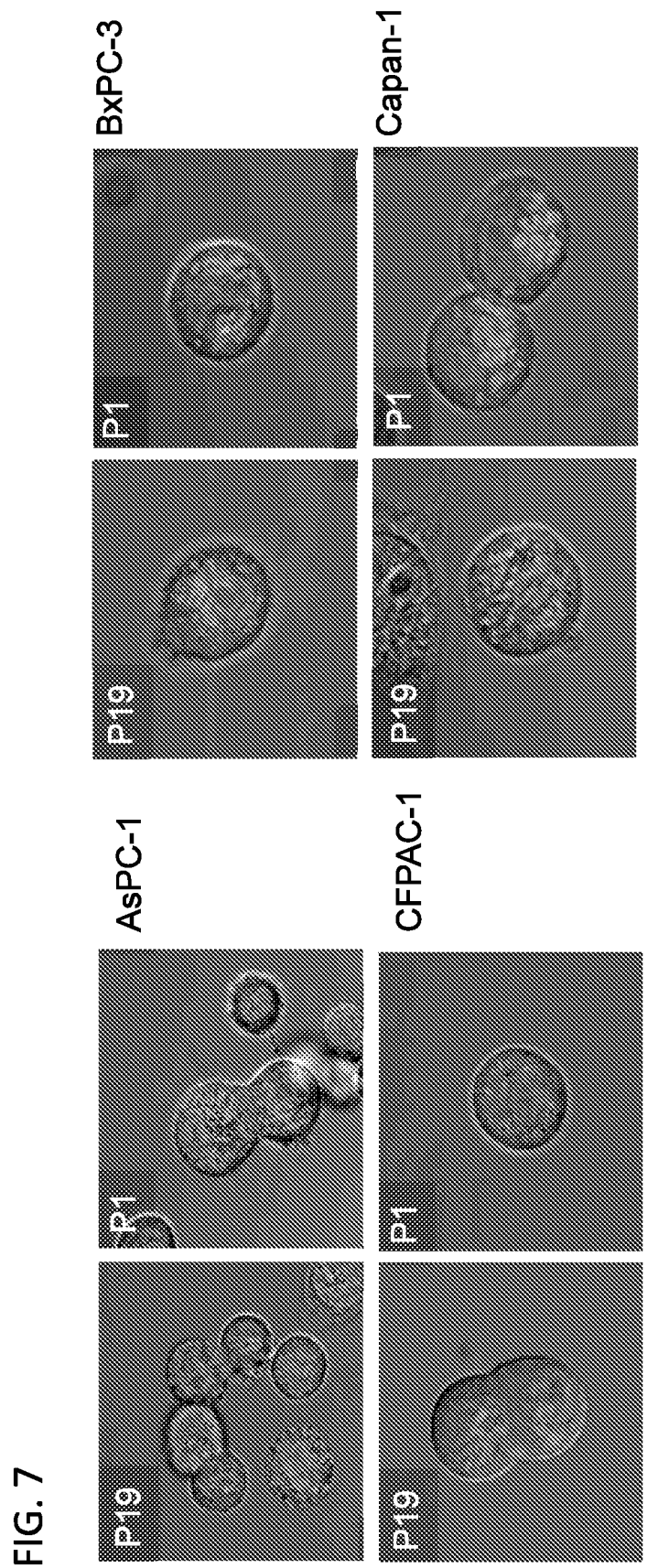
FIG. 7: The internalization of aptamers in various pancreatic cancer cell lines. Cy3-labeled RNAs (100 nM) was tested for internalization by confocal. Cy3-labeled RNA and Hoechst 33342 staining are shown.

Flow cytometric analyses of the individual clones revealed the aptamers bound to the target cells (FIG. 1b). In order to determine that the selected two different aptamers were internalized in the pancreatic cancer cells, the live-cell confocal microscopy with the Cy3-labeled RNA transcripts was carried out. The RNA aptamers were internalized specifically in target cells Panc-1, but not control cells (FIG. 1c). FIG. 1C showed the aptamers aggregated within the cytoplasm, suggesting that the RNA aptamers enter into cells via receptor-mediated endocytosis. To test that the aptamers recognize different types of pancreatic cancer cells, five different pancreatic cancer cell line cells were tested for aptamer uptake. All of the tested aptamers are internalized in the different pancreatic cancer cells (FIG. 1c and FIG. 7). In order to determine the selected aptamers binds to the normal pancreatic cell, primary epithelial pancreatic cancer cells were incubated with Cy3 labeled aptamers. The aptamers didn't get internalized in the pancreatic epithelial normal cells (FIG. 1d), indicating that the RNA aptamers bound to and were internalized in cancer cells specifically.

Figure 1E:
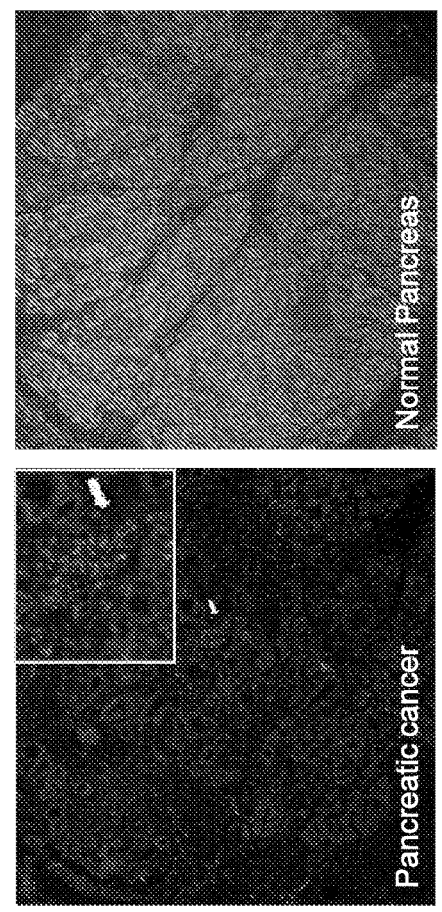
Figure 1G:
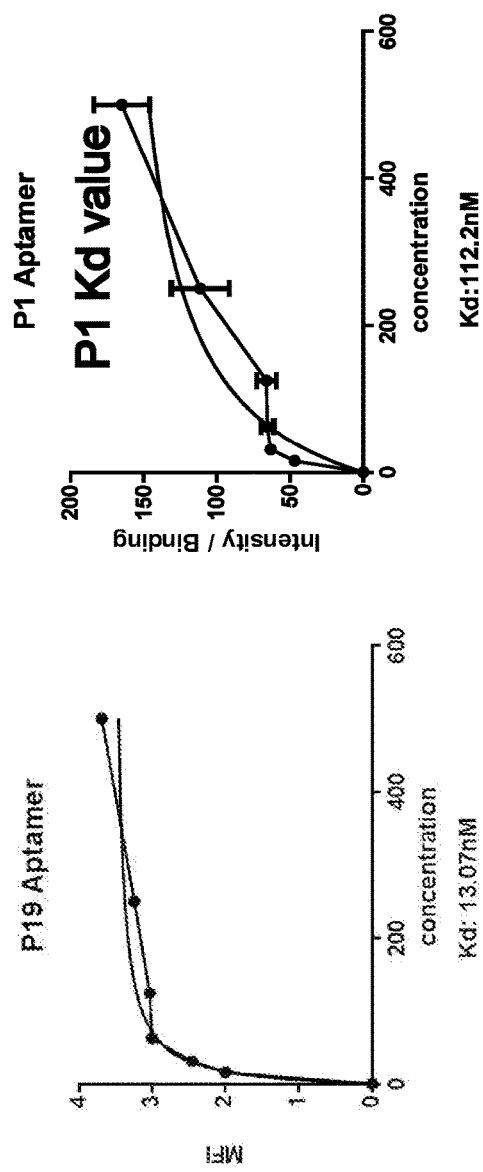
Figure 2A:
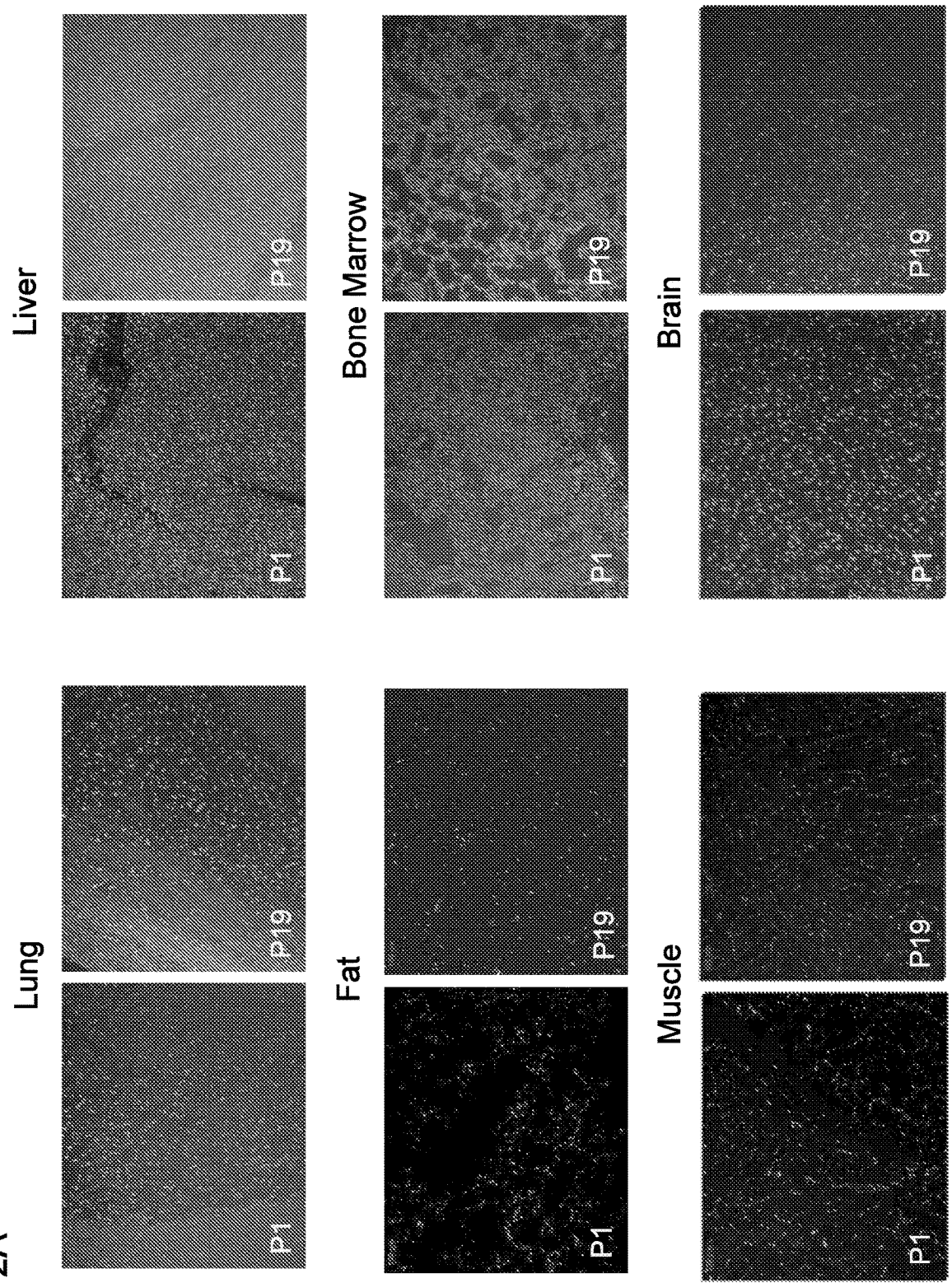
FIG. 2A-2B. Histology (FIG. 2A) The representative images by histopathological screen in normal tissues. The samples were stained with Cy3 labeled aptamer Pb and P19 respectively. The sample sections were then examined under microscope at 100× magnification. Cy3-labeled RNA.
Figure 2A:
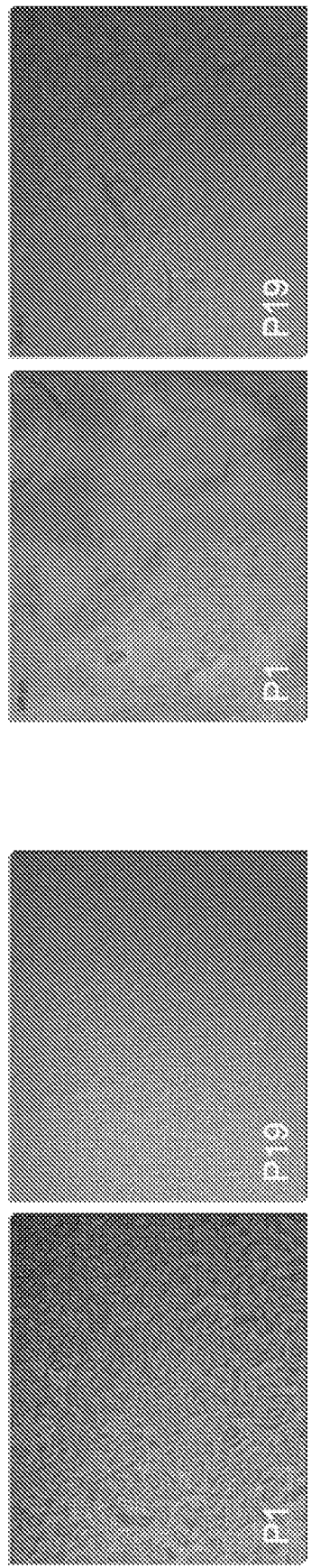
Figure 2B:
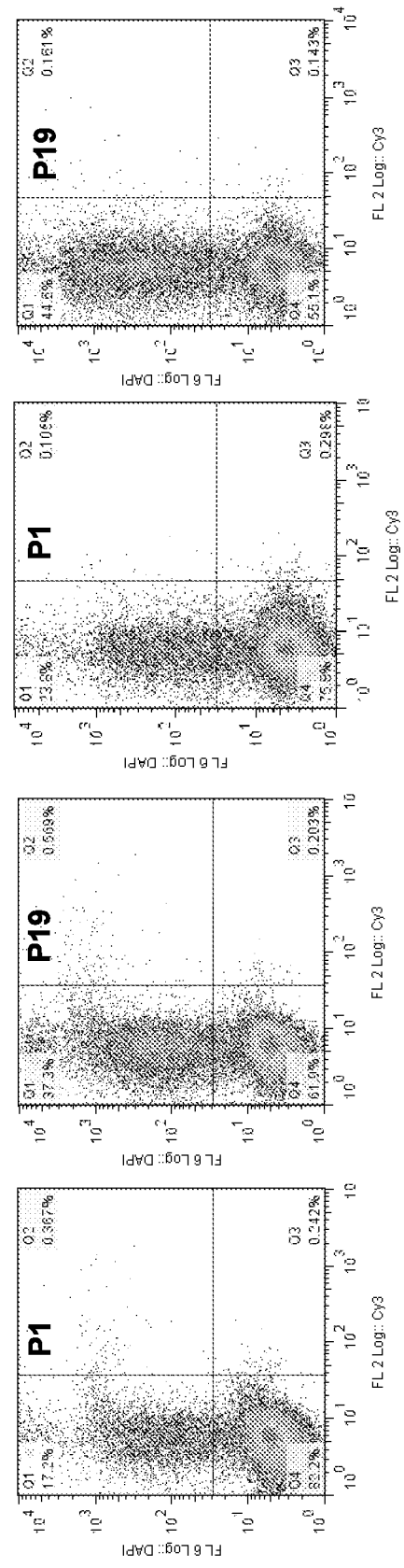
Figure 9:
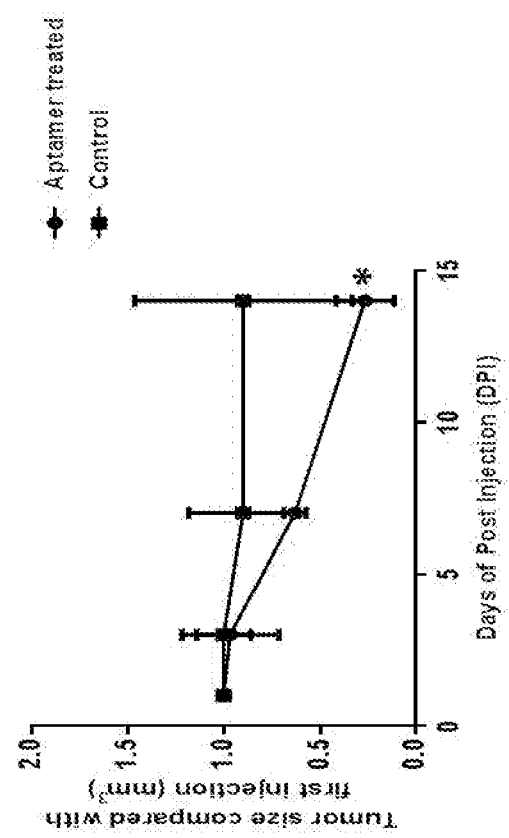
FIG. 9: In vivo assays of anti-tumor effects of aptamers only. For gemcitabine resistant tumor test, ASPC-1 pancreatic cancer cells were engrafted in 5-weeks-old female NOD/SCID mice. After engraftment, aptamer were treated through tail vein and measured the tumor size. * t-test: P value<0.05.
Figure 10:
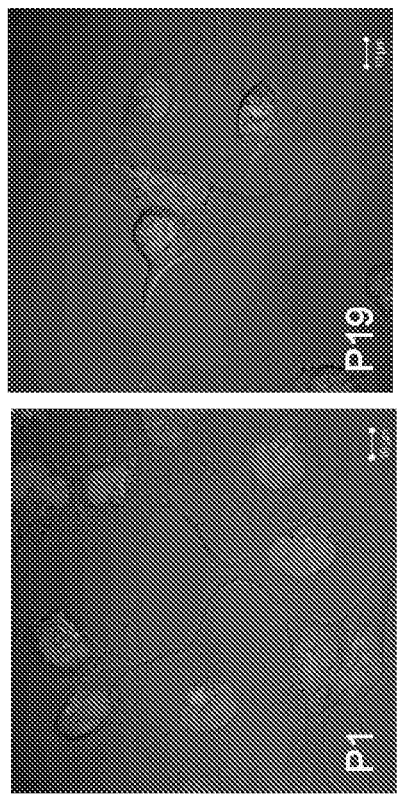
FIG. 10: The internalization of aptamers in other types of cancer cell lines. Cy3-labeled RNAs (100 nM) was tested for internalization by confocal. Cy3-labeled RNA and Hoechst 33342 staining are shown.

Furthermore, to investigate the cancer specificity, Cy3 labeled P1 and P19 were tested on human pancreatic cancer and normal pancreas tissue specimens by histopathology. Based on the histopathology in human PC specimens, the aptamer score was divide into lower level (<7), medium level (>7 and <14) and high level (>14 and <20). Only the specimens from 3 cases showed without prominent P1 or P19 positive staining (lower level). And these cases showed significantly longer survival (p=0.011 at P1, p=0.013 at P19) which means less malignant. The others show high level P1 and P19 positive rate in 43 and medium level in 26 patients. The survival period is 21.0±2.64 months in high level P1 group, 15.9±3.17 months in medium level P1 group and 13.0±4.29 months in low level P1 group. P19 and P1 follow the high tumor grades with low survival rate. P1 and P19 recognize cancer specifically. There is almost no or only scanty P1 or P19 positive staining noted in non-tumor part of pancreas and breast cancer specimen as control. As cell binding assays showed, both P19 and P1 recognized pancreatic cancer tissues specifically, not normal pancreas tissues. The representative images showed in FIG. 1e. The measured binding affinity (Kd) of P19 was 13.07 nM. P1 was 2.2 nM (FIG. 1g). In cancer tissue staining histopathologically, both the P1 and P19 present in cytoplasm and the correlation coefficient between aptamer scores of P1 and P19 is 0.891(FIG. 1). Other normal tissues such as liver, spleen, and kidney etc showed negative staining including T and B cells (FIGS. 2a and b). The internalization assays were screened in other type of cancers. (FIG. 9).

Figure 11A:
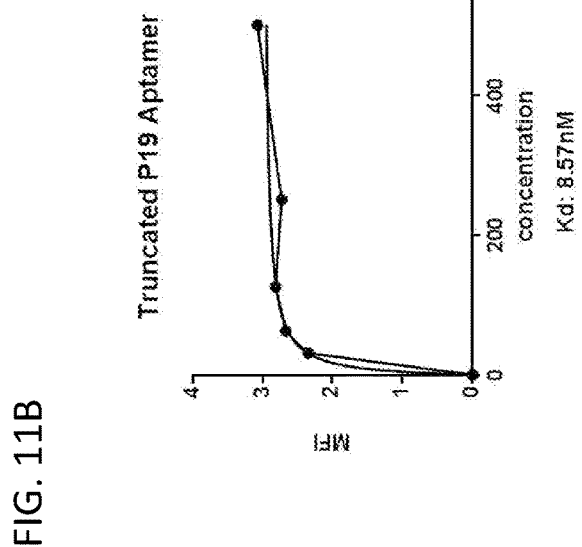
FIG. 11A-11D.
Figure 11B:
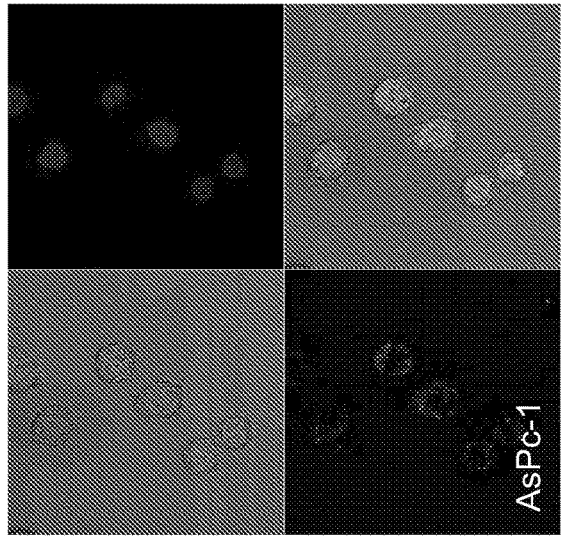
Figure 11C:
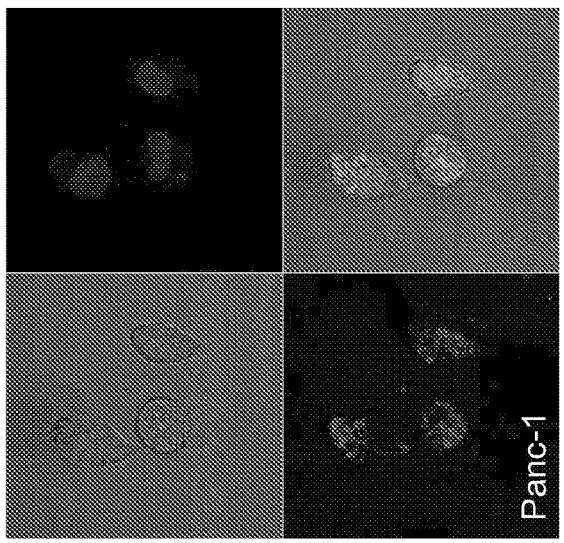
Figure 11D:
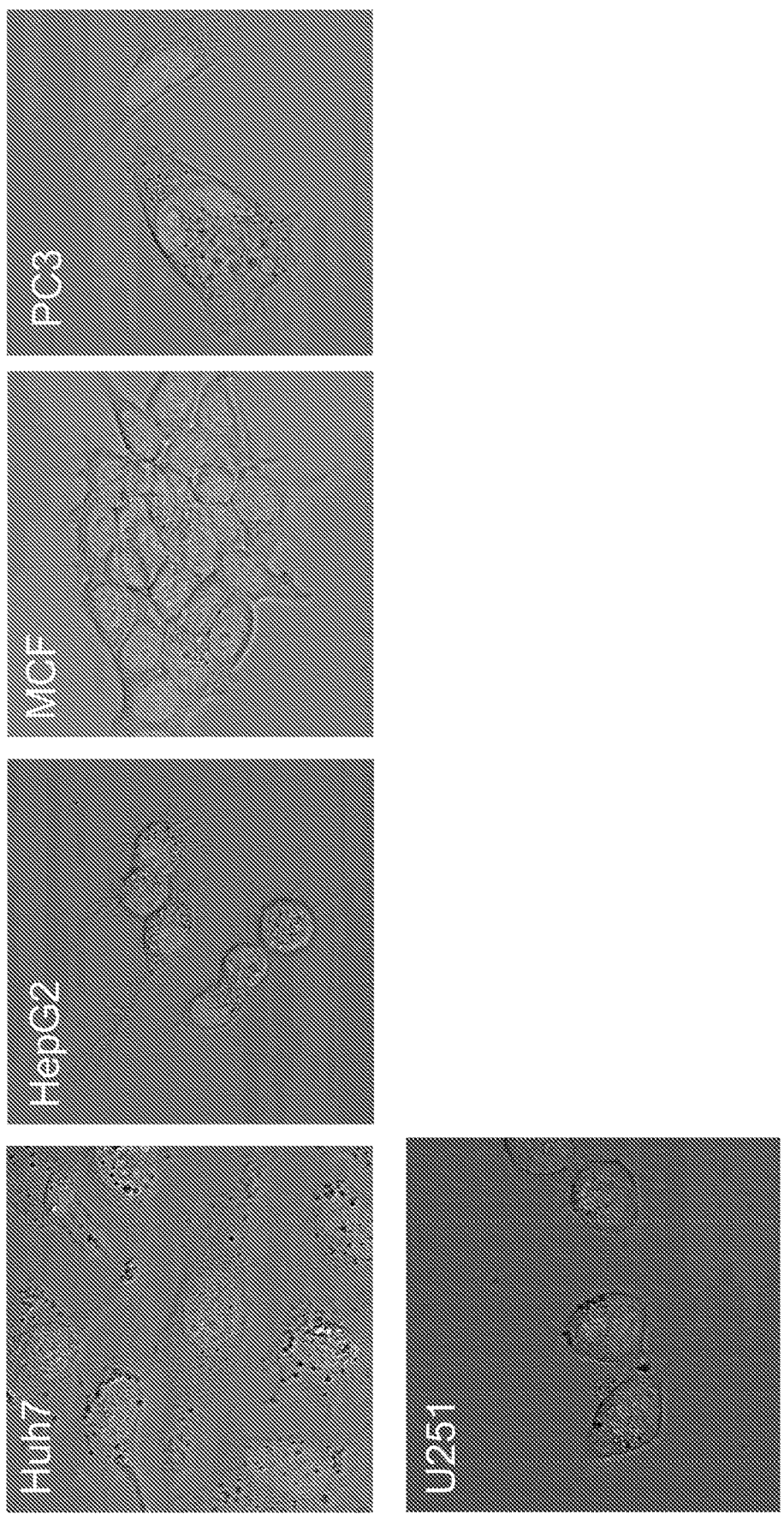
Figure 13B:
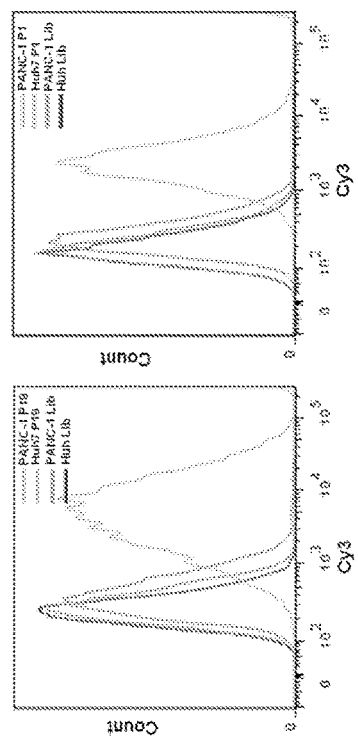
FIG. 13A-13G: The aptamer secondary structure and cancer cell-specific internalization.
Figure 12:
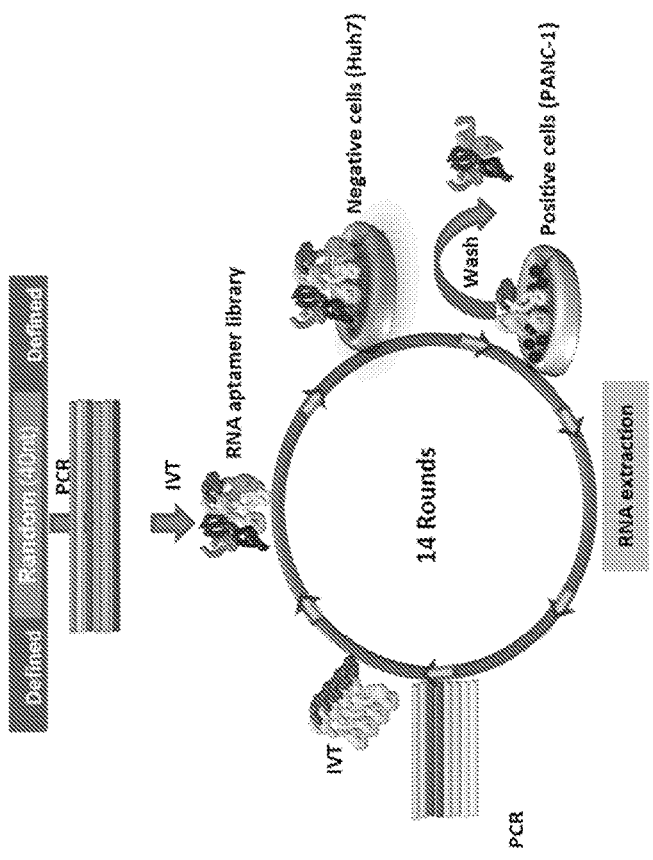
FIG. 12: Naïve whole cell based SELEX. Schematic live-cell SELEX procedures. The DNA library contained 40 nt of random sequences was synthesized and amplified by PCR. 2'F modified RNA aptamer library was synthesized throughout in vitro transcription. To identify the enriched RNA aptamers that bind to target cells, the RNA aptamer library pool was incubated on the negative cells. After removal of non-specific binding to the negative cells, the supernatant was incubated on the positive cells for positive selection. Total RNA was extracted and amplified through polymerase chain reaction (PCR) and in vitro transcription (IVT). The RNA aptamer selection was repeated for 14 rounds of SELEX. The enriched pools were cloned and the positive clones were sequenced to identify individual RNA aptamers.
Figure 13A:
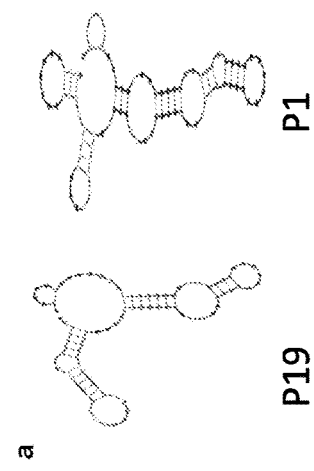
Figure 13C:
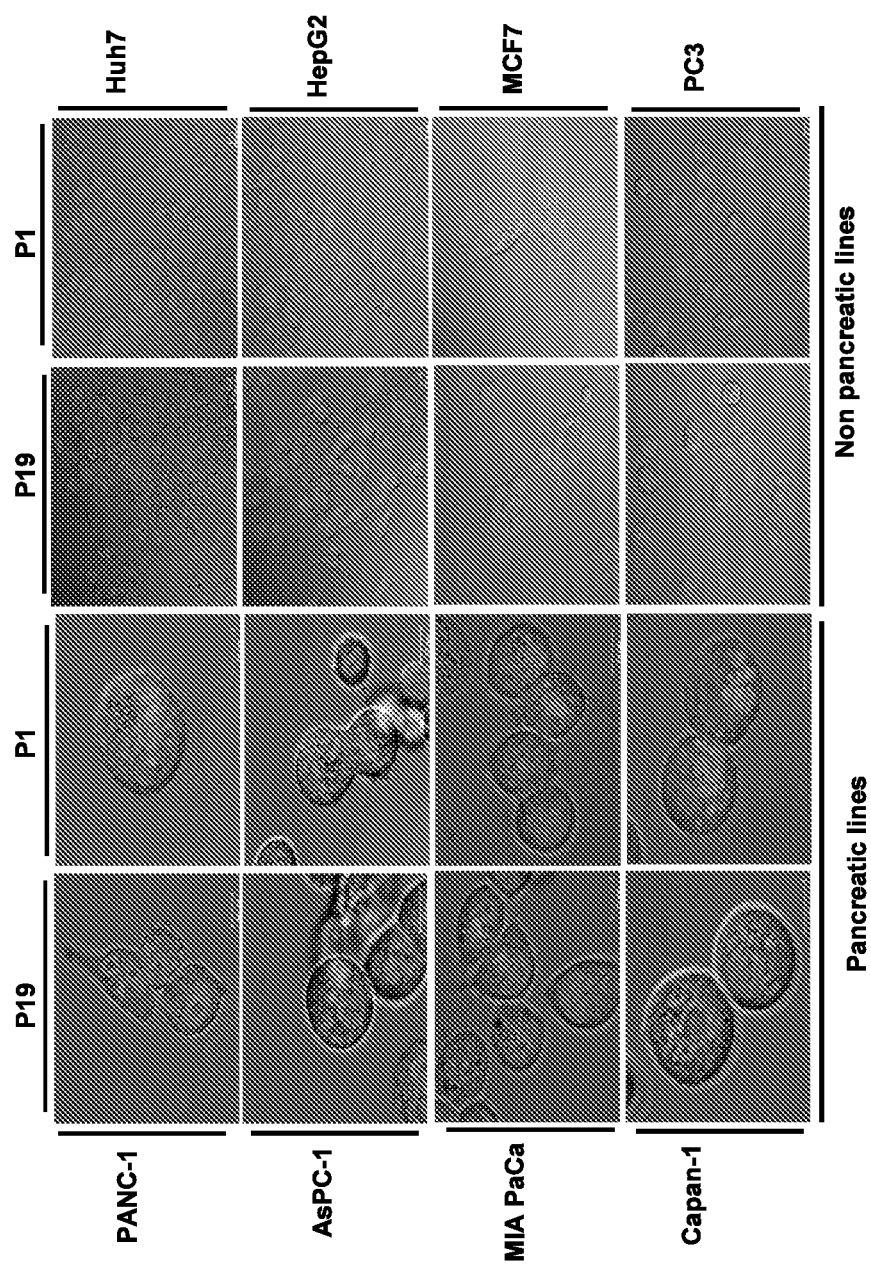
Figure 13D:
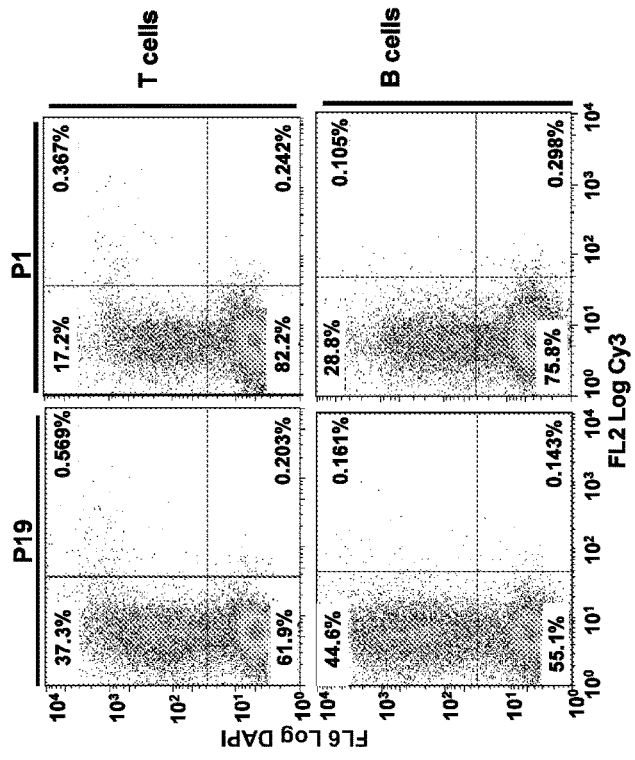
Figure 13E:
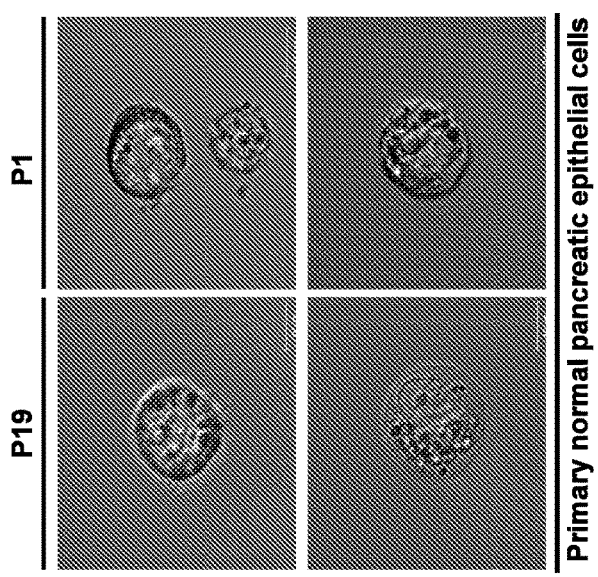
Figure 13F:
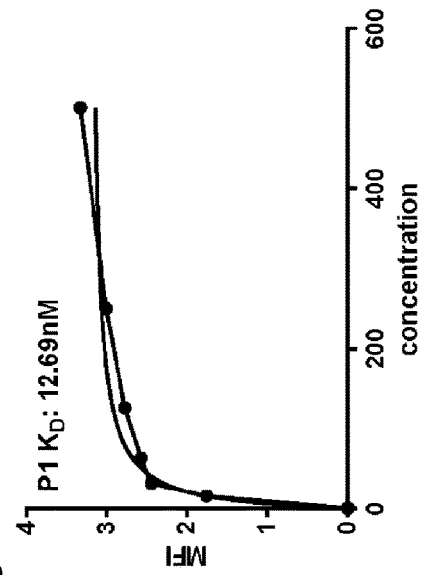
Figure 13G:
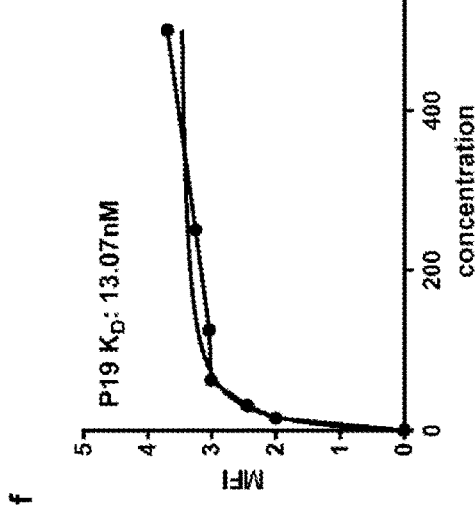

To identify that the common motif, GAAUGCCC, was related with the binding motif, the P19 was truncated to the size of 28mer including the common motif based on the expected structure by Mfold (FIG. 11a). The Kd value of truncated P19 was 8.77nM (FIG. 11a). The minimized P19 got internalized into Panc-1 and AsPC-1 cells in the same way of full length of P19 staying (FIG. 11a). Cell binding assays was screened in other types of cancers like liver, breast and prostate cancers. The truncated P19 showed negative reaction, indicating that it is pancreatic cancer specific RNA aptamers (FIG. 11a). Taken together, these results show that the P1 and P19 recognize pancreatic cancer cells specifically.

Identification of Cell Membrane Target of the RNA Aptamer

Figure 3B:
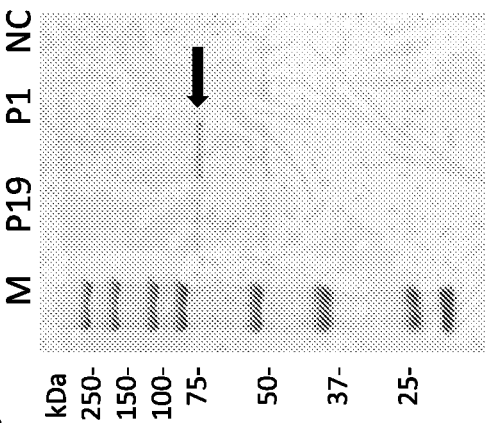
FIG. 3A-3F. Identification and validation of target ligands.
Figure 3A:
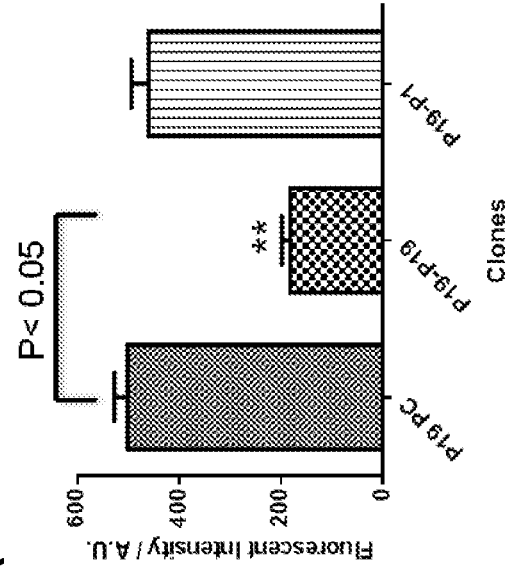

To verify that the each aptamer was binding to the same cell surface proteins, Panc-1 cells were incubated with fluorescently labeled P19 RNA (200 nM) and increasing amounts (1 μM) of unlabeled each clone aptamers as competitors against the labeled one (FIG. 3a). The fluorescence intensity of labeled RNAs was measured in the presence of increasing amounts of competitors using confocal microscopy. The intensity of P19 competed with unlabeled P19 was significantly decreased; others showed insignificant changes, indicating that each RNA aptamer has the different binding sites or bind the different targets.

Figure 3C:
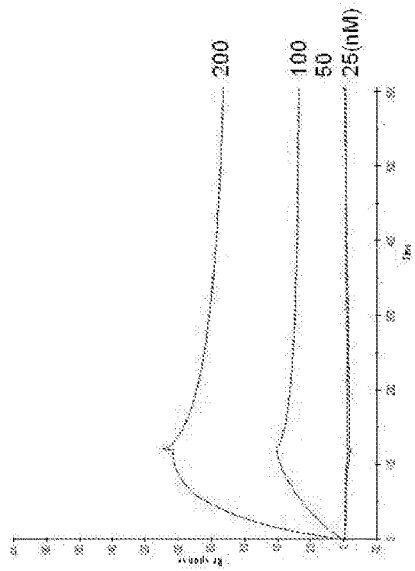
Figure 3D:
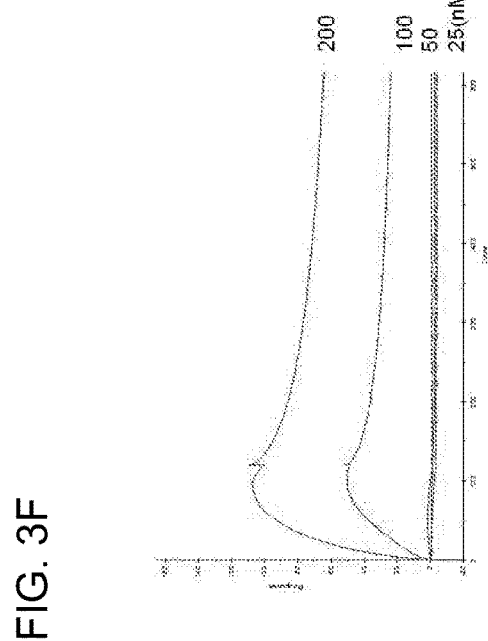
Figure 3E:
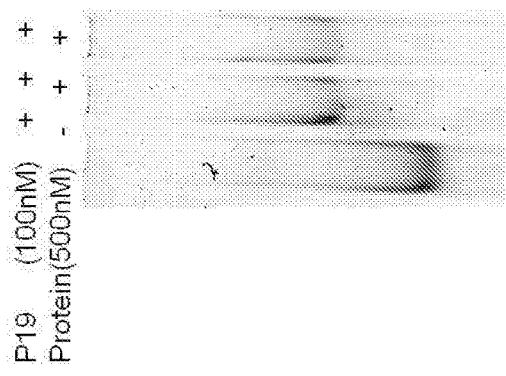
Figure 3F:
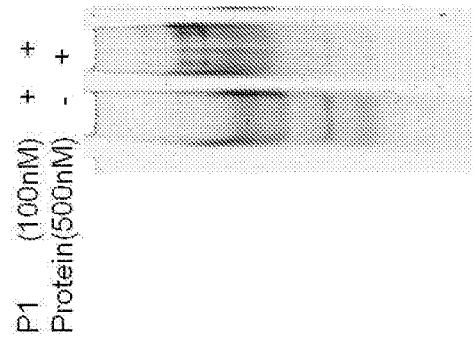
Figure 4B:
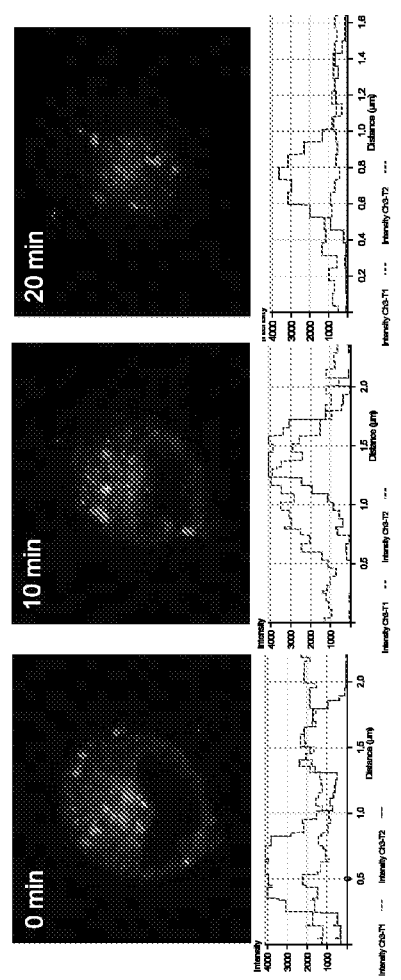
FIG. 4A-4F. Gene activation in vitro.

To identify the target ligands of aptamer on cell membrane, cell membrane proteins were retrieved by biotinylated aptamers. The retrieved proteins were run in SDS-PAGE gel. P19 and P1 showed the band sized around 75 kDa (FIG. 4b). The aptamer captured proteins were analyzed by MASS-SPEC for peptide matching fingerprinting. For the target ligands of P19 and P1, mitochondrial Hsp70 which is mortalin was identified (FIGS. 3c and d). To validate the results of MASS-SPEC, gel shift assays and surface plasmon resonance (SPR) assays were used. In gel shift assays, the shifted band was observed in both P19 and P1 (FIGS. 3e and g). As shown in SPR sensogram, P1 and P19 bound to the mortalin (FIGS. 3f and h).

The Anti-proliferative Effects of C/EBPα Delivered by RNA Aptamers In Vitro

Figure 4D:
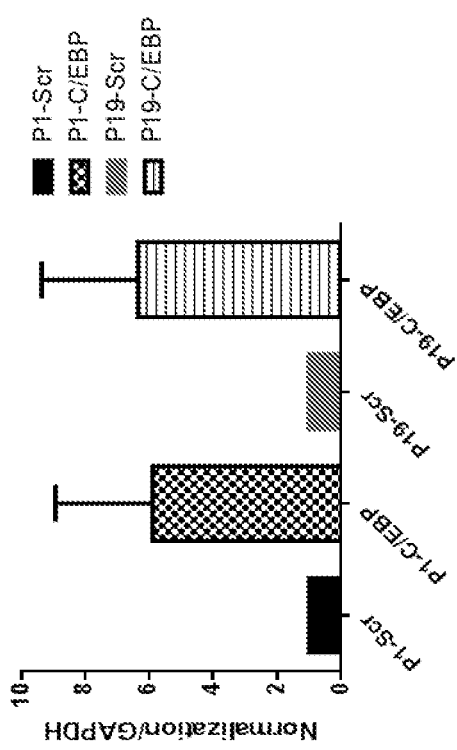
Figure 4A:
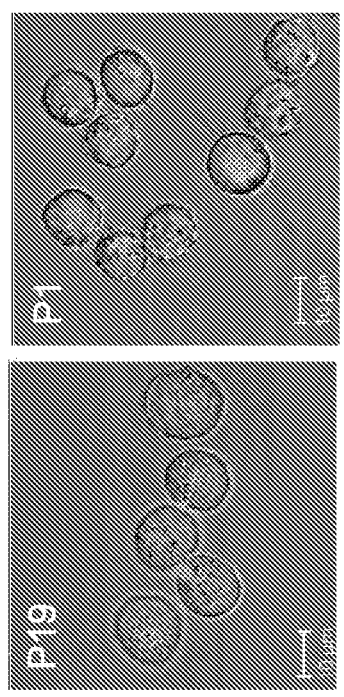
Figure 4C:
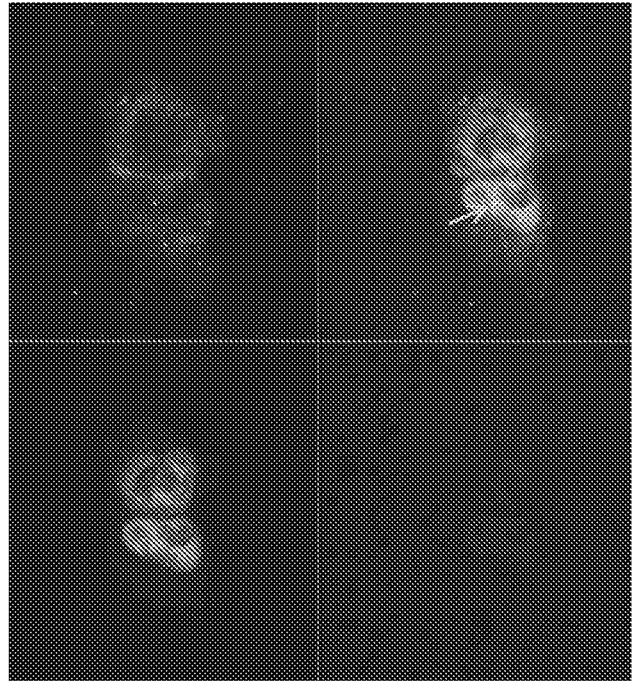
Figures 4E, 4F:
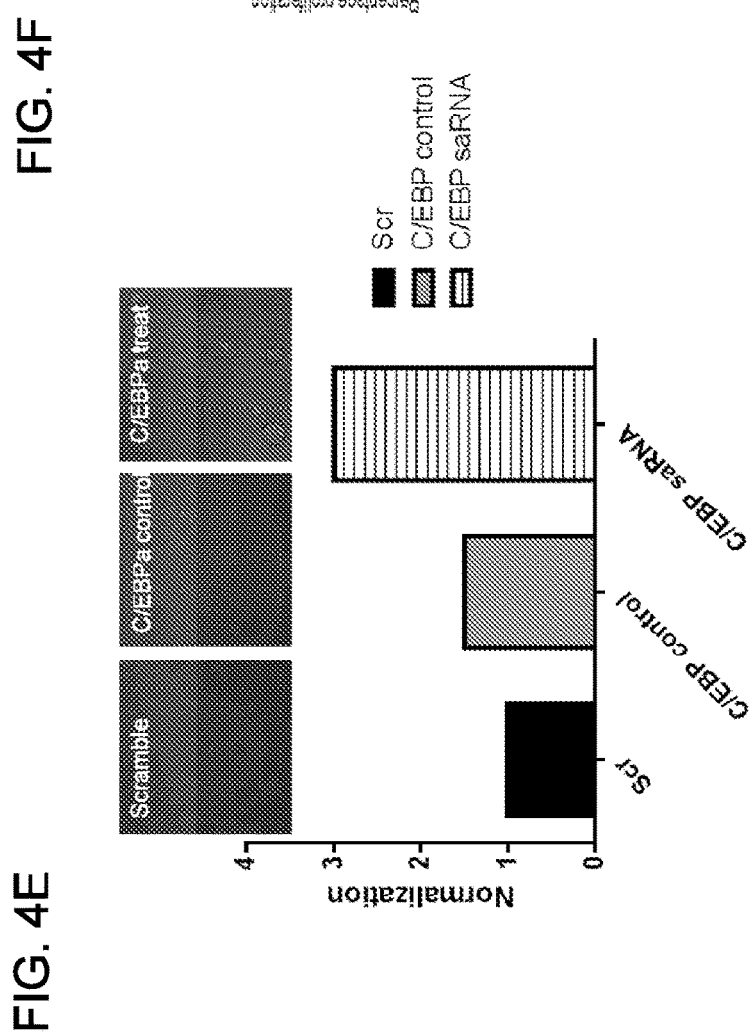
Figure 8:
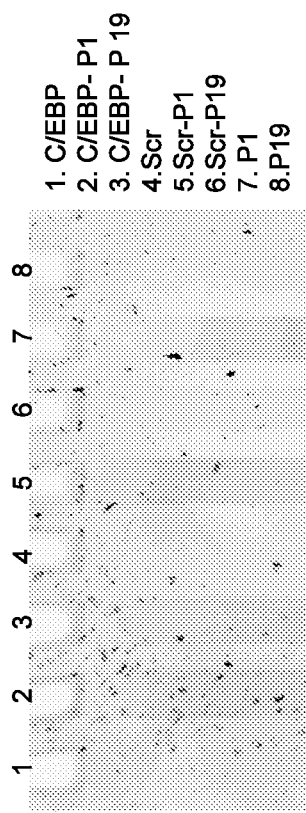
FIG. 8: The conjugates of P19 and P1 with C/EBPa and scramble. The P1-stick and P19-stick RNA was refolded in binding buffer and the sense-stick and antisense strand was annealed to the complementary partner using the same molar amounts as the corresponding partner strand to form the stick-C/EBPα RNAs or scramble RNA. 12% native PAGE gel.

To investigate the effect of gene activation which is targeted delivery of C/EBPα-saRNA by aptamer mediation, P1 and P19 with stick sequence and C/EBPα RNAs or scramble RNA with stick sequence were synthesized chemically. P1 and P19 were annealed with counter partner sequences to make the conjugates (FIG. 8). To keep the function and prevent the structural hindrance, we put the stick sequence between aptamers and C/EBPα saRNAs or scramble RNA. This construct didn't hinder aptamer structures. The P19 and P1 conjugates were internalized into the target cells (FIG. 4a). Receptor mediated endocytosis enters endosome. To have effects, endosomal escape is necessary. To address the issue, live cell imaging was conducted. Late endosome marker, Rab7, was transduced in cells one day before testing the internalization. The conjugate was escaped from the endosome in 10 minutes after localized in late endosome (FIG. 4b). C/EBPα-saRNA was localized with RNA Pol II in nuclear (FIG. 4c). To investigate the gene activation in vitro, the conjugates with C/EBPα-saRNA or scramble RNAs were treated into cells without transfection. The P19 and P1 conjugates significantly activated target genes in mRNA level, comparing with scramble RNA (FIGS. 4d and e). Cell proliferation assays were performed to investigate the anti-proliferative effects of C/EBPα-saRNA in cells. It showed that anti-proliferation effects on day of 3 and 4 after treatment of P19 conjugates (FIG. 4f).

The Anti-tumor Effects of C/EBPα Delivered by RNA Aptamers In Vivo

Figure 5A:
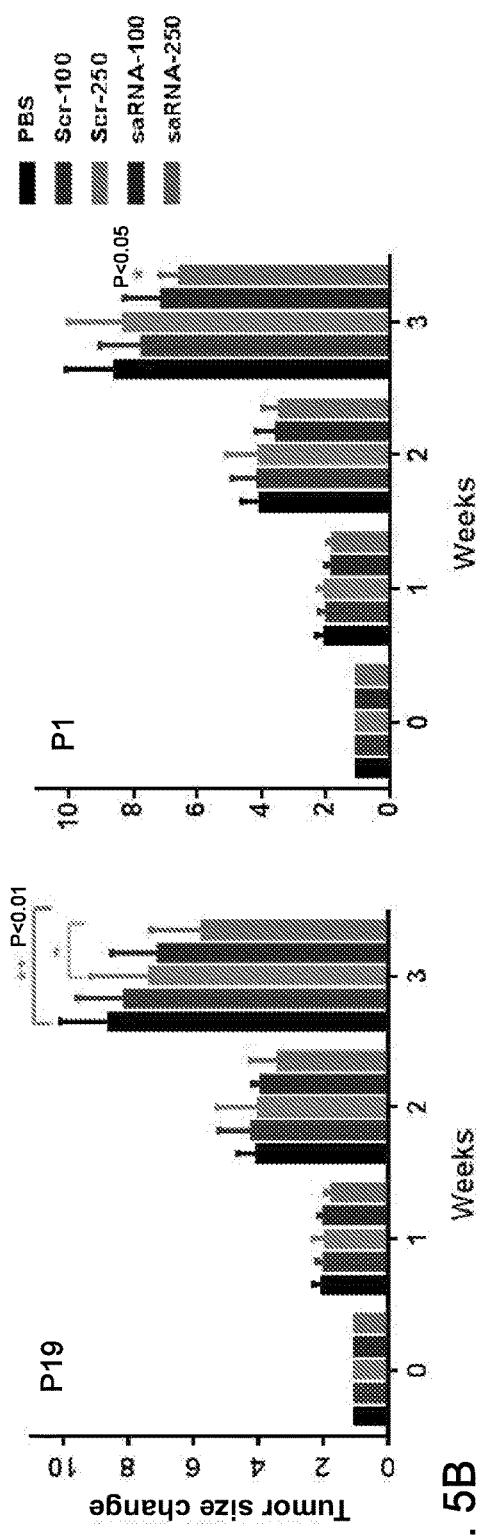
Figure 5B:
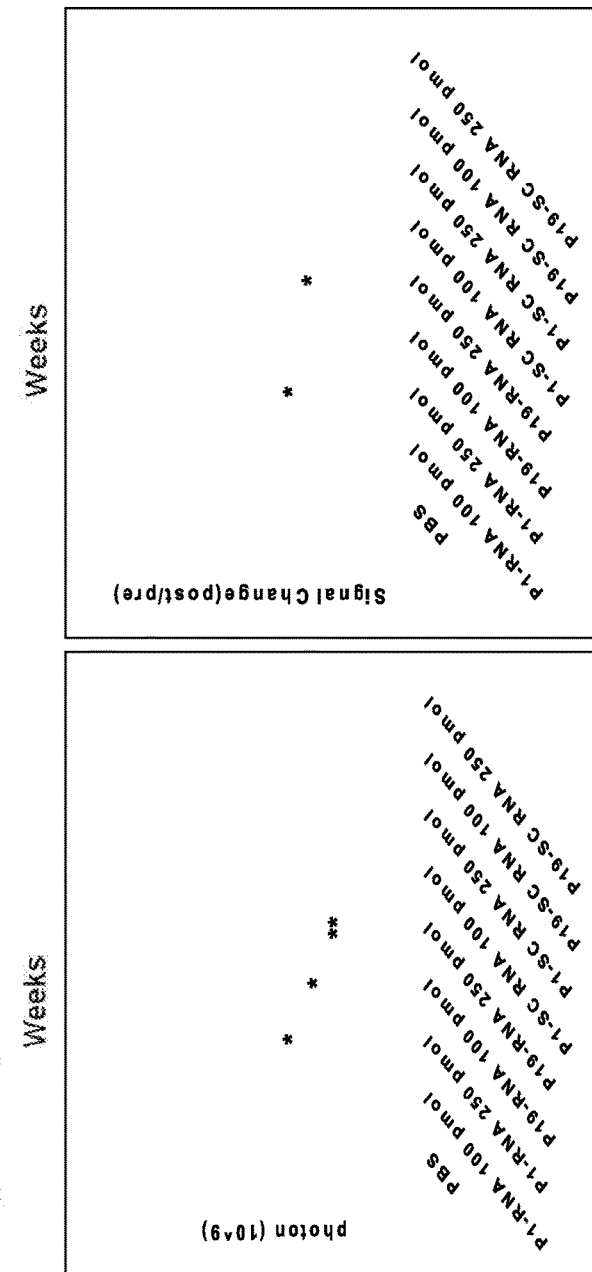
Figure 5F:
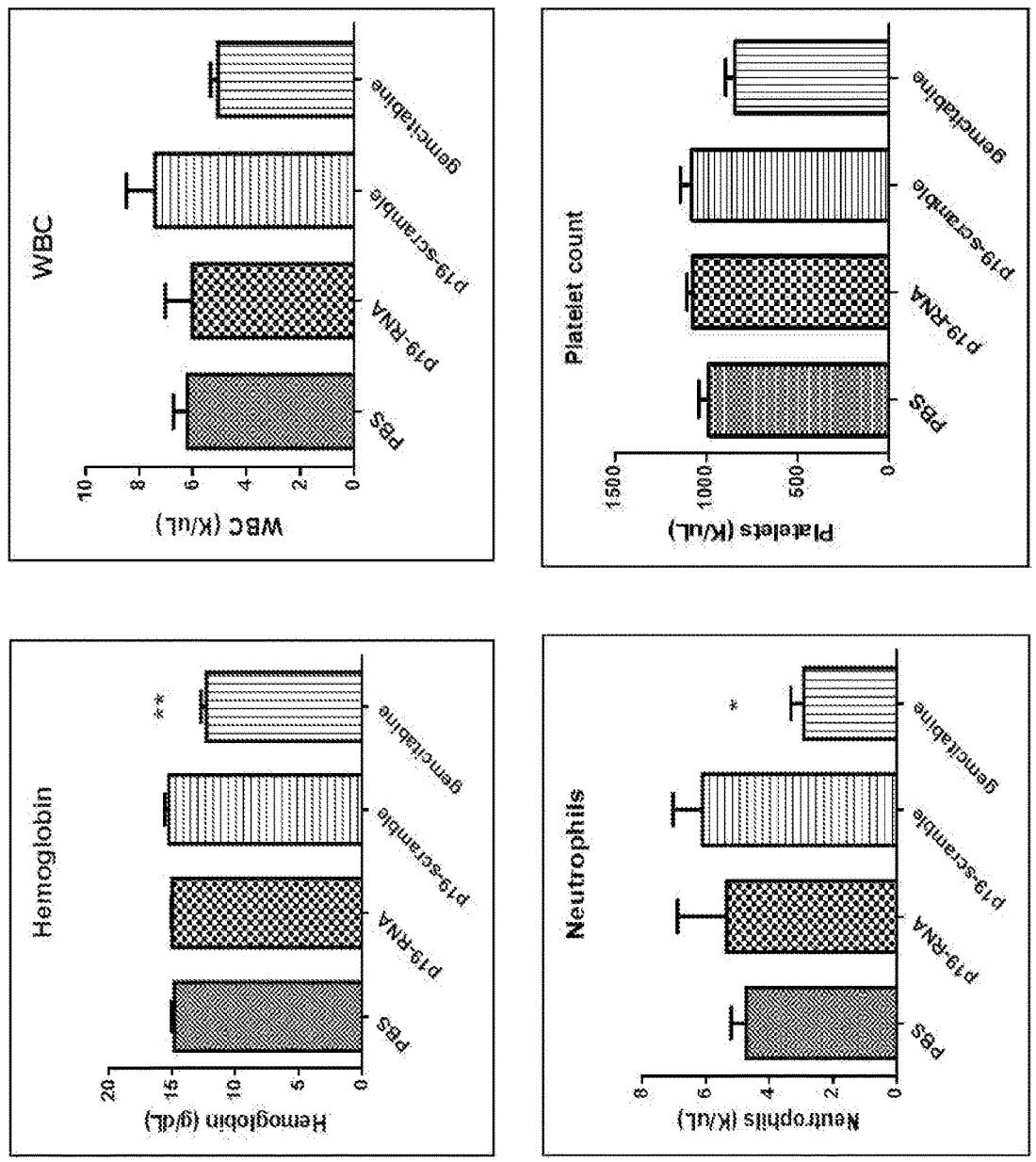

To investigate the anti-tumor effects of C/EBPα-saRNA in vivo, the traceable xenoengrafted mice model was used. The conjugates were delivered into mice by tail vein injection. In the P19 conjugates of 250 pmol injection group, the C/EBPα-saRNAs significantly reduce tumor growth in mice comparing with PBS and scramble RNA injection groups (FIG. 5a). In the P1 conjugates of 250 pmol injection group, the C/EBPα-saRNAs significantly inhibit tumor growth in mice comparing with PBS group (FIG. 5a). Counting the photon and measuring the single changes after treatment, both P19 and P1 of 250 pmol injection group showed the inhibition of tumor growth significantly (FIGS. 5b and c). To compare the anti-tumor effects with gemcitabine, the P19 conjugates of lnmol was injected by tail vein. Gemcitabine of 3 mg was injected by I.P. The P19 conjugates showed the anti-tumor effects significantly comparing with PBS group, but not in gemcitabine group (FIG. 5d). In xenoegrafted mice of gemcitabine resistance cells, the inhibition of tumor growth was observed in the P19 conjugates group. Interestingly, the metastasis to ascites was not observed in the P19 conjugates group. However, in other injection groups, they showed 33% of metastasis (FIG. 5e). In gemcitabine group, it showed the cytotoxicity such as reduction of hemoglobin and neutrophils. But, the P19 conjugate group didn't show the cytotoxicity (FIG. 5f).

Pancreatic cancer is resistant to most of the currently available therapies. Based on their biological properties of different agents, molecular targeted therapeutics have been tested in pancreatic cancer. The most common molecular targets have been epidermal growth receptor (EGFR), epidermal growth receptor type 2 (HER2), and vascular endothelial growth factor (VEGF). The only targeted therapy demonstrating a clinical benefit to date is erlotinib, a tyrosine kinase inhibitor that inhibit ErbB-1 phosphorylation[31]. A phase III trial of erlotinib with gemcitabine exhibited a marginal survival benefit for patients with advanced disease and its routine use is questionable[32]. Kim et al. selected the RNA aptamer P12FR2 to pancreatic adenocarcinoma up-regulated factor (PAUF) which is over-expressed in pancreatic cancer. The P12FR2 decreases tumor growth in an in vivo xenograft model with intraperitoneal injection[33].

However, the intravenous administration (I.V.) for systemic therapy is particularly important in that the vast majority of patients with pancreatic cancer have distant tumor spread at the time of diagnosis Rhim et al[34] show the spread of pancreatic cells to the liver even at the pre-neoplastic stage. In that point, the cancer specific RNA aptamers can be used for imaging for diagnosis, staging and early detection of pancreatic cancer. In this study, we selected two RNA aptamers recognizing pancreatic cancer cells specifically applicable via the intravenous administration systemically.

For targeted delivery of C/EBPα-snRNA into PDAC, we linked the duplex RNA molecule to P19 and P1 which were pancreatic cancer specific. These effectively increased. C/EBPa transcript levels in vitro, Intravenous injection of C/EBPα-snRNA-aptamer conjugate at 250 ug and mmol over 3-4 weeks showed a significant tumor growth inhibition by 30-40% compared to PBS control or scramble-snRNA-aptamer control groups. Gemcitabine which is current gold standard care failed to reduce tumor growth, showing the cytotoxicity on RBCs and neutrophils. Comparing with gemcitabine injection group, C/EBPα-saRNA-aptamer conjugates inhibited the anti-tumor effects with low toxicity. These data support the evidence suggesting that up-regulation of C/EBPα provides a strong antiproliferative role in PDAC. It also suggests good advantages over gemcitabine to cure pancreatic cancer. C/EBPα, tumor suppresser gene, is silenced by histone deacetylation and DNA methylation in the promotor epigenetically in PC encoding gene[20]. The loss of KDM6B encoding histone demethylase enhance aggressiveness of PDAC cells through knockdown of C/EBPα[19]. In this study, the co-localization of RNA Pol II and C/EBPα was observed in nuclear. Histone acetylation and demethylation by the induction C/EBPα will be strived in the future studies.

Regarding the aptamer binding ligands on cell surface, the tumor-associated mitochondrial Hsp70 was identified as the target ligands of the P19 and P1, even though the further research is necessary to FIG. out whether the common motif is the binding site against the target protein. The up-to-date data indicate that cancer cells become addicted to Hsp70 through chaperone's activity on multiple survival pathways, specifically cancer specific features such as hypoxia, oxidative stress, and altered pH. Its high expression in tumors correlates with therapy resistance and poor prognosis[35, 36]. The overexpression of Hsp70 in pancreatic adenocarcinoma increases tumorgenicity and inhibit apoptosis to chemotherapy by directly interfering with several key components of the apoptotic signaling pathway[37, 38]. Hsp70 is constitutively expressed on cell surface of human tumor, not normal cells [39, 40]. The translocalization of Hsp70 on the cancer cell surface and organelle distribution is related to their specific lipid compositions[41-43]. Cancer cells acquiring mitochondria from endothelial display chemoresistance, implicating chemoresistance linked to mitochondria[44]. Mitochondria are gatekeeper of response to chemotherapy. Because cancer cells are demanding high energy, they are much more dependent to mitochondria than normal cells. The most differentially expressed mitochondrial proteins between normal and cancerous cells are cytochrome oxidase and Hsp70[45, 46]. Hsp70 promotes chemoresistance by blocking Bax mitochondrial translocation, pro-apoptotic protein of the mitochondria apoptosis[47]. Hyun et al also report that the expression of Hsp70 modulates the chemoresponsivess in pancreatic cancer[48]. Peptide targeting hsp70 is sensitizing to apoptotic cell death[49]. In this study, mitochondrial Hsp70 was identified as the target ligands of P19 and P1. In vivo experiments, these two clones, P1 and P19 showed anti-tumor effects in gemcitabine resistance tumour cells significantly (FIG. 6e and FIG. 9). The combination of two clones more effectively reduced the tumour size. It implies the P19 and P1 inhibit the function of Hsp70 which is related with chemoresistance.

Methods

Cell Lines

To use intact cells as targets for SELEX, PANC-1 (CRL-1469), Capan-1 (HTB-79), CFPAC-1 (CRL-1918), MIA PaCa-2 (CRL-1420), BxPC-3 (CRL-1687) and AsPC-1

(CRL-1682) were purchased from ATCC. Primary human pancreatic epithelial cells were purchased in cell systems. The cells were cultured according to the cell bank's instructions.

Whole-Cell SELEX (systemic evolution of ligands by exponential enrichment).

The SELEX cycle was performed basically as described by Tuerk and Gold[22]. In vitro selection was carried out essentially as described[52], with a few modifications for this study. For the first round, 5 nmol of the RNA library was incubated with target cells (Panc-1) in 1 ml binding buffer (PBS with $Ca^{2+}$ and $Mg^{2+}$, 0.01% BSA, yeast tRNA). RNAs that bound to target cells were recovered, amplified by RT-PCR and in vitro transcription, and used in the following selection rounds. In subsequent rounds, the RNA concentration was reduced by 10-fold and incubation time was reduced to create a more stringent condition. To remove RNAs non-specifically binding the target cells, the counter-selection was carried out.

Live Cell Confocal Imaging

For the internalization, the cells were grown in 35 mm glass bottom dishes (MatTek, Ashland, Mass., USA) with seeding at $1\times10^5$ cells in medium for 24 hrs. The RNAs were labeled with Cy3 using the Cy3 Silencer siRNA labeling kit (Ambion, TX, USA.). Cy3-labeled RNAs at 100 nM were added to the cells and incubated for 1 hour. The images were taken using a Zeiss LSM 510 Meta Inverted 2 photon confocal microscope system using a C-Apo 40x/1.2NA Water immersion objective.

For competition assays, 200 nM of Cy3 labeled P19 aptamer was used to compete with either unlabeled clones (1 µM). The fluorescence intensity was quantified in the presence of increasing amounts of competitors using confocal microscopy and analyzed statistically. One-way ANOVA was used for statistical significant analysis ($P<0.05$).

Binding Assay by Flow Cytometric Analysis

Aptamer binding and uptake was also assessed by flow cytometry. For the assay, cells were detached using a non-enzymatic cell dissociation solution, washed with PBS and suspended in binding buffer. Next, Cy3-labeled aptamers were added and incubated for 1 hours at 37° C. The binding of individual aptamers for the starting pool as a control to pancreatic cancer cells was performed in triplicate. Flow cytometry was performed on a Cyan (Beckman Coulter counter) and Fortessa. The data were analyzed with FlowJo software.

To determine the binding affinity of aptamers to Panc-1, the median fluorescence intensity (MFI) of each concentrations was determined and subtracted the mean fluorescence background of controls from the corresponding MFI of aptamers described by Sefah et al[53]. The dissociation constants were calculated using one site binding non-linear curve regression with a Graph Pad Prism (GraphPad Software, La Jolla, Calif., USA).

WST-1 Assay

Cell proliferation was quantified following four times treatment of P1 and P19 at 9 ug per treatment in Panc-1 ($2.5\times10^5$ cells), using WST-1 reagent following the manufacturer's guideline (Roche, UK). Briefly, the WST-1 reagent was used at 1:100 dilution to plates and incubated for one hour. The enzymatic reaction was measured at 450 ηm using Bio-Tek ELISA reader.

Aptamer-stick-saRNA

P1-stick, P19-stick, sense-stick and antisense were chemically synthesized by the Synthetic and Biopolymer Chemistry Core in the City of Hope). The P1-stick and P19-stick RNA was refolded in binding buffer, heated to 95° C. for 3 min and then slowly cooled to 37° C. The incubation was continued at 37° C. for 10 min. The sense-stick and antisense strand was annealed to the complementary partner using the same molar amounts as the corresponding partner strand to form the stick-C/EBPα RNAs or scramble RNA. The same amount of the refolded P1-stick and P19-stick was added and incubated at 37° C. for 10 min in binding buffer to form the P1 and P19 stick-C/EBPα RNAs or P1 and P19 stick-scramble RNA. Bold letters are stick sequences to anneal C/EBPα-saRNA or scramble RNA.

```
P19-stick: 5'-GGG AGA CAA GAA UAA ACG CUC AAU GGC

GAA UGC CCG CCU AAU AGG GCG UUA TGA CUU GUU GAG

UUC GAC AGG AGG CUC ACA ACA GGC ooo ooo o GU ACA

UUC UAG AUA CGC-3' (SEQ ID NO: 19 connected to SEQ

ID NO: 20 with carbon linker).
```

```
P1-stick: 5'-GGG AGA CAA GAA TAA ACG CUC AAU GCG

CUG AAU GCC CAG CCG UGA AAG CGU CGA UUU CCA UCC

UUC GAC AGG AGG CUC ACA ACA GGC ooo ooo o GU ACA

UUC UAG AUA CGC-3' (SEQ ID NO: 21 connected to SEQ

ID NO: 20 with carbon linker).
```

The symbol "ooo ooo o" refers to a carbon linker (e.g., $C_3$). Thus, in embodiments, the nucleic acid compound includes a chemical linker. In embodiments, the linker is substituted or unsubstituted alkylene. In embodiments, the linker is substituted or unsubstituted $C_1$-$C_{10}$ alkylene. In embodiments, the linker is unsubstituted $C_1$-$C_{10}$ alkylene. In embodiments, the linker is unsubstituted $C_1$-$C_5$ alkylene. In embodiments, the linker is unsubstituted $C_3$ alkylene.

Relative Gene Expression Analysis

In analysis the gene activation in cells by qPCR, the cells were grown in 6 wells with seeding at $1\times10^4$ cells in medium for 24 hrs. The P1 and P19 conjugates with C/EBPα-saRNA or scramble RNA RNAs treated at 80 nM every day for 3 days. At day of four, total RNA was extracted. RNA extracts were reverse transcribed using First strand cDNA synthesis kit (Invitrogen). The cDNA was then amplified for quantitative analysis of CEPBP-α (NM_007678) and the reference gene, gluceraldehyde-3-phosphate-dehydrogenase GAPDH (NM_008084, XM_001003314, XM_990238) using QuantiFast® SYBR® Green PCR Kit from Qiagen. To measure the gene expression in live cells, smart flare (Millipore) was used. Smart flare was loaded one day before treatment of the P19 conjugates at 100 nM. After taking images by confocal, quantify the intensity and normalized.

Anti-proliferation Assays In Vitro

Cell proliferation was quantified following four times treatment of P1 and P19 at 9 µg per treatment in Panc-1 ($2.5\times10^5$ cells), using WST-1 reagent following the manufacturer's guideline (Roche, UK). Briefly, the WST-1 reagent was used at 1:100 dilution to plates and incubated for one hour. The enzymatic reaction was measured at 450 ηm using Bio-Tek ELISA reader.

Human Pancreatic Cancer Specimens in Histological Quantification

The samples were stained by aptamer P1 and P19 respectively. We linked P1 and P19 with Cy3 as marker and DAPI stating was performed for cell nuclei as background. The sample sections were then examined under microscope at 100× magnification, and the aptamer content in each slide of pancreatic cancer was determined by measuring the average of positive-stained particle numbers in five independent fields randomly.

A total of 72 patients (45 male and 27 female) of pancreatic adenocarcinoma had undergone surgical intervention between January 2008 and December 2010 in National Taiwan University Hospital. Diagnosis was settled by pathologic analysis of specimen. All of the enrolled patients fulfilled the informed consent to receive the procedure, and this study was Institutional Review Board approved of NTUH.

In Vivo Assays of Anti-Tumor Effects

To establish the traceable tumor animal models, subcutaneous implantations were performed by injecting 25 µl of a monocellular suspension containing $10^6$ Panc-1 cell with luciferase expression (PANC-Luc) cells and a 25µ growth factor reduced matrigel matrix (BD Biosciences, USA) under the dorsal skin of 6-week-old female NOD/SCID mice (BioLasco Co., Taiwan).

The firefly luciferase fragment was inserted into the pcDNA-3.1(+) backbone encoding ampicillin resistance for selection in bacteria and neo gene for selection in mammalian cells. The recombinant constructs for stable cell line were purified using plasmid midi kit (QIAGEN, USA). PANC-1 cells were transfected with recombinant constructs for 24 h. The following day, culture medium was replaced with standard medium containing 1.2 mg/mL G418 (Merck, Germany) for stable clone selection. Two weeks after selection, single stable cell line was picked and maintained in medium containing 1.2 mg/mL G418. Luciferase expression was assessed using the Luciferase Assay System. Tumors developed to about 1×1 cm in approximately 3 weeks after inoculation.

Seven mice in each subgroup were injected with 100 pmol, 250 pmol or 1 nmol aptamer-stick-saRNA via tail vein 4 times/week for 3-4 weeks and sacrificed one week after last injection. Tumor growth was monitored by evaluating bioluminescence using the spectrum of IVIS 200 before first injection and one week after last injection. Prior to the in vivo imaging, the mice were anesthetized using isoflurane. A solution of 150 µg/kg D-luciferin (Biosynth, USA) was then injected by the intraperitoneal route. The mice were imaged in the spectrum of IVIS 200 and bioluminescent signals were analyzed using Living Image Software (Caliper Life Sciences, Alameda, Calif.). Tumor size was measured by ruler and calculated by the formula 0.52*length*width*width For gemcitabine resistant tumour test, twelve 5-weeks-old female NOD/SCID mice were injected subcutaneously (S.C.) on the flank with $2.8 \times 10^6$ AsPC-1 pancreatic cancer cells in 0.05 ml PBS with 0.15 ml matrigel. After 3 weeks, mice were divided into four groups. One group served as untreated controls and the others injected with P1 (10 ug per injection), P19 (10 ug per injection) and P1 combined with P19 (5 ug of P1 with 5 ug of P19 per injection). Aptamer were injected through tail vein. Animals were injected 4 times at days 1, 3, 5, and 7, and were sacrificed at day 9.

Target Protein Identification and Validation

P1 and P19 were labeled with biotin at the 3' end. Target membrane proteins were isolated following procedures described by Daniels et al[26] or extracted by ProteoExtract Native Membrane protein Extraction Kit (Calbiochem). Agilent 6520 Q-TOF mass spectrometer used to identify aptamer retrieved proteins. A BIAcore T100 (GE Healthcare, Uppsala, Sweden) was used to measure binding by surface plasmon resonance (SPR) technique. BIAevaluation software (GE Healthcare) was used for analysis. Gel shift assay was also performed to validate the target ligand binding.

Statistical Analysis

Statistical significant differences were determined by Student's t-test or one-way ANOVA test using Graph Pad Prism software (GraphPad Software, La Jolla, Calif., USA.

Example 2

Determine the Effect of Anti-Hsp70 RNA Aptamers in Mitochondria Apoptosis

The up-to-date data indicate that cancer cells become 'addicted' to Hsp70 through chaperone's activity on multiple survival pathways, specifically cancer specific features such as hypoxia, oxidative stress, and altered pH. The overexpression of Hsp70 in pancreatic adenocarcinoma increases tumorgenicity and inhibit apoptosis (Aghdassi, Phillips et al. 2007). Hsp70 is constitutively expressed on cell surface of human tumor, not normal cells (Hantschel, Pfister et al. 2000, Shin, Wang et al. 2003). The translocalization of Hsp70 on the cancer cell surface and organelle distribution is related to their specific lipid compositions (Arispe, Doh et al. 2004, Gehrmann, Liebisch et al. 2008, Mahalka, Kirkegaard et al. 2014). Interestingly, silencing of Hsp70 with antisense results in massive death of cancer cells, whereas non-cancer cells are not affected (Nylandsted, Rohde et al. 2000). Inhibition of Hsp70 is independent of classical apoptosis pathway such as Bcl-2 and Bcl-$X_L$ (Nylandsted, Rohde et al. 2000). Its high expression in tumors correlates with therapy resistance and poor prognosis (Sliutz, Karlseder et al. 1996, Elpek, Karaveli et al. 2003). Hsp70 promotes chemoresistance by blocking Bax mitochondrial translocation, pro-apoptotic protein of the mitochondria apoptosis (Yang, Wang et al. 2012). Hsp70 indirectly blocks apoptotic pathways at premitochondrial and mitochondrial level, and a post-mitochondrial stage (Garrido, Brunet et al. 2006). Hsp70 also protects mitochondrial from damage by oxidative stress (Polla, Kantengwa et al. 1996). Hsp70 plays important role in the assembly of the cytochrome c oxidase, mitochondria transmembrane protein (Bottinger, Guiard et al. 2013).

Cancer cells acquiring mitochondria from endothelial display chemoresistance, implicating chemoresistance linked to mitochondria (Pasquier, Guerrouahen et al. 2013). Therefore, mitochondria are gatekeeper of response to chemotherapy and good target to reduce chemoresistance. The most differentially expressed mitochondrial proteins between normal and cancerous cells are cytochrome oxidase and hsp70 (Chen, Chou et al. 2011, Bottoni, Giardina et al. 2012). Mitochondria is the cellular powerhouses, primary source of energy. Because cancer cells are demanding high energy, they are much more dependent to mitochondria than normal cells. Peptide targeting hsp70 is sensitizing to apoptotic cell death (Rerole, Gobbo et al. 2011). In our preliminary data above specific aim 1, the aptamer binding ligands expressed on cell surface were identified tumor associated Hsp70. Herein, it is necessary to inhibit hsp70 function to induce mitochondria apoptosis affecting cancer cells specifically and to diminish chemoresistance.

Herein the effect of anti-Hsp70 RNA aptamers in chemoresistance is determined. We will test the working hypothesis that anti-Hsp70 RNA aptamer induce mitochondrial apoptosis. We will test our working hypothesis by using the approach of mitochondrial apoptotic proteins release by immunoblotting, mitochondrial morphology by TEM, mitochondrial metabolomic analysis, and cytochrome C (COX)

activity assays. Because cancer cells are addicted to hsp70, functional inhibition of hsp70 is limited in cancers, not affected in normal cells. It brings to reduce cytotoxicity in normal cells.

Figure 6:
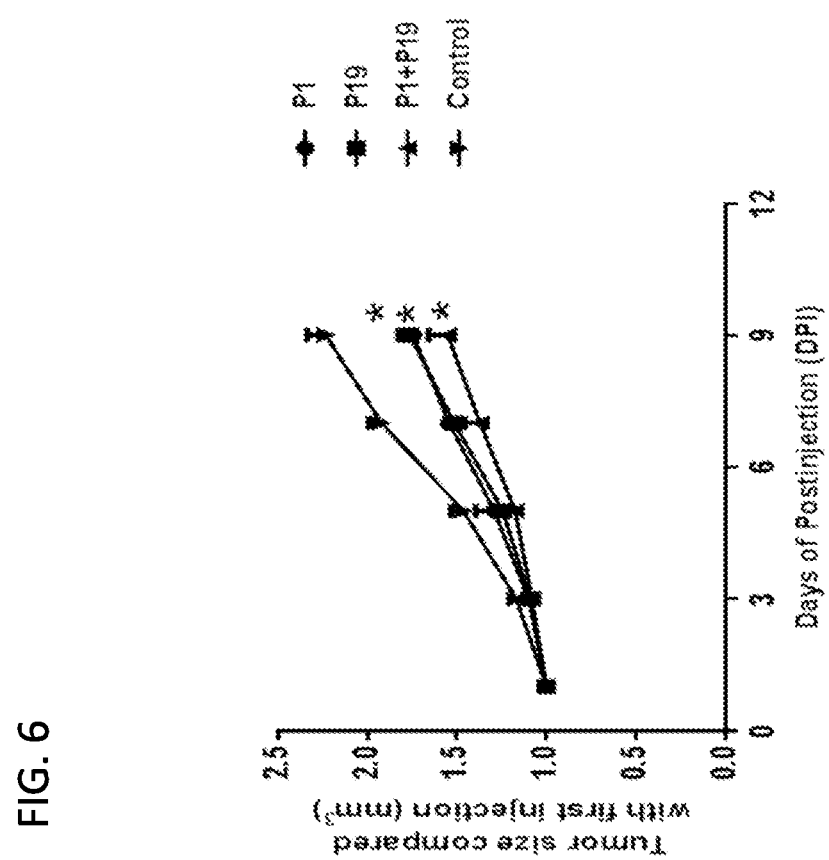
FIG. 6. In vivo assays. For gemcitabine resistant tumor test, ASPC-1 pancreatic cancer cells were engrafted in 5-weeks-old female NOD/SCID mice. After engraftment, aptamer were treated through tail vein. * t-test: P value<0.05.

To test chemoresistant tumor regression in mice, twelve 5-weeks-old female NOD/SCID mice were injected subcutaneously (S.C.) on the flank with 2.8×10$^6$ASPC-1 gemcitabine resistant pancreatic cancer cells in 0.05 ml PBS with 0.15 ml matrigel. After 3 weeks, mice were divided into four groups. One group served as untreated controls and the others injected with P1, P19 and P1 combined with P19. Aptamer were injected through tail vein Animals were injected 4 times at days 1, 3, 5, and 7, and were sacrificed at day 9. Comparing control, significant tumor growth inhibition showed in aptamer treated group (FIG. 6).

We will measure mitochondrial apoptosis by anti-hsp70 RNA aptamer. To doing so, we measure the release of mitochondrial apoptotic proteins such as Cytochrome C, Smac/DIABLO, HtrA2/Omi and AIF from mitochondrial fractionations by standard immune blotting procedure after treatment of anti-hsp70 RNA aptamer. Mitochondrial morphology changes will be performed by TEM (Transmission Electron Microscopy). To measure mitochondria metabolomics, oxygen consumption and glycolytic capacity by oxidative phosphorylation (OXPHOS) inhibition will be measured XF analyzer (Seahorse Bioscience) with or without oligomycin and anti-hsp70 RNA aptamer for real time metabolic analysis. Briefly, cells will be plated into XF96 cell culture microplates before the experiment. To measure the response to PXHPOS inhibition, oligomycine (positive control) and anti-hsp70 RNA aptamer(test material) and rotenone(XF Cell Mito Stress kit, Seahorse Bioscience) will be sequentially injected. To measure extracellular acidification rate(ECAR) and lactate production, cells will be plated in base assay. Glucose, oligomycin, anti-hsp70 RNA aptamer, and 2-deoxy-glucose will be sequentially injected (XF Glycolysis stress test kit, Seahorse Bioscience). Experiments will run using a XF96 analyzer and raw data will be normalized to metabolically active cells, evaluated Hoechst 33342 positive/propidium iodide (PI) negative by imaging system immediately after each experiment. As an alternative way, lactate ELISA kit will be used. In response to OXPHOS suppression, cells increase their glucose uptake and glycolysis activity to maintain the intracellular level of ATP. The components of glycolysis and OXPHOS in the bioenergetic constitution will be calculated. To quantify ATP present, an indicator of metabolically active cells, CellTiter Glo luminescent cell viability assays will be used following manufacture's instruction (Promega). Cytochrome C (COX) activity is assayed calorimetrically.

Example 3

Figure 14B:
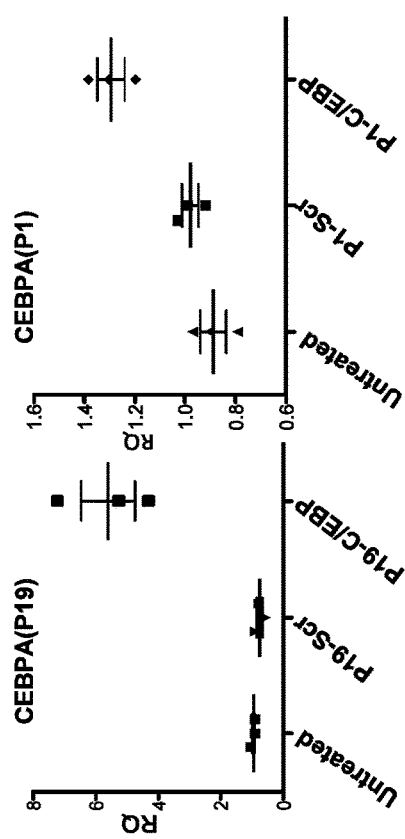
FIG. 14A-14E: Internalization and biological effects of conjugated aptamers in PANC-1 cells.
Figure 14D:
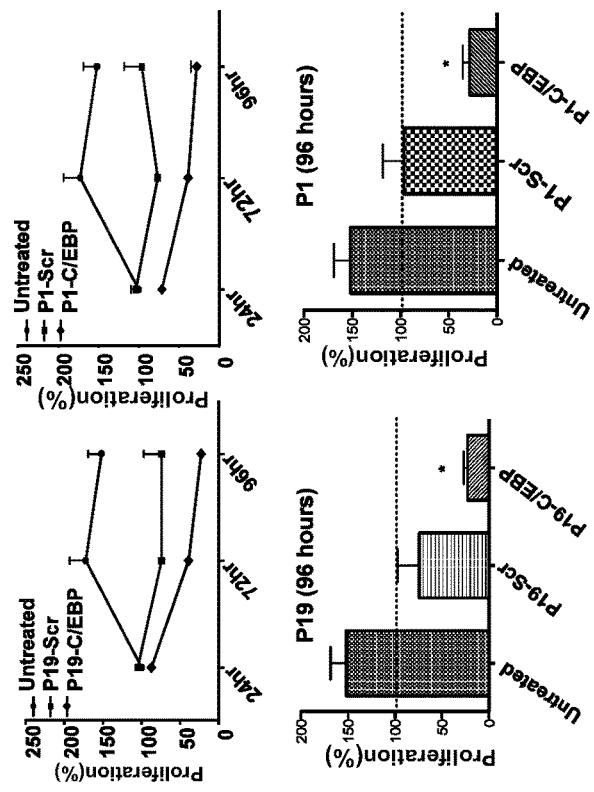
Figure 14A:
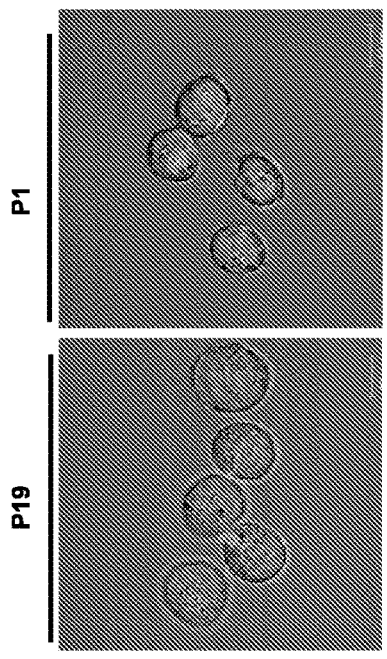
Figure 14C:
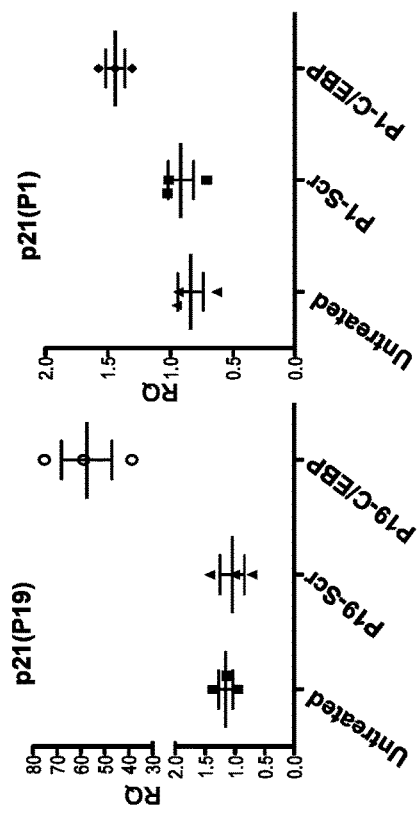
Figure 14E:
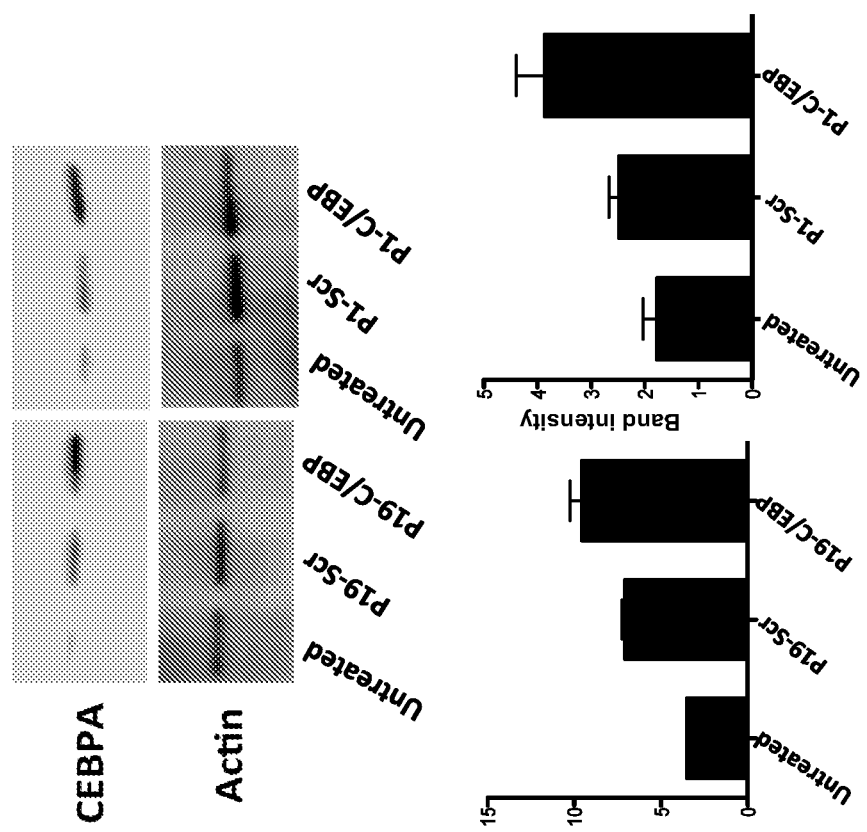
Figures 15A, 15B:
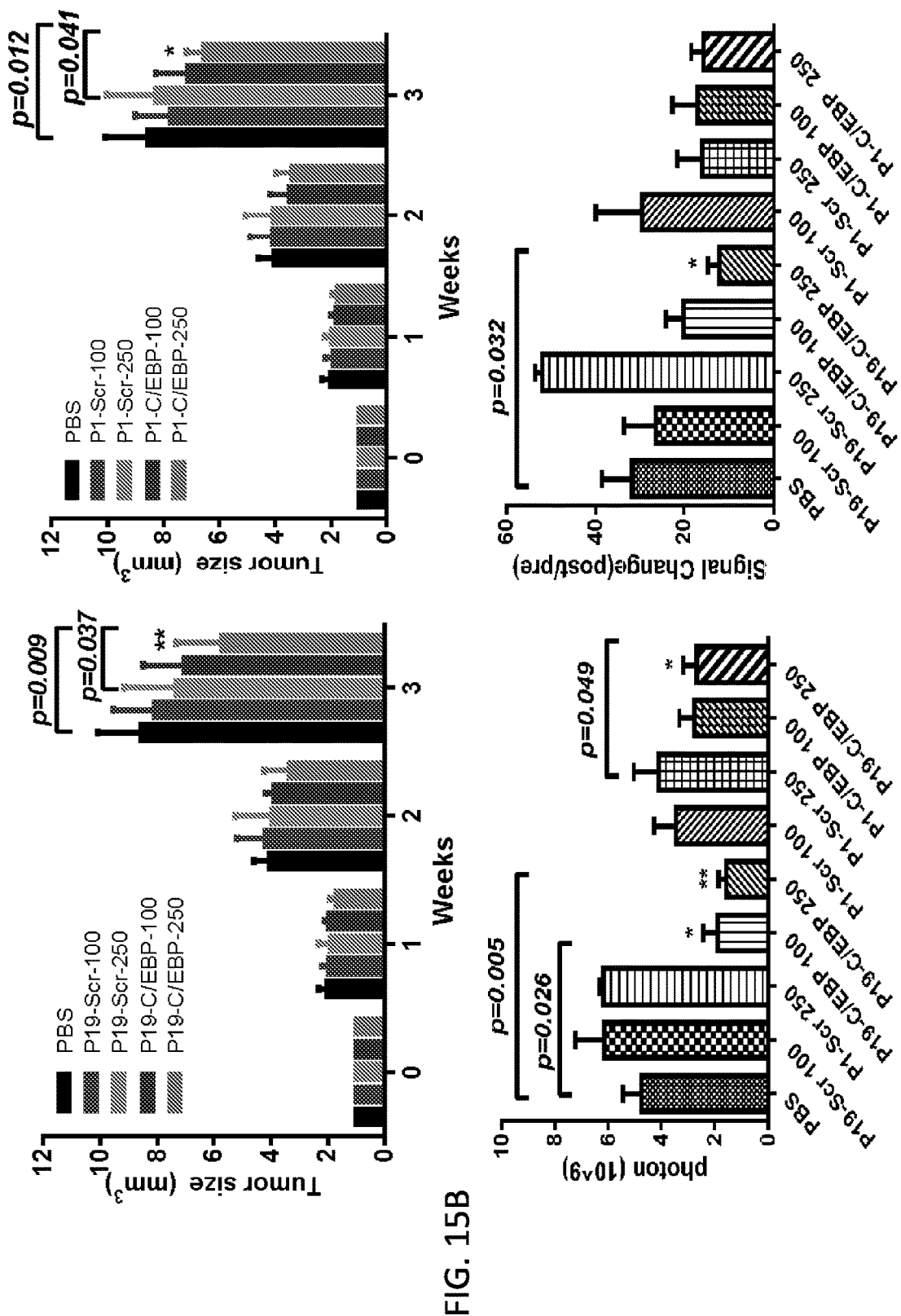
FIG. 15A-15B: In vivo effects of P19 and P1-C/EBPα-saRNA.
Figure 16:
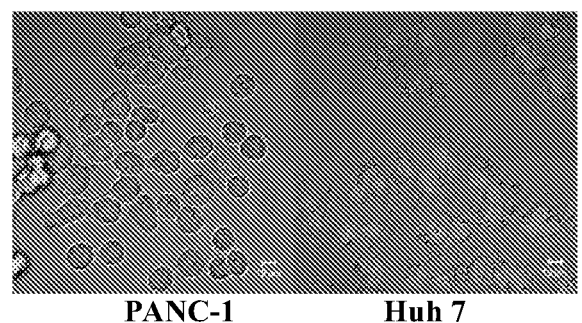
FIG. 16: Internalization assay of RNA aptamer library in PANC-1 and Huh7. Cy3-labeled RNA aptamer library at 100 nM were assessed in PANC-1 and control Huh7 cells by confocal microscopy after 1 hour incubation. Blue: Hoechst 33342. Scale bar: 10 μm
Figure 17:
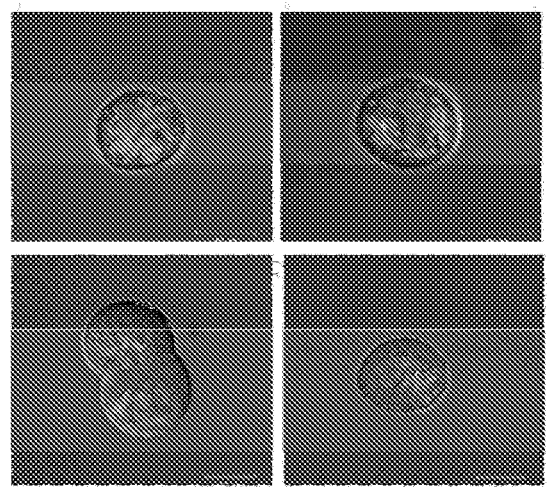
FIG. 17: Internalization in various pancreatic cancer cell lines. The pancreatic cell lines BxPC-3 and CFPAC-1 were treated with 100 nM of the Cy3-labeled P19 and P1 aptamer and analyzed by confocal microscopy. Blue: Hoechst 33342. Scale bar: 10 μm
Figure 18A:
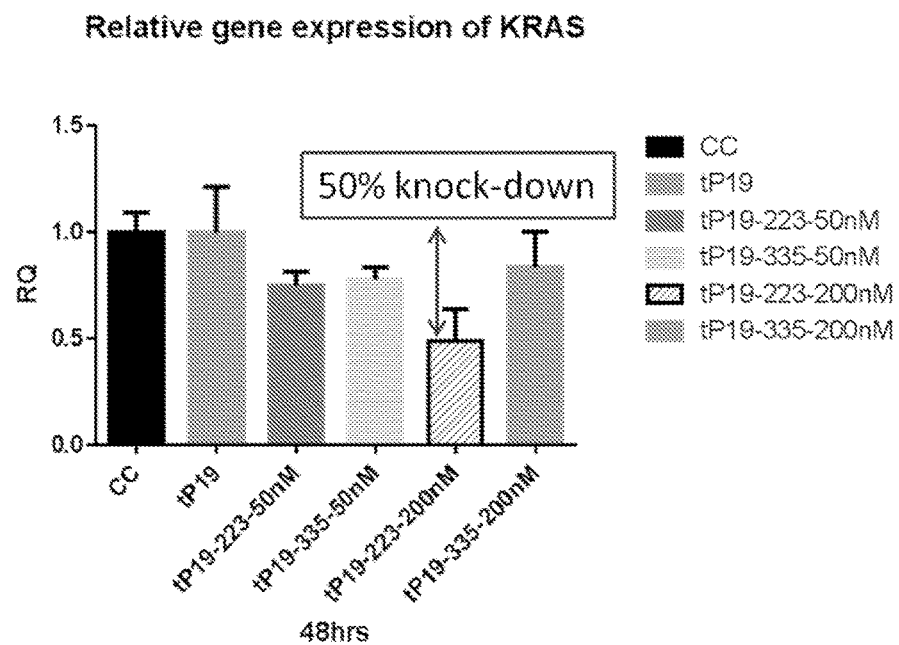
FIG. 18A-18C: Relative transcript expression (qPCR) for KRAS and PDL1 mRNA (FIG. 18A) KRAS mRNA was quantified by real-time PCR. KRAS expression decreased 50% at 48 hours at 200 nM by tP19-KRAS-234 siRNA. ΔΔCt method was used to calculate gene expression. HPRT was used to normalization.
Figure 18B:
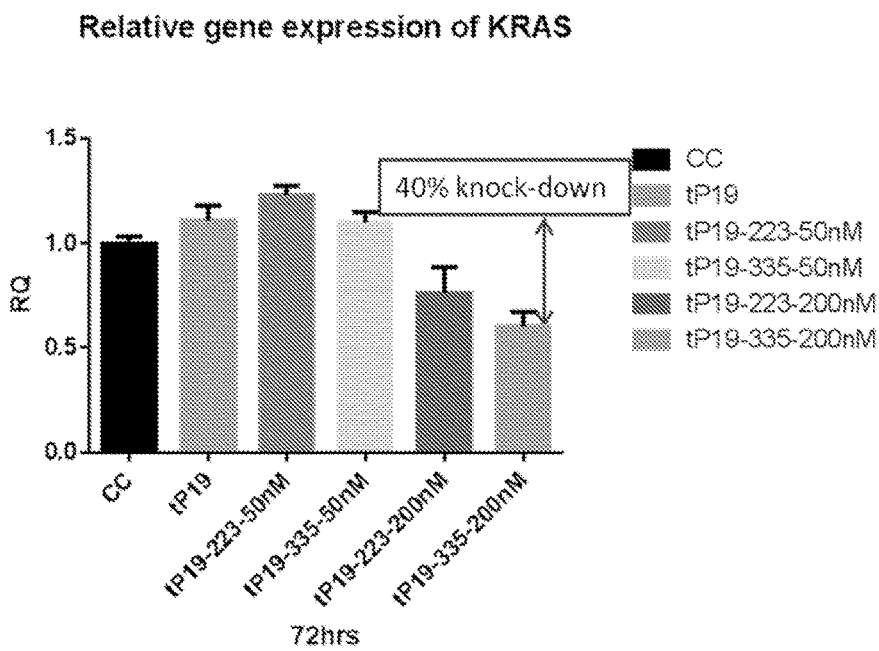
Figure 18C:
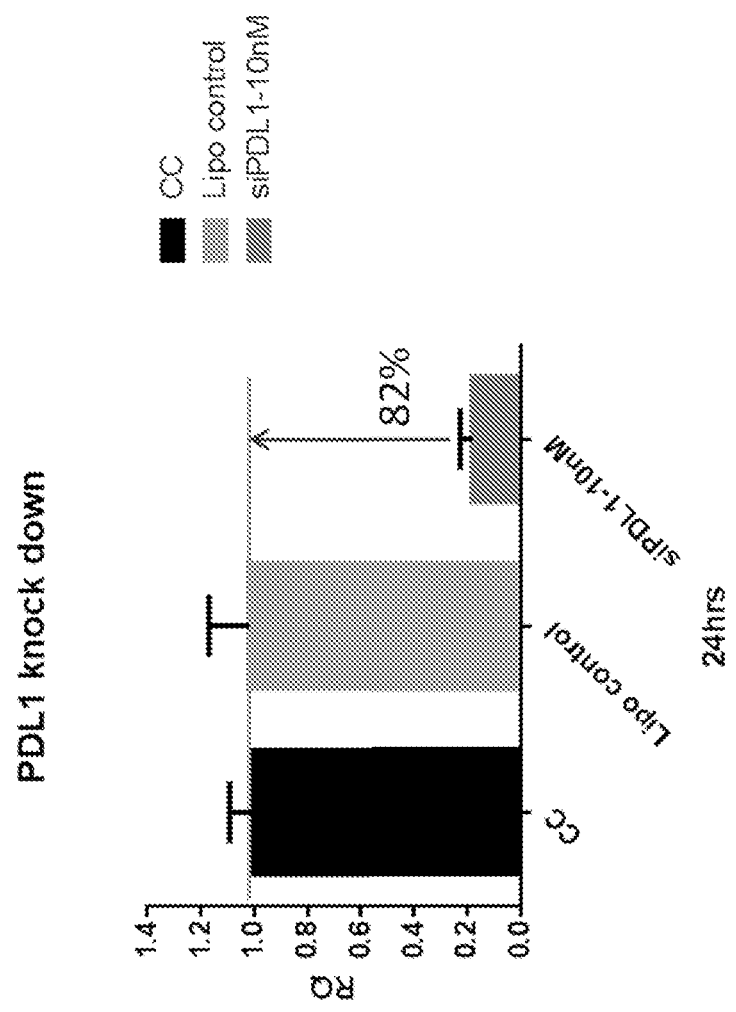

C/EBPα-conjugated P19 and P1 demonstrate strong anti-proliferation in cultured cells. Since downregulation of C/EBPα has been previously reported to result in the formation of pancreatic intraepithelial neoplasms, (14) we designed a conjugated P19 and P1 aptamer with C/EBPα-saRNA to exploit targeted delivery of the saRNA into pancreatic cancer cells for activation of C/EBPα. In order to maintain functional integrity of the molecule we placed 'sticky sequences' (a sequence of 16 nucleotides that prevent structural hindrance) between the P19/P1 aptamer and either C/EBPα or a scrambled saRNA oligonucleotide. The P19 and P1 conjugates showed successful PANC-1 internalization (FIG. 14A). To investigate gene activation in vitro, the P19 and P1 conjugated C/EBPα-saRNA or scrambled RNAs were added to PANC-1 cell culture media in the absence of any transfection reagent. Cells treated with the conjugated C/EBPα-saRNA aptamers showed significantly higher levels of C/EBPα mRNA (FIG. 14B) and its downstream target, p21 (FIG. 14C) when compared to a scrambled-saRNA. The P19-C/EBPα-saRNA construct induced a 5-fold increase in C/EBPα transcript (p=0.029) and a 50 fold increase in p21 transcript level ((p=0.03), two-tailed T-test with Welch's correction at 95% confidence interval), Table 2. P1-C/EBPα-saRNA construct induced a 1.3-fold increase in C/EBPα transcript (p=0.01) and a 1.4 fold increase in p21 transcript level ((p=0.026), two-tailed T-test with Welch's correction at 95% confidence interval), Table 2. Since C/EBPα is known to stabilize the cyclin-dependent kinase inhibitor, p21 to elevate expression levels and block cyclin-dependent kinases for cell cycle arrest28; we performed a WST-1 cell proliferation assay on PANC-1 cells treated with the conjugated aptamers for 96 hours. We observed over 80% reduction in cell proliferation following treatment with either P19-C/EBPα-saRNA (FIG. 3d, left panel) or P1-C/EBPα-saRNA (FIG. 14D, right panel); (p=0.011, paired T-test at 5% confidence interval) (Table 3). A Western blot analysis of CEBPA protein extracted from the treated PANC-1 cells demonstrated 3 times higher band intensity in cells treated with P19-C/EBPα-saRNA when compared to P1-C/EBPα-saRNA (FIG. 14E and Table 4). We also observed at least a 2 fold increase in CEBPA signal from cells treated with scramble conjugated aptamer (FIG. 14E and Table 4). Since the P19/P1 aptamer target is linked with the c-Myc/CEBPA signaling network 29, the aptamers may be modulating a functional effect within this network which may not be picked up at the transcript level, but clearly observable at the protein level and from the WST assay where P19/P1-scramble conjugate showed a cytostatic response (FIG. 14D).

Example 4

Materials and Methods and Sequences
tP19 sticky sequence to conjugates to siKRAS:
5'-CUCAAUGGCGAAUGCCCGCCUAAUAGGGooooooooAGUUUUUUACAU UUUG-3' (SEQ ID NO: 1 connected to SEQ ID NO: 9 with carbon linker).

siKRAS-234
siKRAS 234 Sense with sticky:
5'-UGAAUUAGCUGUAUCGUCAAGGooooooCAAAAUGUAAAAAACU-3'

(SEQ ID NO: 13 connected to SEQ ID NO: 10 with carbon linker).

siKRAS-234 AS:
5'-UUGACGAUACAGCUAAUUCAUA-3' (SEQ ID NO: 14)

siKRAS-355:
siKRAS-335 Sense strand with sticky:
5'-ACUGUACUCCUCUUGACCUGCUooooooCAAAAUGUAAAAAACU-3'

(SEQ ID NO: 15 connected to SEQ ID NO: 10 with carbon linker).

```
siKRAS-355 Anti-sense strand:
CAGGUCAAGAGGAGUACAGUUA (SEQ ID NO: 16).

tP19 with sticky sequence to conjugate siPDL1
5'-CUCAAUGGCGAAUGCCCGCCUAAUAGGGooooooooGGAUGGAUGGAU GGUA-3' (SEQ ID NO: 1 connected to SEQ ID NO: 11 with carbon linker).

siPDL1 sense with sticky:
5'-GAAGCAAAGUGAUACACAUUUoooooUACCAUCCAUCCAUCC-3'

(SEQ ID NO: 17 connected to SEQ ID NO: 12 with carbon linker).

siPDL1 Anti-sense strand:
5'-AUGUGUAUCACUUUGCUUCUU-3' (SEQ ID NO: 18).

Bold letters are stick sequences to anneal KRAS-
siRNA or PDL1-siRNA
o: C3 carbon linker.
```

Aptamer conjugate to saRNA using 'sticky sequences' (STICK). tP19-STICK, Sense-STICK and antisense RNAs of KRAS and PDL1 were chemically synthesized by the Synthetic and Biopolymer Chemistry Core in the City of Hope. The tP19-STICK RNAs were refolded in binding buffer, heated to 95° C. for 3 min, and then slowly cooled to 37° C. The incubation was continued at 37° C. for 10 min. The sense-STICK and antisense strand of KRAS and PDL1 were annealed to the complementary partners using the same molar amounts as the corresponding partner strand to form the STICK-KRAS siRNAs and STICK-PDL1 siRNAs.

Relative gene expression analysis by qPCR and protein expression by Western blot analysis. For analyzing gene silencing, PANC-1 cells were seeded into 12-well plates at a density of 5×104 cells per well. tP19 and conjugated with KRAS-siRNAs or PDL1-siRNAs, were added directly to the cells, in duplicate, at a final concentration of 50 nM or 200 nM, for RNA extraction. The treatment was repeated 24 hours later and the cells were harvested at the 48 hour and 72 hour time point. The total RNA was extracted for reverse transcription and target cDNA amplification by real-time PCR. ΔΔCt method was used to calculate gene expression analysis.

Before to make the conjugate with tP19, siPDL1 was designed and tested the silencing effect in PANC-1. PANC-1 cells were seeded into 12-well plates at a density of 5×104 cells per well. PDL1-siRNAs were added to the cells, in duplicate, at a final concentration of 10 nM with lipofectamin 2000. The cells were harvested at the 24 hour time point for RNA extraction. The total RNA was extracted for reverse transcription and target cDNA amplification by real-time PCR. ΔΔCt method was used to calculate gene expression analysis.

Tables

TABLE 1

The alignment and identification of RNA aptamers After 14 rounds of selection, the sequences of 47 clones were identified and the frequencies of two aptamer clones are shown.

| Name | Sequences | Frequency (%) |
|---|---|---|
| P19 | GGGAGACAAGAAUAAACGCUCAAUGGC GAAUGCCCGCCUAAUAGGGCGUUAUGA CUUGUUGAGUUCGACAGGAGGCUCACA ACAGGC (SEQ ID NO: 2) | 13(6/47) |
| P1 | GGGAGACAAGAAUAAACGCUCAAUGCA GCUGAAUGCCCAGCCGUGAAAGCGUCG AUUUCCUCCUUCGACAGGAGGCUCACA ACAGGC (SEQ ID NO: 4) | 13(6/47) |

TABLE 2

Statistical analysis of CEBPA and p21 transcript levels.

| | CEBPA mRNA | | p21 mRNA | |
|---|---|---|---|---|
| Table Analyzed | CEBPA(P1) | CEBPA(P19) | CEBPA(P1) | CEBPA(P19) |
| Column B | P1-Scr | P19-Scr | P1-Scr | P19-Scr |
| vs | vs | vs | vs | vs |
| Column C | P1-CEBPA | P19-CEBPA | P1-CEBPA | P19-CEBPA |
| Unpaired t test with Welch's correction | | | | |
| P value | 0.015 | 0.0297 | 0.0262 | 0.0333 |
| P value summary | * | * | * | * |
| Are means signif. Different?(P < 0.05) | Yes | Yes | Yes | Yes |
| One- or Two-tailed P value? | Two-tailed | Two-tailed | Two-tailed | Two-tailed |
| Welch-corrected t, df | T = 5.043, df = 3 | T = 5.671, df = 2 | T = 4.101, df = 3 | T = 5.343, df = 2 |
| How big is the difference? | | | | |
| Mean ± SEM of column B | 0.9794 ± 0.03213, N = 3 | 0.7549 ± 0.09829, N = 3 | 0.9170 ± 0.1015, N = 3 | 1.050 ± 0.2052, N = 3 |
| Mean ± SEM of column C | 1.296 ± 0.05385, N = 3 | 5.617 ± 0.8516, N = 3 | 1.422 ± 0.07790, N = 3 | 57.62 ± 10.58, N = 3 |
| Difference between means | −0.3162 ± 0.06270 | −4.862 ± 0.8573 | −0.5246 ± 0.1279 | −56.57 ± 10.58 |
| 95% confidence interval | −0.5157 to −0.1167 | −8.550 to −1.173 | −0.9316 to −0.1176 | −102.1 to −11.03 |
| R squared | 0.8945 | 0.9415 | 0.8486 | 0.9346 |

TABLE 3

Table summary of percentage cell proliferation in PANC1 cells treated with P19/P1 scramble and CEBPA at 96 hours

|  | Untreated | P19-Scr | P19-CEBPA | P1-Scr | P1-CEBPA |
|---|---|---|---|---|---|
| Number of values | 3 | 3 | 3 | 3 | 3 |
| 25% Percentile | 118.4 | 50.53 | 16.99 | 72.8 | 19.59 |
| Median | 165.2 | 51.65 | 21.71 | 75.88 | 21.52 |
| 75% Percentile | 172.4 | 120 | 30.13 | 140.3 | 43.04 |
| Mean | 152 | 74.07 | 22.94 | 96.34 | 28.05 |
| Std. Deviation | 29.34 | 39.82 | 6.66 | 38.13 | 13.02 |
| Std. Error | 16.94 | 22.99 | 3.84 | 22.01 | 7.516 |
| Lower 95% CI of mean | 79.1 | −24.84 | 6.41 | 1.62 | −4.29 |
| Upper 95% CI of mean | 224.9 | 173 | 39.48 | 191.1 | 60.39 |
| Sum | 455.9 | 222.2 | 68.83 | 289 | 84.15 |

TABLE 4

Table summary of band intensity from Western blot on PANC cells treated with P19/P1 scramble and CEBPA

|  | P19-CEBPA ||| P1-CEBPA |||
|---|---|---|---|---|---|---|
|  | Untreated | P19-Scr | P19-CEBPA | Untreated | P1-Scr | P1-CEBPA |
| Number of values | 3 | 3 | 3 | 3 | 3 | 3 |
| Minimun | 3.46 | 6.12 | 8.57 | 1.30 | 2.05 | 3.3 |
| Median | 3.49 | 6.44 | 9.25 | 1.84 | 2.22 | 3.38 |
| Maximun | 3.57 | 6.92 | 10.88 | 2.20 | 2.37 | 4.93 |
| Mean | 3.51 | 6.50 | 9.56 | 1.78 | 2.21 | 3.87 |
| Std. Deviation | 0.056 | 0.40 | 1.19 | 0.45 | 0.16 | 0.92 |
| Std. Error | 0.03 | 0.23 | 0.68 | 0.26 | 0.09 | 0.53 |
| Lower 95% CI of mean | 3.37 | 5.50 | 6.62 | 0.65 | 1.83 | 1.59 |
| Upper 95% CI of mean | 3.64 | 7.49 | 12.51 | 2.90 | 2.60 | 6.14 |
| Sum | 10.52 | 19.48 | 28.69 | 5.34 | 6.64 | 11.6 |

TABLE 5

Scoring criteria for P19 and P1 immunohistochemistry.

|  | P19 ||| P1 |||
|---|---|---|---|---|---|---|
|  | Low (<7) | Medium (>7 and <14) | High (>14 and <20) | Low (<7) | Medium (>7 and <14) | High (>14 and <20) |
| No. of Patients | 3 | 26 | 43 | 3 | 26 | 43 |
| Survival Period | 21.0 ± 2.64 | 15.6 ± 3.30* | 13.0 ± 4.29** | 21.0 ± 2.64 | 15.9 ± 3.17* | 13.1 ± 4.36** |

Scoring criteria were established for the staining intensity of the 72 patient samples: low, medium, and high.
Mean ± SD.
*p < 0.05;
**p < 0.005 when compared to low staining group

TABLE 6

SELEX condition

| SELEX rounds | Positive cells | Negative cells | RNA pool Con | Yeast tRNA Con (ug/ml) | BSA Con | Sperm DNA (ug/ml) | Washing numbers | Incubation time |
|---|---|---|---|---|---|---|---|---|
| 1 | 3 × 10⁶ cells | — | 6 nmol | 100 | 0.01% | — | 3 | 1 hour |
| 2 | 3 × 10⁶ cells | — | 1 nmol | 100 | 0.01% | — | 3 | 1 hour |
| 3 | 3 × 10⁶ cells | 3 × 10⁶ cells | 1 nmol | 100 | 0.01% | 1 | 3 | 1 hour |
| 4 | 3 × 10⁶ cells | 3 × 10⁶ cells | 1 nmol | 100 | 0.01% | 1 | 3 | 1 hour |
| 5 | 1 × 10⁶ cells | — | 600 pmol | 100 | 0.01% | 50 | 4 | 30 min |
| 6 | 1 × 10⁶ cells | 1 × 10⁶ cells | 600 pmol | 100 | 0.01% | 50 | 4 | 30 min |
| 7 | 1 × 10⁶ cells | 1 × 10⁶ cells | 600 pmol | 100 | 0.01% | 50 | 4 | 30 min |

TABLE 6-continued

| SELEX rounds | SELEX condition | | | | | | | |
|---|---|---|---|---|---|---|---|---|
| | Positive cells | Negative cells | RNA pool Con | Yeast tRNA Con (ug/ml) | BSA Con | Sperm DNA (ug/ml) | Washing numbers | Incubation time |
| 8 | 5 × 10⁵ cells | — | 600 pmol | 100 | 0.01% | 50 | 5 | 20 min |
| 9 | 5 ×10⁵ cells | 1 × 10⁶ cells | 600 pmol | 100 | 0.01% | 50 | 5 | 20 min |
| 10 | 5 × 10⁵ cells | 1 × 10⁶ cells | 600 pmol | 100 | 0.01% | 50 | 5 | 20 min |
| 11 | 3 × 10⁵ cells | — | 600 pmol | 100 | 0.01% | 50 | 6 | 10 min |
| 12 | 3 × 10⁵ cells | 5 × 10⁵ cells | 600 pmol | 100 | 0.01% | 50 | 6 | 10 min |
| 13 | 3 × 10⁵ cells | 5 × 10⁵ cells | 600 pmol | 100 | 0.01% | 50 | 6 | 10 min |
| 14 | 5 × 10⁵ cells | 5 × 10⁵ cells | 600 pmol | 100 | 0.01% | 50 | 6 | 20 min |

TABLE 7

Sequence information of P19, P1 aptamers and Sense + antisense strand of CEBPA saRNA

| Name | Sequences |
|---|---|
| P19-stick | 5'-GGGAGACAAGAAUAAACGCUCAAUGGCGAAU GCCCGCCUAAUAGGGCGUUAUGACUUGUUGAGUU CGACAGGAGGCUCACAACAGGCoooooooGUACA UUCUAGAUACGC-3' (SEQ ID NO: 19 connected to SEQ ID NO: 20 with carbon linker) |
| P1-stick | 5'-GGGAGACAAGAAUAAACGCUCAAUGCGCUGA AUGCCCAGCCGUGAAAGCGUCGAUUUCCAUCCUU CGACAGGAGGCUCACAACAGGCoooooooGUACA UUCUAGAUACGC-3' (SEQ ID NO: 21 connected to SEQ ID NO: 20 with carbon linker) |
| AW1 Sense | CGGUCAUUGUCACUGGUCAUU (SEQ ID NO: 22) |
| AW1 Antisense | UGACCAGUGACAAUGACCGUU (SEQ ID NO: 23) |

INFORMAL SEQUENCE LISTING

SEQ ID NO: 1 (truncated P19):
CUCAAUGGCGAAUGCCCGCCUAAUAGGG

SEQ ID NO: 2 (full length P19):
GGGAGACAAGAAUAAACGCUCAAUGGCGAAUGCCCGCCUAAUAGGGCGUU
AUGACUUGUUGAGUUCGACAGGAGGCUCACAACAGGC SEQ ID NO: 3 (P15):
GGGAGACAAGAAUAAACGCUCAAAGUUGCGGCCCAACCGUUUAAUUCAGA
AUAGUGUGAUGCCUUCGACAGGAGGCUCACAACAGGC SEQ ID NO: 4 (P1):
GGGAGACAAGAAUAAACGCUCAAUGCGCUGAAUGCCCAGCCGUGAAAGCG
UCGAUUUCCAUCCUUCGACAGGAGGCUCACAACAGGC SEQ ID NO: 5 (P11):
GGGAGACAAGAAUAAACGCUCAAAUGAUUGCCCAUUCGGUUAUGCUUGCG
CUUCCUAAAGAGCUUCGACAGGAGGCUCACAACAGGC SEQ ID NO: 6 (P7):
GGGAGACAAGAAUAAACGCUCAAGGCCAUGUUGAAUGCCCAACUAAGCUU
UGAGCUUUGGAGCUUCGACAGGAGGCUCACAACAGGC

INFORMAL SEQUENCE LISTING

SEQ ID NO: 7 (P6):
GGGAGACAAGAAUAAACGCUCAACAAUGGAGCGUUAAACGUGAGCCAUUC
GACAGGAGGCUCACAACAGGC

SEQ ID NO: 8:
GAAUGCCC

REFERENCES

1. Jemal, A. et al. Cancer statistics, 2009. *CA Cancer J Clin* 59, 225-249 (2009).

2. Stathis, A. & Moore, M. J. Advanced pancreatic carcinoma: current treatment and future challenges. _u Nature reviews. Clinical oncology 7, 163-172 (2010).

3. Pancreatic cancer in the UK. *Lancet* 378, 1050 (2011).

4. Klinkenbijl, J. H. et al. Adjuvant radiotherapy and 5-fluorouracil after curative resection of cancer of the pancreas and periampullary region: phase III trial of the EORTC gastrointestinal tract cancer cooperative group. *Annals of surgery* 230, 776-782; discussion 782-774 (1999).

5. Neoptolemos, J. P. et al. A randomized trial of chemoradiotherapy and chemotherapy after resection of pancreatic cancer. *The New England journal of medicine* 350, 1200-1210 (2004).

6. Oettle, H. et al. Adjuvant chemotherapy with gemcitabine vs observation in patients undergoing curative-intent resection of pancreatic cancer: a randomized controlled trial. *JAMA: the journal of the American Medical Association* 297, 267-277 (2007).

7. Vincent, A., Herman, J., Schulick, R., Hruban, R. H. & Goggins, M. Pancreatic cancer. *Lancet* 378, 607-620 (2011).

8. Alexakis, N. et al. Current standards of surgery for pancreatic cancer. *The British journal of surgery* 91, 1410-1427 (2004).

9. Ghaneh, P., Costello, E. & Neoptolemos, J. P. Biology and management of pancreatic cancer. *Gut* 56, 1134-1152 (2007).

10. Guidelines for the management of patients with pancreatic cancer periampullary and ampullary carcinomas. *Gut* 54 Suppl 5, v1-16 (2005).

11. Cunningham, D. et al. Phase III randomized comparison of gemcitabine versus gemcitabine plus capecitabine in patients with advanced pancreatic cancer. *Journal of clinical oncology: official journal of the American Society of Clinical Oncology* 27, 5513-5518 (2009).

12. Heinemann, V., Haas, M. & Boeck, S. Systemic treatment of advanced pancreatic cancer. *Cancer treatment reviews* 38, 843-853 (2012).

13. Wong, H. H. & Lemoine, N. R. Pancreatic cancer: molecular pathogenesis and new therapeutic targets. *Nat Rev Gastroenterol Hepatol* 6, 412-422 (2009).

14. Fulda, S. Apoptosis pathways and their therapeutic exploitation in pancreatic cancer. *J Cell Mol Med* 13, 1221-1227 (2009).

15. Eser, S., Schnieke, A., Schneider, G. & Saur, D. Oncogenic KRAS signalling in pancreatic cancer. *British journal of cancer* (2014).

16. Li, L. C. et al. Small dsRNAs induce transcriptional activation in human cells. *Proceedings of the National Academy of Sciences of the United States of America* 103, 17337-17342 (2006).

17. Janowski, B. A. et al. Activating gene expression in mammalian cells with promoter-targeted duplex RNAs. *Nat Chem Biol* 3, 166-173 (2007).

18. Reebye, V. et al. Novel RNA oligonucleotide improves liver function and inhibits liver carcinogenesis in vivo. *Hepatology* (2013).

19. Yamamoto, K. et al. Loss of histone demethylase KDM6B enhances aggressiveness of pancreatic cancer through downregulation of C/EBPalpha. *Carcinogenesis* (2014).

20. Kumagai, T. et al. Epigenetic regulation and molecular characterization of C/EBPalpha in pancreatic cancer cells. *International journal of cancer. Journal international du cancer* 124, 827-833 (2009).

21. Ellington, A. D. & Szostak, J. W. In vitro selection of RNA molecules that bind specific ligands. *Nature* 346, 818-822 (1990).

22. Tuerk, C. Using the SELEX combinatorial chemistry process to find high affinity nucleic acid ligands to target molecules. *Methods Mol Biol* 67, 219-230 (1997).

23. Ulrich, H., Magdesian, M. H., Alves, M. J. & Colli, W. In vitro selection of RNA aptamers that bind to cell adhesion receptors of *Trypanosoma cruzi* and inhibit cell invasion. *J Biol Chem* 277, 20756-20762 (2002).

24. Wang, J., Jiang, H. & Liu, F. In vitro selection of novel RNA ligands that bind human cytomegalovirus and block viral infection. *RNA* 6, 571-583 (2000).

25. Blank, M., Weinschenk, T., Priemer, M. & Schluesener, H. Systematic evolution of a DNA aptamer binding to rat brain tumor microvessels. selective targeting of endothelial regulatory protein pigpen. *J Biol Chem* 276, 16464-16468 (2001).

26. Daniels, D. A., Chen, H., Hicke, B. J., Swiderek, K. M. & Gold, L. A tenascin-C aptamer identified by tumor cell SELEX: systematic evolution of ligands by exponential enrichment. *Proceedings of the National Academy of Sciences of the United States of America* 100, 15416-15421 (2003).

27. Hicke, B. J. et al. Tenascin-C aptamers are generated using tumor cells and purified protein. *J Biol Chem* 276, 48644-48654 (2001).

28. Wilson, D. S. & Szostak, J. W. In vitro selection of functional nucleic acids. *Annu Rev Biochem* 68, 611-647 (1999).

29. Que-Gewirth, N. S. & Sullenger, B. A. Gene therapy progress and prospects: RNA aptamers. *Gene therapy* 14, 283-291 (2007).

30. Zuker, M. Mfold web server for nucleic acid folding and hybridization prediction. *Nucleic Acids Res* 31, 3406-3415 (2003).

31. Antoniou, G., Kountourakis, P., Papadimitriou, K., Vassiliou, V. & Papamichael, D. Adjuvant therapy for resectable pancreatic adenocarcinoma: Review of the current treatment approaches and future directions. *Cancer treatment reviews* (2013).

32. Moore, M. J. et al. Erlotinib plus gemcitabine compared with gemcitabine alone in patients with advanced pancreatic cancer: a phase III trial of the National Cancer Institute of Canada Clinical Trials Group. *Journal of clinical oncology: official journal of the American Society of Clinical Oncology* 25, 1960-1966 (2007).

33. Kim, Y. H. et al. An RNA aptamer that specifically binds pancreatic adenocarcinoma up-regulated factor inhibits migration and growth of pancreatic cancer cells. *Cancer letters* 313, 76-83 (2011).

34. Rhim, A. D. et al. EMT and dissemination precede pancreatic tumor formation. *Cell* 148, 349-361 (2012).

35. Elpek, G. O., Karaveli, S., Simsek, T., Keles, N. & Aksoy, N. H. Expression of heat-shock proteins hsp27, hsp70 and hsp90 in malignant epithelial tumour of the ovaries. *APMIS: acta pathologica, microbiologica, et immunologica Scandinavica* 111, 523-530 (2003).

36. Sliutz, G. et al. Drug resistance against gemcitabine and topotecan mediated by constitutive hsp70 overexpression in vitro: implication of quercetin as sensitiser in chemotherapy. *British journal of cancer* 74, 172-177 (1996).

37. Garrido, C. et al. Heat shock proteins 27 and 70: anti-apoptotic proteins with tumorigenic properties. *Cell cycle* 5, 2592-2601 (2006).

38. Aghdassi, A. et al. Heat shock protein 70 increases tumorigenicity and inhibits apoptosis in pancreatic adenocarcinoma. *Cancer research* 67, 616-625 (2007).

39. Shin, B. K. et al. Global profiling of the cell surface proteome of cancer cells uncovers an abundance of proteins with chaperone function. *The Journal of biological chemistry* 278, 7607-7616 (2003).

40. Hantschel, M. et al. Hsp70 plasma membrane expression on primary tumor biopsy material and bone marrow of leukemic patients. *Cell stress & chaperones* 5, 438-442 (2000).

41. Gehrmann, M. et al. Tumor-specific Hsp70 plasma membrane localization is enabled by the glycosphingolipid Gb3. *PloS one* 3, e1925 (2008).

42. Mahalka, A. K., Kirkegaard, T., Jukola, L. T., Jaattela, M. & Kinnunen, P. K. Human heat shock protein 70 (Hsp70) as a peripheral membrane protein. *Biochimica et biophysica acta* 1838, 1344-1361 (2014).

43. Arispe, N., Doh, M., Simakova, O., Kurganov, B. & De Maio, A. Hsc70 and Hsp70 interact with phosphatidylserine on the surface of PC12 cells resulting in a decrease of viability. *FASEB journal: official publication of the Federation of American Societies for Experimental Biology* 18, 1636-1645 (2004).

44. Pasquier, J. et al. Preferential transfer of mitochondria from endothelial to cancer cells through tunneling nanotubes modulates chemoresistance. *Journal of translational medicine* 11, 94 (2013).

45. Bottoni, P., Giardina, B., Pontoglio, A., Scara, S. & Scatena, R. Mitochondrial proteomic approaches for new potential diagnostic and prognostic biomarkers in cancer. *Advances in experimental medicine and biology* 942, 423-440 (2012).

46. Chen, Y. W. et al. Mitochondrial proteomics analysis of tumorigenic and metastatic breast cancer markers. *Functional & integrative genomics* 11, 225-239 (2011).

47. Yang, X. et al. Hsp70 promotes chemoresistance by blocking Bax mitochondrial translocation in ovarian cancer cells. *Cancer letters* 321, 137-143 (2012).

48. Hyun, J. J. et al. Expression of heat shock protein 70 modulates the chemoresponsiveness of pancreatic cancer. *Gut and liver* 7, 739-746 (2013).

49. Rerole, A. L. et al. Peptides and aptamers targeting HSP70: a novel approach for anticancer chemotherapy. *Cancer research* 71, 484-495 (2011).

50. Dua, P. et al. Alkaline phosphatase ALPPL-2 is a novel pancreatic carcinoma-associated protein. *Cancer research* 73, 1934-1945 (2013).

51. Ray, P., Rialon-Guevara, K. L., Veras, E., Sullenger, B. A. & White, R. R. Comparing human pancreatic cell secretomes by in vitro aptamer selection identifies cyclophilin B as a candidate pancreatic cancer biomarker. *The Journal of clinical investigation* 122, 1734-1741 (2012).

52. Yoon, S. et al. Neutralization of infectivity of porcine circovirus type 2 (PCV2) by capsid-binding 2'F-RNA aptamers. *Antiviral research* 88, 19-24 (2010).

53. Sefah, K., Shangguan, D., Xiong, X., O'Donoghue, M. B. & Tan, W. Development of DNA aptamers using Cell-SELEX. *Nature protocols* 5, 1169-1185 (2010).

Aghdassi, A., P. Phillips, V. Dudeja, D. Dhaulakhandi, R. Sharif, R. Dawra, M. M. Lerch and A. Saluja (2007). "Heat shock protein 70 increases tumorigenicity and inhibits apoptosis in pancreatic adenocarcinoma." Cancer Res 67(2): 616-625.

Arispe, N., M. Doh, O. Simakova, B. Kurganov and A. De Maio (2004). "Hsc70 and Hsp70 interact with phosphatidylserine on the surface of PC12 cells resulting in a decrease of viability." FASEB J 18(14): 1636-1645.

Blank, M., T. Weinschenk, M. Priemer and H. Schluesener (2001). "Systematic evolution of a DNA aptamer binding to rat brain tumor microvessels. selective targeting of endothelial regulatory protein pigpen." J Biol Chem 276(19): 16464-16468.

Bottinger, L., B. Guiard, S. Oeljeklaus, B. Kulawiak, N. Zufall, N. Wiedemann, B. Warscheid, M. van der Laan and T. Becker (2013). "A complex of Cox4 and mitochondrial Hsp70 plays an important role in the assembly of the cytochrome c oxidase." Mol Biol Cell 24(17): 2609-2619.

Bottoni, P., B. Giardina, A. Pontoglio, S. Scara and R. Scatena (2012). "Mitochondrial proteomic approaches for new potential diagnostic and prognostic biomarkers in cancer." Adv Exp Med Biol 942: 423-440.

Burris, H. A., 3rd, M. J. Moore, J. Andersen, M. R. Green, M. L. Rothenberg, M. R. Modiano, M. C. Cripps, R. K. Portenoy, A. M. Storniolo, P. Tarassoff, R. Nelson, F. A. Dorr, C. D. Stephens and D. D. Von Hoff (1997). "Improvements in survival and clinical benefit with gemcitabine as first-line therapy for patients with advanced pancreas cancer: a randomized trial." J Clin Oncol 15(6): 2403-2413.

Chen, Y. W., H. C. Chou, P. C. Lyu, H. S. Yin, F. L. Huang, W. S. Chang, C. Y. Fan, I. F. Tu, T. C. Lai, S. T. Lin, Y. C. Lu, C. L. Wu, S. H. Huang and H. L. Chan (2011). "Mitochondrial proteomics analysis of tumorigenic and metastatic breast cancer markers." Funct Integr Genomics 11(2): 225-239.

Daniels, D. A., H. Chen, B. J. Hicke, K. M. Swiderek and L. Gold (2003). "A tenascin-C aptamer identified by tumor cell SELEX: systematic evolution of ligands by exponential enrichment." Proc Natl Acad Sci USA 100(26): 15416-15421.

Daugaard, M., T. Kirkegaard-Sorensen, M. S. Ostenfeld, M. Aaboe, M. Hoyer-Hansen, T. F. Orntoft, M. Rohde and M. Jaattela (2007). "Lens epithelium-derived growth factor is an Hsp70-2 regulated guardian of lysosomal stability in human cancer." Cancer Res 67(6): 2559-2567.

Ellington, A. D. and J. W. Szostak (1990). "In vitro selection of RNA molecules that bind specific ligands." Nature 346(6287): 818-822.

Elpek, G. O., S. Karaveli, T. Simsek, N. Keles and N. H. Aksoy (2003). "Expression of heat-shock proteins hsp27, hsp70 and hsp90 in malignant epithelial tumour of the ovaries." APMIS 111(4): 523-530.

Farrell, J. J., H. Elsaleh, M. Garcia, R. Lai, A. Ammar, W. F. Regine, R. Abrams, A. B. Benson, J. Macdonald, C. E. Cass, A. P. Dicker and J. R. Mackey (2009). "Human equilibrative nucleoside transporter 1 levels predict response to gemcitabine in patients with pancreatic cancer." Gastroenterology 136(1): 187-195.

Fukunaga, A. K., S. Marsh, D. J. Murry, T. D. Hurley and H. L. McLeod (2004). "Identification and analysis of single-nucleotide polymorphisms in the gemcitabine pharmacologic pathway." Pharmacogenomics J 4(5): 307-314.

Gabai, V. L., J. A. Yaglom, T. Waldman and M. Y. Sherman (2009). "Heat shock protein Hsp72 controls oncogene-induced senescence pathways in cancer cells." Mol Cell Biol 29(2): 559-569.

Gandhi, V., J. Legha, F. Chen, L. W. Hertel and W. Plunkett (1996). "Excision of 2',2'-difluorodeoxycytidine (gemcitabine) monophosphate residues from DNA." Cancer Res 56(19): 4453-4459.

Gandhi, V. and W. Plunkett (1990). "Modulatory activity of 2',2'-difluorodeoxycytidine on the phosphorylation and cytotoxicity of arabinosyl nucleosides." Cancer Res 50(12): 3675-3680.

Garrido, C., M. Brunet, C. Didelot, Y. Zermati, E. Schmitt and G. Kroemer (2006). "Heat shock proteins 27 and 70: anti-apoptotic proteins with tumorigenic properties." Cell Cycle 5(22): 2592-2601.

Gehrmann, M., G. Liebisch, G. Schmitz, R. Anderson, C. Steinem, A. De Maio, G. Pockley and G. Multhoff (2008). "Tumor-specific Hsp70 plasma membrane localization is enabled by the glycosphingolipid Gb3." PLoS One 3(4): e1925.

Giovannetti, E., M. Del Tacca, V. Mey, N. Funel, S. Nannizzi, S. Ricci, C. Orlandini, U. Boggi, D. Campani, M. Del Chiaro, M. Iannopollo, G. Bevilacqua, F. Mosca and R. Danesi (2006). "Transcription analysis of human equilibrative nucleoside transporter-1 predicts survival in pancreas cancer patients treated with gemcitabine." Cancer Res 66(7): 3928-3935.

Hantschel, M., K. Pfister, A. Jordan, R. Scholz, R. Andreesen, G. Schmitz, H. Schmetzer, W. Hiddemann and G. Multhoff (2000). "Hsp70 plasma membrane expression on primary tumor biopsy material and bone marrow of leukemic patients." Cell Stress Chaperones 5(5): 438-442.

Heinemann, V., L. W. Hertel, G. B. Grindey and W. Plunkett (1988). "Comparison of the cellular pharmacokinetics and toxicity of 2',2'-difluorodeoxycytidine and 1-beta-D-arabinofuranosylcytosine." Cancer Res 48(14): 4024-4031.

Hertel, L. W., G. B. Boder, J. S. Kroin, S. M. Rinzel, G. A. Poore, G. C. Todd and G. B. Grindey (1990). "Evaluation of the antitumor activity of gemcitabine (2',2'-difluoro-2'-deoxycytidine)." Cancer Res 50(14): 4417-4422.

Hertel L W, K. J., Misner J W, Tustin J M, (1988). "Synthesis of 2-deoxy-2',2'difluro-D-Ribose and 2-deoxy-2',2'difluoro-D-ribofuranosyl nucleosides." J Org Chem 53: 2406-2409.

Hicke, B. J., C. Marion, Y. F. Chang, T. Gould, C. K. Lynott, D. Parma, P. G. Schmidt and S. Warren (2001). "Tenascin-C aptamers are generated using tumor cells and purified protein." J Biol Chem 276(52): 48644-48654.

Huang, P., S. Chubb, L. W. Hertel, G. B. Grindey and W. Plunkett (1991). "Action of 2',2'-difluorodeoxycytidine on DNA synthesis." Cancer Res 51(22): 6110-6117.

L. Pauling (1945). The Nature of the Chemical Bond, Cornell University Press, Ithaca.

Leu, J. I., J. Pimkina, A. Frank, M. E. Murphy and D. L. George (2009). "A small molecule inhibitor of inducible heat shock protein 70." Mol Cell 36(1): 15-27.

Mahalka, A. K., T. Kirkegaard, L. T. Jukola, M. Jaattela and P. K. Kinnunen (2014). "Human heat shock protein 70 (Hsp70) as a peripheral membrane protein." Biochim Biophys Acta 1838(5): 1344-1361.

Murphy, M. E. (2013). "The HSP70 family and cancer." Carcinogenesis 34(6): 1181-1188.

Nakahira, S., S. Nakamori, M. Tsujie, Y. Takahashi, J. Okami, S. Yoshioka, M. Yamasaki, S. Marubashi, I. Takemasa, A. Miyamoto, Y. Takeda, H. Nagano, K. Dono, K. Umeshita, M. Sakon and M. Monden (2007). "Involvement of ribonucleotide reductase M1 subunit overexpression in gemcitabine resistance of human pancreatic cancer." Int J Cancer 120(6): 1355-1363.

Nakano, Y., S. Tanno, K. Koizumi, T. Nishikawa, K. Nakamura, M. Minoguchi, T. Izawa, Y. Mizukami, T. Okumura and Y. Kohgo (2007). "Gemcitabine chemoresistance and molecular markers associated with gemcitabine transport and metabolism in human pancreatic cancer cells." Br J Cancer 96(3): 457-463.

Nylandsted, J., M. Gyrd-Hansen, A. Danielewicz, N. Fehrenbacher, U. Lademann, M. Hoyer-Hansen, E. Weber, G. Multhoff, M. Rohde and M. Jaattela (2004). "Heat shock protein 70 promotes cell survival by inhibiting lysosomal membrane permeabilization." J Exp Med 200(4): 425-435.

Nylandsted, J., M. Rohde, K. Brand, L. Bastholm, F. Elling and M. Jaattela (2000). "Selective depletion of heat shock protein 70 (Hsp70) activates a tumor-specific death program that is independent of caspases and bypasses Bcl-2." Proc Natl Acad Sci USA 97(14): 7871-7876.

Ohhashi, S., K. Ohuchida, K. Mizumoto, H. Fujita, T. Egami, J. Yu, H. Toma, S. Sadatomi, E. Nagai and M. Tanaka (2008). "Down-regulation of deoxycytidine kinase enhances acquired resistance to gemcitabine in pancreatic cancer." Anticancer Res 28(4B): 2205-2212.

Pasquier, J., B. S. Guerrouahen, H. Al Thawadi, P. Ghiabi, M. Maleki, N. Abu-Kaoud, A. Jacob, M. Mirshahi, L. Galas, S. Rafii, F. Le Foll and A. Rafii (2013). "Preferential transfer of mitochondria from endothelial to cancer cells through tunneling nanotubes modulates chemoresistance." J Transl Med 11: 94.

Polla, B. S., S. Kantengwa, D. Francois, S. Salvioli, C. Franceschi, C. Marsac and A. Cossarizza (1996). "Mitochondria are selective targets for the protective effects of heat shock against oxidative injury." Proc Natl Acad Sci USA 93(13): 6458-6463.

Pourquier, P., C. Gioffre, G. Kohlhagen, Y. Urasaki, F. Goldwasser, L. W. Hertel, S. Yu, R. T. Pon, W. H. Gmeiner and Y. Pommier (2002). "Gemcitabine (2',2'-difluoro-2'-deoxycytidine), an antimetabolite that poisons topoisomerase I." Clin Cancer Res 8(8): 2499-2504.

Que-Gewirth, N. S. and B. A. Sullenger (2007). "Gene therapy progress and prospects: RNA aptamers." Gene Ther 14(4): 283-291.

Rerole, A. L., J. Gobbo, A. De Thonel, E. Schmitt, J. P. Pais de Barros, A. Hammann, D. Lanneau, E. Fourmaux, O. Deminov, O. Micheau, L. Lagrost, P. Colas, G. Kroemer and C. Garrido (2011). "Peptides and aptamers targeting HSP70: a novel approach for anticancer chemotherapy." Cancer Res 71(2): 484-495.

Ruiz van Haperen, V. W., G. Veerman, J. B. Vermorken and G. J. Peters (1993). "2',2'-Difluoro-deoxycytidine (gemcitabine) incorporation into RNA and DNA of tumour cell lines." Biochem Pharmacol 46(4): 762-766.

Schy, W. E., L. W. Hertel, J. S. Kroin, L. B. Bloom, M. F. Goodman and F. C. Richardson (1993). "Effect of a template-located 2',2'-difluorodeoxycytidine on the kinetics and fidelity of base insertion by Klenow (3'→5'exonuclease-) fragment." Cancer Res 53(19): 4582-4587.

Shin, B. K., H. Wang, A. M. Yim, F. Le Naour, F. Brichory, J. H. Jang, R. Zhao, E. Purays, J. Tra, C. W. Michael, D. E. Misek and S. M. Hanash (2003). "Global profiling of the cell surface proteome of cancer cells uncovers an abundance of proteins with chaperone function." J Biol Chem 278(9): 7607-7616.

Skrypek, N., B. Duchene, M. Hebbar, E. Leteurtre, I. van Seuningen and N. Jonckheere (2013). "The MUC4 mucin mediates gemcitabine resistance of human pancreatic cancer cells via the Concentrative Nucleoside Transporter family." Oncogene 32(13): 1714-1723.

Sliutz, G., J. Karlseder, C. Tempfer, L. Orel, G. Holzer and M. M. Simon (1996). "Drug resistance against gemcitabine and topotecan mediated by constitutive hsp70 overexpression in vitro: implication of quercetin as sensitiser in chemotherapy." Br J Cancer 74(2): 172-177.

Strunecka, A. and J. Patocka (1999). "[Reassessment of the role of aluminum in the development of Alzheimer's disease]." Cesk Fysiol 48(1): 9-15.

Strunecka, A., O. Strunecky and J. Patocka (2002). "Fluoride plus aluminum: useful tools in laboratory investigations, but messengers of false information." Physiol Res 51(6): 557-564.

Tuerk, C. (1997). "Using the SELEX combinatorial chemistry process to find high affinity nucleic acid ligands to target molecules." Methods Mol Biol 67: 219-230.

Ulrich, H., M. H. Magdesian, M. J. Alves and W. Colli (2002). "In vitro selection of RNA aptamers that bind to cell adhesion receptors of *Trypanosoma cruzi* and inhibit cell invasion." J Biol Chem 277(23): 20756-20762.

Wang, J., H. Jiang and F. Liu (2000). "In vitro selection of novel RNA ligands that bind human cytomegalovirus and block viral infection." RNA 6(4): 571-583.

Watanabe, M., S. Sheriff, K. B. Lewis, S. L. Tinch, J. Cho, A. Balasubramaniam and M. A. Kennedy (2012). "HMGA-targeted phosphorothioate DNA aptamers increase sensitivity to gemcitabine chemotherapy in human pancreatic cancer cell lines." Cancer Lett 315(1): 18-27.

Wilson, D. S. and J. W. Szostak (1999). "In vitro selection of functional nucleic acids." Annu Rev Biochem 68: 611-647.

Wu, W., J. Sigmond, G. J. Peters and R. F. Borch (2007). "Synthesis and biological activity of a gemcitabine phosphoramidate prodrug." J Med Chem 50(15): 3743-3746.

Yaglom, J. A., V. L. Gabai and M. Y. Sherman (2007). "High levels of heat shock protein Hsp72 in cancer cells suppress default senescence pathways." Cancer Res 67(5): 2373-2381.

Yang, X., J. Wang, Y. Zhou, Y. Wang, S. Wang and W. Zhang (2012). "Hsp70 promotes chemoresistance by blocking Bax mitochondrial translocation in ovarian cancer cells." Cancer Lett 321(2): 137-143.

EMBODIMENTS

Embodiment 1. A nucleic acid compound comprising an RNA sequence having at least 80% sequence identity to SEQ ID NO:1, wherein said nucleic acid compound does not comprise an RNA sequence of SEQ ID NO:2, SEQ ID NO:3, SEQ ID NO:4, SEQ ID NO:5, SEQ ID NO:6 or SEQ ID NO:7.

Embodiment 2. The nucleic acid compound of embodiment 1, wherein said RNA sequence is less than 88 nucleotides in length.

Embodiment 3. The nucleic acid compound of embodiment 2, wherein said RNA sequence is less than 80 nucleotides in length.

Embodiment 4. The nucleic acid compound of embodiment 2, wherein said RNA sequence is less than 70 nucleotides in length.

Embodiment 5. The nucleic acid compound of embodiment 2, wherein said RNA sequence is less than 60 nucleotides in length.

Embodiment 6. The nucleic acid compound of embodiment 2, wherein said RNA sequence is less than 50 nucleotides in length.

Embodiment 7. The nucleic acid compound of embodiment 2, wherein said RNA sequence is less than 40 nucleotides in length.

Embodiment 8. The nucleic acid compound of embodiment 2, wherein said RNA sequence is less than 30 nucleotides in length.

Embodiment 9. The nucleic acid compound of embodiment 2, wherein said RNA sequence is 28 nucleotides in length.

Embodiment 10. The nucleic acid compound of any one of embodiments 1-9, further comprising a compound moiety covalently attached to said RNA sequence.

Embodiment 11. The nucleic acid compound of embodiment 10, wherein said compound moiety is a therapeutic moiety or an imaging moiety.

Embodiment 12. The nucleic acid compound of embodiment 11, wherein said therapeutic moiety is a nucleic acid moiety, a peptide moiety or a small molecule drug moiety.

Embodiment 13. The nucleic acid compound of embodiment 11, wherein said therapeutic moiety is an activating nucleic acid moiety or an antisense nucleic acid moiety.

Embodiment 14. The nucleic acid compound of embodiment 11, wherein said therapeutic moiety is an miRNA moiety, mRNA moiety, siRNA moiety or an saRNA moiety.

Embodiment 15. The nucleic acid compound of embodiment 11, wherein said therapeutic moiety is an siRNA moiety or saRNA moiety.

Embodiment 16. The nucleic acid compound of one of embodiments 11 to 15, wherein said therapeutic moiety is an anticancer agent moiety.

Embodiment 17. The nucleic acid compound of embodiment 11, wherein said therapeutic moiety is a C/EBPalpha saRNA moiety.

Embodiment 18. The nucleic acid compound of embodiment 11, wherein said imaging agent moiety is a bioluminescent molecule, a photoactive molecule, a metal or a nanoparticle.

Embodiment 19. The nucleic acid compound of one of embodiments 1 to 18, wherein said RNA sequence is SEQ ID NO:1.

Embodiment 20. The nucleic acid compound of any one of embodiments 1-19, wherein said nucleic acid compound comprises an HSP70 ligand moiety.

Embodiment 21. The nucleic acid compound of any one of embodiments 1-20, wherein said nucleic acid compound is bound to a cellular receptor.

Embodiment 22. The nucleic acid compound of embodiment 21, wherein said cellular receptor is cell surface HSP70.

Embodiment 23. The nucleic acid compound of embodiment 21 or 22, wherein said cellular receptor is present on a cancer cell.

Embodiment 24. The nucleic acid compound of embodiment 23, wherein said wherein said cancer cell is a pancreatic cancer cell.

Embodiment 25. The nucleic acid compound of embodiment 23, wherein said wherein said cancer cell is a glioblastoma cell.

Embodiment 26. A pharmaceutical formulation comprising the nucleic acid compound of any one of embodiments 1-20 and a pharmaceutically acceptable excipient.

Embodiment 27. A pharmaceutical formulation comprising the nucleic acid compound of any one of embodiments 1-20 and a therapeutic agent.

Embodiment 28. The pharmaceutical formulation of embodiment 27, wherein said therapeutic agent is an anticancer agent.

Embodiment 29. A method of delivering a compound into a cell, the method comprising: (i) contacting a cell surface HSP70 with a compound comprising an HSP70 ligand moiety; and (ii) allowing said compound to pass into said cell thereby delivering said compound into said cell; wherein said compound does not comprise a nucleic acid sequence of SEQ ID NO:2, SEQ ID NO:3, SEQ ID NO:4, SEQ ID NO:5, SEQ ID NO:6 or SEQ ID NO:7.

Embodiment 30. The method of embodiment 29, wherein said cell surface HSP70 is a cell surface mHSP70.

Embodiment 31. The method of embodiment 29, further comprising detecting said nucleic acid compound in said cell thereby detecting said cell.

Embodiment 32. The method of embodiment 29, wherein said compound comprises a therapeutic agent or an imaging agent.

Embodiment 33. The method of embodiment 32, wherein said therapeutic agent is an antibody, a peptide, a nucleic acid or a small molecule.

Embodiment 34. The method of embodiment 32, wherein said imaging agent is a bioluminescent molecule, a photoactive molecule, a metal or a nanoparticle.

Embodiment 35. The method of embodiment 29, wherein said compound is a nucleic acid compound of any one of embodiments 1-20.

Embodiment 36. A method of treating cancer, the method comprising administering to a subject in need thereof an effective amount of the nucleic acid compound of any one of embodiments 1-20.

Embodiment 37. The method of embodiment 36, wherein said nucleic acid compound further comprises an anticancer therapeutic moiety.

Embodiment 38. A method of treating cancer, the method comprising administering to a subject in need thereof an effective amount of an anticancer agent and the nucleic acid compound of any one of embodiments 1-20.

What is claimed is:

1. A nucleic acid compound comprising an RNA sequence having at least 80% sequence identity to SEQ ID NO:1, wherein said nucleic acid compound does not comprise an RNA sequence of SEQ ID NO:2, SEQ ID NO:3, SEQ ID NO:4, SEQ ID NO:5, SEQ ID NO:6 or SEQ ID NO:7.

2. The nucleic acid compound of claim 1, wherein said RNA sequence is less than 88 nucleotides in length.

3. The nucleic acid compound of claim 2, wherein said RNA sequence is less than 80 nucleotides in length.

4. The nucleic acid compound of claim 2, wherein said RNA sequence is less than 70 nucleotides in length.

5. The nucleic acid compound of claim 2, wherein said RNA sequence is less than 60 nucleotides in length.

6. The nucleic acid compound of claim 2, wherein said RNA sequence is less than 50 nucleotides in length.

7. The nucleic acid compound of claim 2, wherein said RNA sequence is less than 40 nucleotides in length.

8. The nucleic acid compound of claim 2, wherein said RNA sequence is less than 30 nucleotides in length.

9. The nucleic acid compound of claim 2, wherein said RNA sequence is 28 nucleotides in length.

10. The nucleic acid compound of claim 1, further comprising a compound moiety covalently attached to said RNA sequence.

11. The nucleic acid compound of claim 10, wherein said compound moiety is a therapeutic moiety or an imaging moiety.

12. The nucleic acid compound of claim 11, wherein said therapeutic moiety is a nucleic acid moiety, a peptide moiety or a small molecule drug moiety.

13. The nucleic acid compound of claim 11, wherein said therapeutic moiety is an activating nucleic acid moiety or an antisense nucleic acid moiety.

14. The nucleic acid compound of claim 11, wherein said therapeutic moiety is an miRNA moiety, mRNA moiety, siRNA moiety or an saRNA moiety.

15. The nucleic acid compound of claim 11, wherein said therapeutic moiety is an siRNA moiety or saRNA moiety.

16. The nucleic acid compound of claim 11, wherein said therapeutic moiety is an anticancer agent moiety.

17. The nucleic acid compound of claim 11, wherein said therapeutic moiety is a C/EBPalpha saRNA moiety.

18. The nucleic acid compound of claim 11, wherein said imaging agent moiety is a bioluminescent molecule, a photoactive molecule, a metal or a nanoparticle.

19. The nucleic acid compound of claim 1, wherein said RNA sequence is SEQ ID NO:1.

20. The nucleic acid compound of claim 1, wherein said nucleic acid compound is bound to a cellular receptor.

21. The nucleic acid compound of claim 20, wherein said cellular receptor is cell surface HSP70.

22. A pharmaceutical formulation comprising the nucleic acid compound of claim 1 and a pharmaceutically acceptable excipient.

23. A pharmaceutical formulation comprising the nucleic acid compound of claim 1 and a therapeutic agent.

24. The pharmaceutical formulation of claim 23, wherein said therapeutic agent is an anticancer agent.

25. A method of treating cancer, the method comprising administering to a subject in need thereof an effective amount of the nucleic acid compound of claim 1.

26. The method of claim 25, wherein said nucleic acid compound further comprises an anticancer therapeutic moiety.

27. A method of treating cancer, the method comprising administering to a subject in need thereof an effective amount of an anticancer agent and the nucleic acid compound of claim 1.

* * * * *

SEQUENCE LISTING

<160> NUMBER OF SEQ ID NOS: 23

<210> SEQ ID NO 1
<211> LENGTH: 28
<212> TYPE: RNA
<213> ORGANISM: Artificial Sequence
<220> FEATURE:
<223> OTHER INFORMATION: Synthetic polynucleotide

<400> SEQUENCE: 1
cucaauggcg aaugcccgcc uaauaggg                                            28

<210> SEQ ID NO 2
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 2
gggagacaag aauaaacgcu caauggcgaa ugcccgccua auagggcguu augacuuguu         60
gaguucgaca ggaggcucac aacaggc                                            87

<210> SEQ ID NO 3
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 3
gggagacaag aauaaacgcu caaaguugcg gcccaaccgu uuaauucaga auagugugau         60
gccuucgaca ggaggcucac aacaggc                                            87

<210> SEQ ID NO 4
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 4
gggagacaag aauaaacgcu caaugcgcug aaugcccagc cgugaaagcg ucgauuucca         60
uccuucgaca ggaggcucac aacaggc                                            87

<210> SEQ ID NO 5
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 5
gggagacaag aauaaacgcu caaaugauug cccauucggu uaugcuugcg cuuccuaaag         60
agcuucgaca ggaggcucac aacaggc                                            87

<210> SEQ ID NO 6
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 6
gggagacaag aauaaacgcu caaggccaug uugaaugccc aacuaagcuu ugagcuuugg    60
agcuucgaca ggaggcucac aacaggc                                       87

<210> SEQ ID NO 7
<211> LENGTH: 71
<212> TYPE: RNA
<213> ORGANISM: Artificial Sequence
<220> FEATURE:
<223> OTHER INFORMATION: Synthetic polynucleotide

<400> SEQUENCE: 7
gggagacaag aauaaacgcu caacaaugga gcguuaaacg ugagccauuc gacaggaggc    60
ucacaacagg c                                                        71

<210> SEQ ID NO 8
<211> LENGTH: 8
<212> TYPE: RNA
<213> ORGANISM: Artificial Sequence
<220> FEATURE:
<223> OTHER INFORMATION: Synthetic polynucleotide

<400> SEQUENCE: 8 gaaugccc                                                             8

<210> SEQ ID NO 9
<211> LENGTH: 16
<212> TYPE: RNA
<213> ORGANISM: Artificial Sequence
<220> FEATURE:
<223> OTHER INFORMATION: Synthetic polynucleotide

<400> SEQUENCE: 9
aguuuuuuac auuuug                                                   16

<210> SEQ ID NO 10
<211> LENGTH: 16
<212> TYPE: RNA
<213> ORGANISM: Artificial Sequence
<220> FEATURE:
<223> OTHER INFORMATION: Synthetic polynucleotide

<400> SEQUENCE: 10
caaaauguaa aaaacu                                                   16

<210> SEQ ID NO 11
<211> LENGTH: 16
<212> TYPE: RNA
<213> ORGANISM: Artificial Sequence
<220> FEATURE:
<223> OTHER INFORMATION: Synthetic polynucleotide

<400> SEQUENCE: 11
ggauggaugg auggua                                                   16

<210> SEQ ID NO 12
<211> LENGTH: 16
<212> TYPE: RNA
<213> ORGANISM: Artificial Sequence
<220> FEATURE:
<223> OTHER INFORMATION: Synthetic polynucleotide

<400> SEQUENCE: 12
uaccauccau ccaucc                                                   16

```
<210> SEQ ID NO 13
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 13
ugaauuagcu guaucgucaa gg                                              22

<210> SEQ ID NO 14
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 14
uugacgauac agcuaauuca ua                                              22

<210> SEQ ID NO 15
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 15
acuguacucc ucuugaccug cu                                              22

<210> SEQ ID NO 16
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 16
caggucaaga ggaguacagu ua                                              22

<210> SEQ ID NO 17
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 17
gaagcaaagu gauacacauu u                                               21

<210> SEQ ID NO 18
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 18
auguguauca cuuugcuucu u                                               21

<210> SEQ ID NO 19
<211> LENGTH: 87
<212> TYPE: DNA
<213> ORGANISM: Artificial Sequence
<220> FEATURE:
<223> OTHER INFORMATION: Synthetic polynucleotide
```

```
<400> SEQUENCE: 19
gggagacaag aauaaacgcu caauggcgaa ugcccgccua auagggcguu atgacuuguu        60
gaguucgaca ggaggcucac aacaggc                                           87

<210> SEQ ID NO 20
<211> LENGTH: 17
<212> TYPE: RNA
<213> ORGANISM: Artificial Sequence
<220> FEATURE:
<223> OTHER INFORMATION: Synthetic polynucleotide

<400> SEQUENCE: 20
guacauucua gauacgc                                                      17

<210> SEQ ID NO 21
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 21
gggagacaag aataaacgcu caaugcgcug aaugcccagc cgugaaagcg ucgauuucca       60
uccuucgaca ggaggcucac aacaggc                                           87

<210> SEQ ID NO 22
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 22
cggucauugu cacuggucau u                                                 21

<210> SEQ ID NO 23
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 23
ugaccaguga caaugaccgu u                                                 21
```